United States Patent
Delaney

(10) Patent No.: US 10,813,949 B2
(45) Date of Patent: Oct. 27, 2020

(54) USES OF EXPANDED POPULATIONS OF HEMATOPOIETIC STEM/PROGENITOR CELLS

(71) Applicant: Fred Hutchinson Cancer Research Center, Seattle, WA (US)

(72) Inventor: Colleen Delaney, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 180 days.

(21) Appl. No.: 15/781,447

(22) PCT Filed: Dec. 5, 2016

(86) PCT No.: PCT/US2016/064908
§ 371 (c)(1),
(2) Date: Jun. 4, 2018

(87) PCT Pub. No.: WO2017/096347
PCT Pub. Date: Jun. 8, 2017

(65) Prior Publication Data
US 2018/0353541 A1    Dec. 13, 2018

Related U.S. Application Data

(60) Provisional application No. 62/263,470, filed on Dec. 4, 2015, provisional application No. 62/263,573, filed on Dec. 4, 2015.

(51) Int. Cl.
| | | |
|---|---|---|
| *A61K 35/14* | (2015.01) | |
| *A61K 35/28* | (2015.01) | |
| *A61K 39/00* | (2006.01) | |
| *A61K 35/51* | (2015.01) | |
| *A61K 35/12* | (2015.01) | |

(52) U.S. Cl.
CPC .............. *A61K 35/14* (2013.01); *A61K 35/28* (2013.01); *A61K 35/51* (2013.01); *A61K 39/001* (2013.01); *A61K 2035/122* (2013.01)

(58) Field of Classification Search
CPC ...... A61K 35/14; A61K 35/28; A61K 39/001; A61K 2035/122
See application file for complete search history.

(56) References Cited

U.S. PATENT DOCUMENTS

| | | |
|---|---|---|
| 5,004,681 A | 4/1991 | Boyse et al. |
| 5,648,464 A | 7/1997 | Artavanis-Tsakonas et al. |
| 5,780,300 A | 7/1998 | Artavanis-Tsakonas et al. |
| 5,849,869 A | 12/1998 | Artavanis-Tsakonas et al. |
| 5,856,441 A | 1/1999 | Artavanis-Tsakonas et al. |
| 7,147,626 B2 | 12/2006 | Goodman et al. |
| 7,270,810 B2 | 9/2007 | Reisner et al. |
| 7,399,633 B2 | 7/2008 | Bernstein et al. |
| 2002/0132343 A1 | 9/2002 | Lum |
| 2012/0269774 A1 | 10/2012 | Ichim et al. |
| 2013/0095079 A1 | 4/2013 | Bernstein et al. |
| 2013/0095080 A1* | 4/2013 | Bernstein .............. G16B 30/00 424/93.7 |
| 2013/0344037 A1 | 12/2013 | Edinger et al. |
| 2015/0283235 A1 | 10/2015 | Hirai et al. |

FOREIGN PATENT DOCUMENTS

| | | |
|---|---|---|
| WO | WO9312141 A1 | 6/1993 |
| WO | WO9503062 | 2/1995 |
| WO | WO9614853 | 5/1996 |
| WO | WO9627610 A1 | 9/1996 |
| WO | WO2006047569 A2 | 5/2006 |
| WO | WO2007095594 A2 | 8/2007 |
| WO | WO2013086436 A1 | 6/2013 |
| WO | WO2013179633 A1 | 12/2013 |

OTHER PUBLICATIONS

Scandling et al., Chimerism, graft survival, and withdrawal of immunosuppressive drugs in HLA matched and mismatched patients after living donor kidney and hematopoietic cell transplantation. American Journal of Transplantation, vol. 15, No. 13 (Mar. 2015) pp. 695-704 (Year: 2015).*
Ende et al., The feasibility of using blood bank-stored (4° C.) cord blood, unmatched for HLA for marrow transplantation. American Journal of Clinical Pathology, vol. 111 (1999) pp. 773-781. (Year: 1999).*
A de Vries-van der Zwan, et al., "Haematopoietic stem cells can induce specific skin graft acceptance across full MHC barriers," Bone Marrow Transplant, vol. 22, 1998, pp. 91-98.
Anderson & Matzinger, "Immunity or tolerance: opposite outcomes of microchimerism from skin grafts," Nat. Med., vol. 7, No. 1, 2001, pp. 80-87.
Azzawi, et al., "Rantes chemokine expression is related to acute cardiac cellular rejection and infiltration by CD45RO T-lymphocytes and macrophages," J. Heart Lung Transplant, vol. 17, 1998, pp. 881-887.
Benichou, et al., "Immune recognition and rejection of allogenic skin grafts," Immunotherapy, vol. 3, No. 6, 2011, pp. 757-770.
Brunstein, et al., "Umbilical cord blood transplantation for myeloid malignancies," Blood, vol. 110, 2007, pp. 3064-3070.
Cobbold, et al., "Monoclonal antibodies to promote marrow engraftment and tissue graft tolerance," Nature, vol. 323, 1986, pp. 164-166.
Delaney, et al., "Dose-Dependent effects of the North ligand Delta1 on ex vivo differentiation and in vivo marrow repopulating ability of cord blood cells," Blood, vol. 106, 2005, pp. 2693-2699.
Delaney, et al., "Notch-mediated Expansion of Human Cord Blood Progenitor Cells Capable of Rapid Myeloid Reconstitution," Nat. Med., vol. 16, No. 2, 2010, pp. 232-236.

(Continued)

*Primary Examiner* — Kara D Johnson
(74) *Attorney, Agent, or Firm* — Lee & Hayes PC; C. Rachal Winger; Thu Nguyen

(57) ABSTRACT

Uses of expanded cord blood hematopoietic stem/progenitor cells (HSPC) are described. Examples include to reduce transplant rejection, to induce immune tolerance, to reduce total parenteral nutrition (TPN) feeding, opioid use, mucositis, and hospitalization following a medical procedure and to reduce graft versus host disease (GVHD) following an allogeneic transplant.

26 Claims, 20 Drawing Sheets

(56) References Cited

OTHER PUBLICATIONS

Donckier, et al., "Expansion of Memory-Type CD8+ T Cells Correlates With the Failure of Early Immunosuppression Withdrawal After Cadaver Liver Transplantation Using High-Dose ATG Induction and Rapamycin," Tranplantation, vol. 96, No. 3, 2013, pp. 306-315.

Granados, et al., "Hematopoietic Stem Cell Infusion/Transplantation for Induction of Allograft Tolerance," Curr. Opin. Organ. Transplant, vol. 20, No. 1, 2015, pp. 49-56.

Gray, et al., "Human ligands of the Notch receptor," Am. J. Path., vol. 154, No. 3, 1999, pp. 785-794.

Heeger, et al., "Pretransplant Frequency of Donor-Specific, IFN-gamma-Producing Lymphocytes Is a Manifestation of Immunologic Memory and Correlates with the Risk of Posttransplant Rejection Episodes," J. Immunol., vol. 163, 1999, pp. 2267-2275.

Himburg, et al., "Pleiotrophin regulates the expansion and regeneration of hematopoietic stem cells," Nature Medicine, vol. 16, No. 4, 2010, pp. 475-482.

Ildstad, et al., "Characterization of mixed allogeneic chimeras. Immunocompetence, in vitro reactivity, and genetic specificity of tolerance," J. Exp. Med., vol. 162, 1985, pp. 231-244.

Jarriault, et al., "Delta-1 activation of notch-1 signaling results in HES-1 transactivation," Mol. Cell. Biol., vol. 18, No. 12, 1998, pp. 7423-7431.

Kawai and Sachs, "Tolerance induction: hematopoietic chimerism," Curr. Opin. Organ Transplant, vol. 18, 2013, pp. 402-407.

Kawai, et al., "Long-Term Results in Recipients of Combined HLA-Mismatched Kidney and Bone Marrow Transplantation Without Maintenance Immunosuppression," Am. J. Transplant, vol. 14, No. 7, 2014, pp. 1599-1611.

Kawase, et al., "High-risk HLA allele mismatch combinations responsible for sever acute graft-versus-host disease implication for its molecular mechanism," Blood, vol. 110, 2007, pp. 2235-2241.

Kopan, et al., "The canonical Notch signaling pathway: unfolding the activation mechanism," Cell, vol. 137, No. 2, 2009, pp. 216-233.

MacMillan, et al., "Acute graft-versus-host disease after unrelated donor umbilical cord blood transplantation: analysis of risk factors," Blood, vol. 113, 2009, pp. 2410-2415.

McFarland and Rosenberg, "Skin allograft rejection," Curr. Protoc. Immunol, Chapter 4, Unit 4.4, 2009, 13 pages.

Millan, et al., "Mixed chimerism and immunosuppressive drug withdrawal after HLA-mismatched kidney and hematopoietic progenitor transplantation," Transplantation, vol. 73, 2002, pp. 1386-1391.

Olkkonen and Stenmark, "Role of Rab GTPases in membrane traffic." Int. Rev. Cytol., vol. 176, 1997, pp. 1-85.

Scandling, et al., "Chimerism, Graft Survival, and Withdrawal of Immunosuppressive Drugs in HLA Matched and Mismatched Patients After Living Donor Kidney and Hematopoietic Cell Transplantation," Am. J. Transplant, vol. 15, 2015, pp. 695-704.

Scandling, et al., "Tolerance and Chimerism after Renal and Hematopoeietic-Cell Trasplantation," N. Engl. J. Med., vol. 358, No. 4, 2008, pp. 362-368.

Schlondorff and Blobel, "Metalloprotease-disintegrins: modular proteins capable of promoting cell-cell interactions and triggering signals by protein-ectodomain shedding," J. Cell Sci., vol. 112, No. 21,1999, pp. 3603-3617.

Sorof, et al., "Renal transplantation without chronic immunosuppression after T cell-depleted, HLA-mismatched bone marrow transplantation," Transplantation, vol. 59, 1995, pp. 1633-1635.

Van Minnen, et al., "The Use of Animal Models to Study Bacterial Translocation During Acute Pancreatitis," J Gastrointest Surg., vol. 11, No. 5, 2007, pp. 682-689.

Varnum-Finney, et al., "Combined effects of Notch signaling and cytokines induce a multiple log increase in precursors with lymphoid and myeloid reconstituting ability," Hematopoiesis, vol. 101, 2003, pp. 1784-1789.

Varnum-Finney, et al., "The Notch ligand, Jagged-1, influences the development of primitive hematopietic precursor cells," Blood, vol. 91, No. 11, 1998, pp. 4084-4091.

Yamada, et al., "Repeated Injections of IL-2 Break Renal Allograft Tolerance Induced via Mixed Hematopoietic Chimerism in Monkeys," Am. J. Transplant, vol. 15, 2015, pp. 3055-3066.

Zhang, et al., "Angiopoietin-like 5 and IGFBP2 stimulate ex vivo expansion of human cord blood hematopoietic stem cells as assayed by NOD/SCID transplantation," Blood, vol. 111, No. 7, 2008, pp. 3415-3423.

Invitation to Pay Additional Fees Dated Feb. 23, 2017 for International Application No. PCT/US2016/064908.

Search Report and Written Opinion dated Apr. 28, 2017 for International Application No. PCT/US16/64908.

Extended European Search Report dated May 15, 2019 for European Patent Application No. 16871697, 9 pages.

Fuchs, "Transplantation tolerance: from theory to clinic," Immunological Reviews, vol. 258, No. 1, 2014, pp. 64-19.

Milano, et al, "Notch-Expanded Murine Hematopoietic Stem and Progenitor Cells Mitigate Death from Lethal Radiation and Convey Immune Tolerance in Mismatched Recipients: Expanded Cells Radiomitigate, Induce Tolerance," Stem Cells Translational Medicine, vol. 6, No. 2, 2016, 10 pages.

Pauw, "Infusion of donor-derived hematopoietic stem cells in organ transplantation: clinical data," Transplantation, vol. 75, No. 9, 2003, pp. 46S-49S.

Strober, "Use of hematopoietic cell transplants to achieve tolerance in patients with solid organ transplants," Blood, vol. 127, No. 12, 2016, 6 pages.

Anand, et al., "CD34+ Selection and the Severity of Oropharyngeal Mucositis in Total Body Irradiation-Based Allogeneic Stem Cell Transplantation," Support Care Cancer, vol. 24, No. 2, 2016, pp. 815-822.

Klaus, et al., "High CD34+ Cell Dose Is a Significant Factor for Hematologic Reconstitution of Patients with Multiple Myeloma (MM) or AL-Amyloidosis Undergoing Autologous Peripheral Blood Stem Cell Transplantation," Blood, vol. 104, No. 11, 2004, 5 pages.

Office Action dated Aug. 6, 2020 for Russian Application No. 2018124303, 22 pages.

Steidl, et al., "Primary human CD34+ hematopoietic stem and progenitor cells express functionally active receptors of neuromediators," Blood, vol. 104, No. 1, 2004, pp. 81-88.

\* cited by examiner

FIG. 2
[Prior Art]

| Expanded Cell Phenotype (N = 9, * N = 5) | |
|---|---|
| | Mean Percent (range) |
| CD34 | 12.8 (4.9-25) |
| CD7 | 9.7 (4.3-21) |
| CD14 | 7.7 (3.5-22) |
| CD15 | 42 (23-66) |
| CD34+/56+ | 1.8 (0.7-3.1) |
| CD3-/CD16+/56+ | 3.5 (0-9.5) |
| CD20* | 0.4 (0-1.2) |
| CD3+4+* | 0.7 (0.04-1.4) |
| CD3+8+* | 0 |
| TNC Fold Expansion | 1586 (617-3337) |
| CD34 Fold Expansion | 204 (100-387) |

FIG. 3
[Prior Art]

Pre- and Post-expansion absolute cell numbers and fold expansion

| Run | TNC (total number cells) | | | CD34 | | | Number banked (cryopreserved) Cells | | | | |
|---|---|---|---|---|---|---|---|---|---|---|---|
| | Starting Number | Ending Number | Fold Expansion | Starting Number | Ending Number | Fold Expansion | TNC | CD34+ | #Bags | TNC/Bag | CD34/Bag |
| 1 | $1.9 \times 10^8$ | $2.01 \times 10^{11}$ | 1058 | $1.65 \times 10^6$ | $2.13 \times 10^8$ | 129 | n/a | n/a | n/a | n/a | n/a |
| 2 | $1.76 \times 10^8$ | $1.20 \times 10^{11}$ | 680 | $1.41 \times 10^6$ | $3.04 \times 10^8$ | 216 | n/a | n/a | n/a | n/a | n/a |
| 3 | $2.60 \times 10^8$ | $5.47 \times 10^{11}$ | 2104 | $2.29 \times 10^6$ | $2.69 \times 10^8$ | 117 | $4.20 \times 10^9$ | $2.06 \times 10^8$ | 2 | $2.10 \times 10^9$ | $1.03 \times 10^8$ |
| 4 | $2.40 \times 10^8$ | $4.67 \times 10^{11}$ | 1944 | $2.04 \times 10^6$ | $6.07 \times 10^8$ | 298 | $2.90 \times 10^9$ | $3.77 \times 10^8$ | 1 | $2.90 \times 10^9$ | $3.77 \times 10^8$ |
| 5 | $2.17 \times 10^8$ | $3.22 \times 10^{11}$ | 1484 | $1.76 \times 10^6$ | $2.71 \times 10^8$ | 154 | $2.12 \times 10^9$ | $1.78 \times 10^8$ | 1 | $2.12 \times 10^9$ | $1.78 \times 10^8$ |
| 6 | $1.90 \times 10^8$ | $2.59 \times 10^{11}$ | 1364 | $1.70 \times 10^6$ | $1.70 \times 10^8$ | 100 | $2.00 \times 10^9$ | $1.32 \times 10^8$ | 1 | $2.00 \times 10^9$ | $1.32 \times 10^8$ |
| 7 | $4.80 \times 10^8$ | $1.60 \times 10^{11}$ | 337 | $4.32 \times 10^6$ | $1.69 \times 10^9$ | 387 | $1.29 \times 10^{10}$ | $1.35 \times 10^9$ | 4 | $3.23 \times 10^9$ | $3.38 \times 10^8$ |
| 8 | $4.86 \times 10^8$ | $9.94 \times 10^{10}$ | 2045 | $4.23 \times 10^6$ | $7.28 \times 10^8$ | 172 | $1.02 \times 10^{10}$ | $7.47 \times 10^8$ | 3 | $3.40 \times 10^9$ | $2.49 \times 10^8$ |
| 9 | $1.70 \times 10^8$ | $2.55 \times 10^{11}$ | 1499 | $1.39 \times 10^6$ | $1.46 \times 10^8$ | 105 | $2.25 \times 10^9$ | $1.29 \times 10^8$ | 1 | $2.25 \times 10^9$ | $1.29 \times 10^8$ |
| 10 | $2.06 \times 10^8$ | $3.48 \times 10^{11}$ | 1692 | $1.77 \times 10^6$ | $1.92 \times 10^8$ | 108 | $2.75 \times 10^9$ | $1.51 \times 10^8$ | 1 | $2.75 \times 10^9$ | $1.51 \times 10^8$ |
| average | $2.62 \times 10^8$ | $5.11 \times 10^{11}$ | 1723 | $2.26 \times 10^6$ | $4.59 \times 10^8$ | 179 | $4.92 \times 10^9$ | $4.09 \times 10^8$ | | $2.59 \times 10^9$ | $2.07 \times 10^8$ | n/a: not available

FIG. 4
[Prior Art]

| Unit ID | CD34 | | | CD34 Purity | | TNC | | |
|---|---|---|---|---|---|---|---|---|
| Product # | Starting # | Ending # | Fold Expansion | Starting % | Ending % | Starting # | Ending # | Fold Expansion |
| S001 | $2.29 \times 10^6$ | $2.69 \times 10^8$ | 117 | 88 | 4.9 | $2.60 \times 10^6$ | $5.47 \times 10^9$ | 2104 |
| S002 | $2.04 \times 10^6$ | $6.07 \times 10^8$ | 298 | 85 | 13 | $2.40 \times 10^6$ | $4.67 \times 10^9$ | 1944 |
| S003 | $1.76 \times 10^6$ | $2.71 \times 10^8$ | 154 | 81 | 8.4 | $2.17 \times 10^6$ | $3.22 \times 10^9$ | 1484 |
| S004 | $1.70 \times 10^6$ | $1.70 \times 10^8$ | 100 | 91 | 6.6 | $1.90 \times 10^6$ | $2.59 \times 10^9$ | 1364 |
| S005 | $4.32 \times 10^6$ | $1.69 \times 10^9$ | 387 | 90 | 10.4 | $4.80 \times 10^6$ | $1.60 \times 10^{10}$ | 3337 |
| S006 | $4.23 \times 10^6$ | $7.28 \times 10^8$ | 172 | 87 | 7.3 | $4.86 \times 10^6$ | $9.94 \times 10^9$ | 2045 |
| S007 | $1.39 \times 10^6$ | $1.46 \times 10^8$ | 105 | 82 | 5.7 | $1.70 \times 10^6$ | $2.55 \times 10^9$ | 1499 |
| S008 | $1.77 \times 10^6$ | $1.92 \times 10^8$ | 108 | 86 | 5.5 | $2.06 \times 10^6$ | $3.48 \times 10^9$ | 1692 |
| S009 | $2.70 \times 10^6$ | $4.74 \times 10^8$ | 176 | 88 | 8.8 | $3.07 \times 10^6$ | $5.42 \times 10^9$ | 1765 |
| S010 | $2.02 \times 10^6$ | $7.92 \times 10^8$ | 392 | 75 | 11.6 | $2.69 \times 10^6$ | $6.84 \times 10^9$ | 2543 |
| S011 | $1.64 \times 10^6$ | $4.25 \times 10^8$ | 259 | 82 | 15.2 | $2.00 \times 10^6$ | $2.79 \times 10^9$ | 1395 |
| S012 | $1.64 \times 10^6$ | $4.25 \times 10^8$ | 259 | 82 | 15.2 | $2.82 \times 10^6$ | $2.12 \times 10^9$ | 752 |
| S013 | $1.97 \times 10^6$ | $2.25 \times 10^8$ | 114 | 70 | 10.6 | $2.96 \times 10^6$ | $6.25 \times 10^9$ | 2111 |
| S014 | $2.28 \times 10^6$ | $6.49 \times 10^8$ | 285 | 77 | 10.4 | $2.60 \times 10^6$ | $2.15 \times 10^9$ | 827 |
| S015 | $1.74 \times 10^6$ | $1.42 \times 10^8$ | 82 | 67 | 6.63 | $2.50 \times 10^6$ | $2.97 \times 10^9$ | 1187 |
| S016 | $1.88 \times 10^6$ | $2.80 \times 10^8$ | 149 | 75 | 9.4 | $4.46 \times 10^6$ | $7.65 \times 10^9$ | 1715 |
| S017 | $3.75 \times 10^6$ | $1.04 \times 10^8$ | 276 | 84 | 13.6 | $6.90 \times 10^6$ | $4.07 \times 10^9$ | 590 |
| S018 | $6.28 \times 10^6$ | $2.91 \times 10^8$ | 46 | 91 | 7.14 | $2.34 \times 10^6$ | $2.18 \times 10^9$ | 932 |
| S019 | $1.78 \times 10^6$ | $2.29 \times 10^8$ | 129 | 7 | 10.52 | $2.16 \times 10^6$ | $2.00 \times 10^9$ | 926 |

FIG. 5
[Prior Art]

| Unit ID | Banked Cells | | | | | Final Viability |
|---|---|---|---|---|---|---|
| Product # | TNC | CD34 # | # Bags | TNC/Bag | CD34#/Bag | Trypan Blue |
| S001 | $4.20 \times 10^9$ | $2.06 \times 10^8$ | 2 | $2.10 \times 10^9$ | $1.03 \times 10^8$ | 67% |
| S002 | $2.90 \times 10^9$ | $3.77 \times 10^8$ | 1 | $2.90 \times 10^9$ | $3.77 \times 10^8$ | 62% |
| S003 | $2.12 \times 10^9$ | $1.78 \times 10^8$ | 1 | $2.12 \times 10^9$ | $1.78 \times 10^8$ | 69% |
| S004 | $2.00 \times 10^9$ | $1.32 \times 10^8$ | 1 | $2.00 \times 10^9$ | $1.32 \times 10^8$ | 55% |
| S005 | $1.29 \times 10^{10}$ | $1.35 \times 10^9$ | 4 | $3.23 \times 10^9$ | $3.38 \times 10^8$ | 67% |
| S006 | $1.02 \times 10^{10}$ | $7.47 \times 10^8$ | 3 | $3.40 \times 10^9$ | $2.49 \times 10^8$ | 57% |
| S007 | $2.25 \times 10^9$ | $1.29 \times 10^8$ | 1 | $2.25 \times 10^9$ | $1.29 \times 10^8$ | 70% |
| S008 | $2.75 \times 10^9$ | $1.51 \times 10^8$ | 1 | $2.75 \times 10^9$ | $1.51 \times 10^8$ | 79% |
| S009 | $6.30 \times 10^9$ | $5.51 \times 10^8$ | 2 | $3.15 \times 10^9$ | $2.76 \times 10^8$ | 59% |
| S010 | $4.93 \times 10^9$ | $5.70 \times 10^8$ | 2 | $2.47 \times 10^9$ | $2.85 \times 10^8$ | 66% |
| S011 | $1.82 \times 10^9$ | $2.77 \times 10^8$ | 1 | $1.82 \times 10^9$ | $2.77 \times 10^8$ | 57% |
| S012 | $1.70 \times 10^9$ | $1.81 \times 10^8$ | 1 | $1.70 \times 10^9$ | $1.81 \times 10^8$ | 59% |
| S013 | $5.14 \times 10^9$ | $5.34 \times 10^8$ | 2 | $2.57 \times 10^9$ | $2.67 \times 10^8$ | 68% |
| S014 | $1.50 \times 10^9$ | $9.91 \times 10^7$ | 1 | $1.50 \times 10^9$ | $9.91 \times 10^7$ | 68% |
| S015 | $1.94 \times 10^9$ | $1.83 \times 10^8$ | 1 | $1.94 \times 10^9$ | $1.83 \times 10^8$ | 62% |
| S016 | $4.08 \times 10^9$ | $5.53 \times 10^8$ | 2 | $2.04 \times 10^9$ | $2.76 \times 10^8$ | 54% |
| S017 | $3.90 \times 10^9$ | $2.78 \times 10^8$ | 1 | $3.90 \times 10^9$ | $2.78 \times 10^8$ | 65% |
| S018 | $1.23 \times 10^9$ | $1.29 \times 10^8$ | 1 | $1.23 \times 10^9$ | $1.29 \times 10^8$ | 68% |
| S019 | $2.19 \times 10^9$ | $2.23 \times 10^8$ | 1 | $2.19 \times 10^9$ | $2.23 \times 10^8$ | |

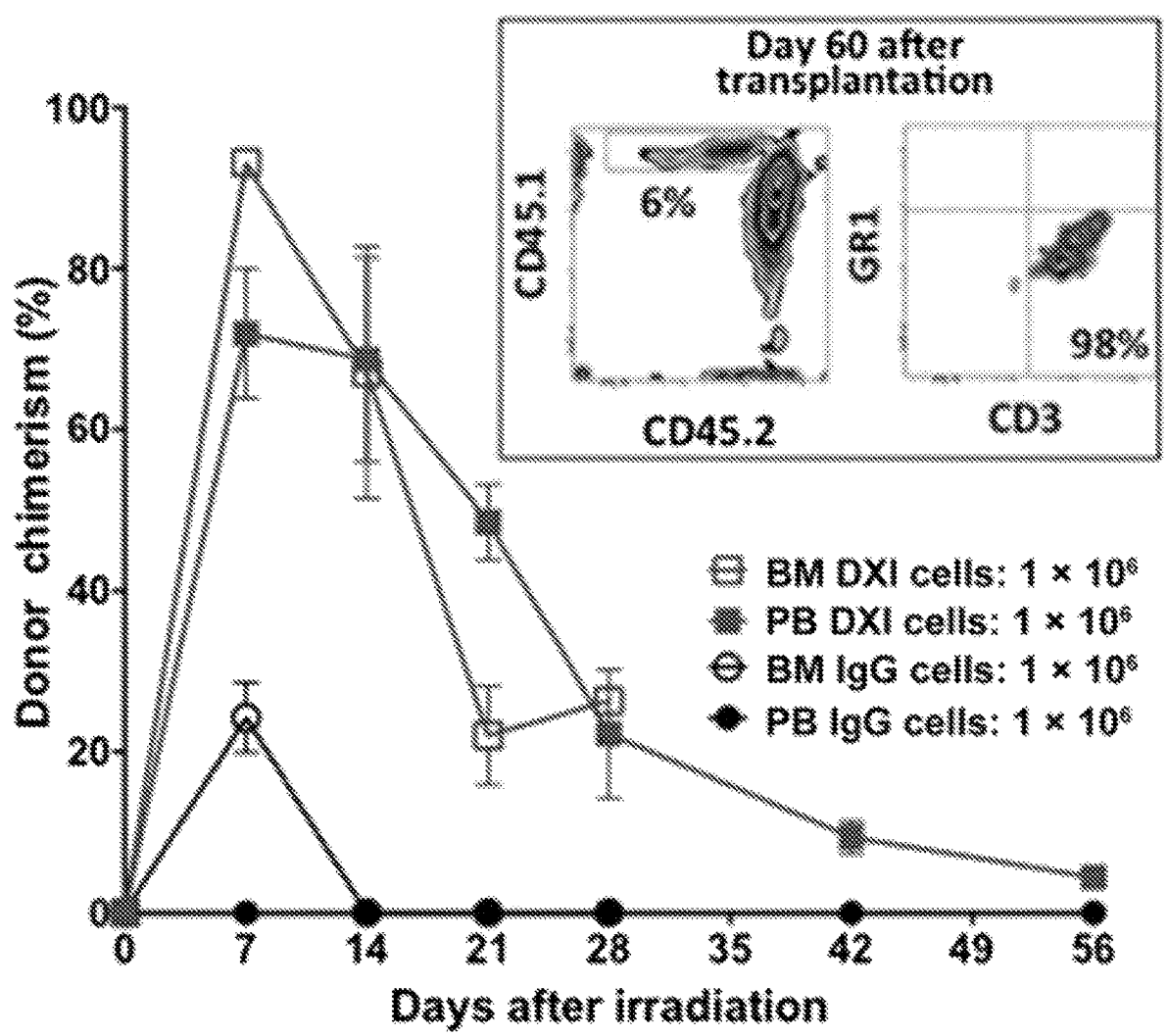

FIG. 7A
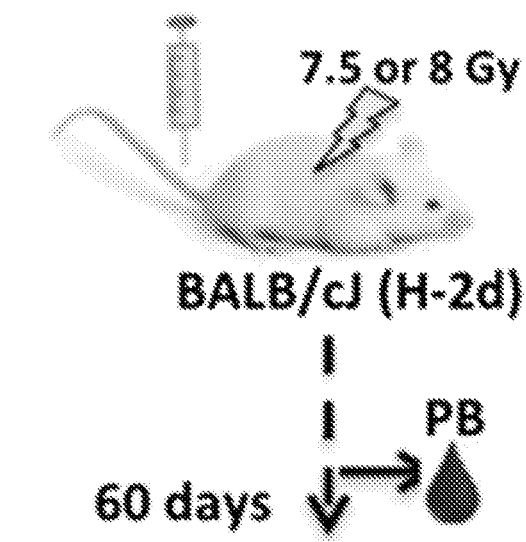
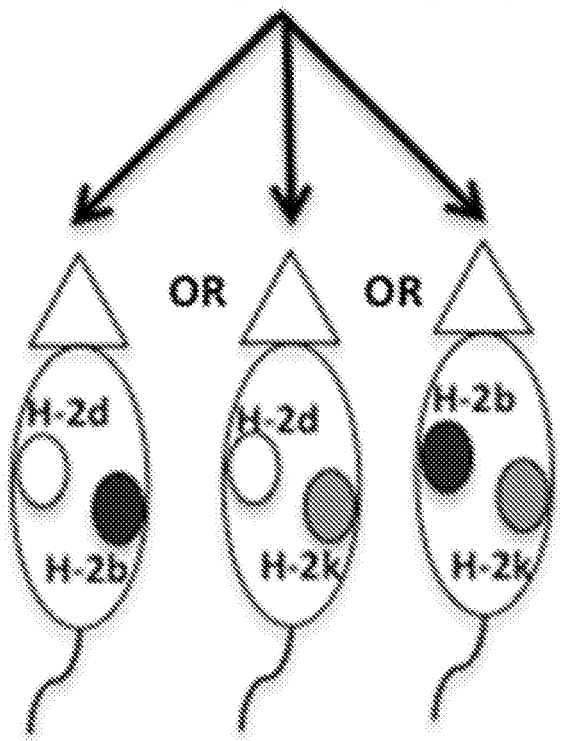

BALB/cJ BM cells (control)

DXI-cultured B6-Ly5a cells

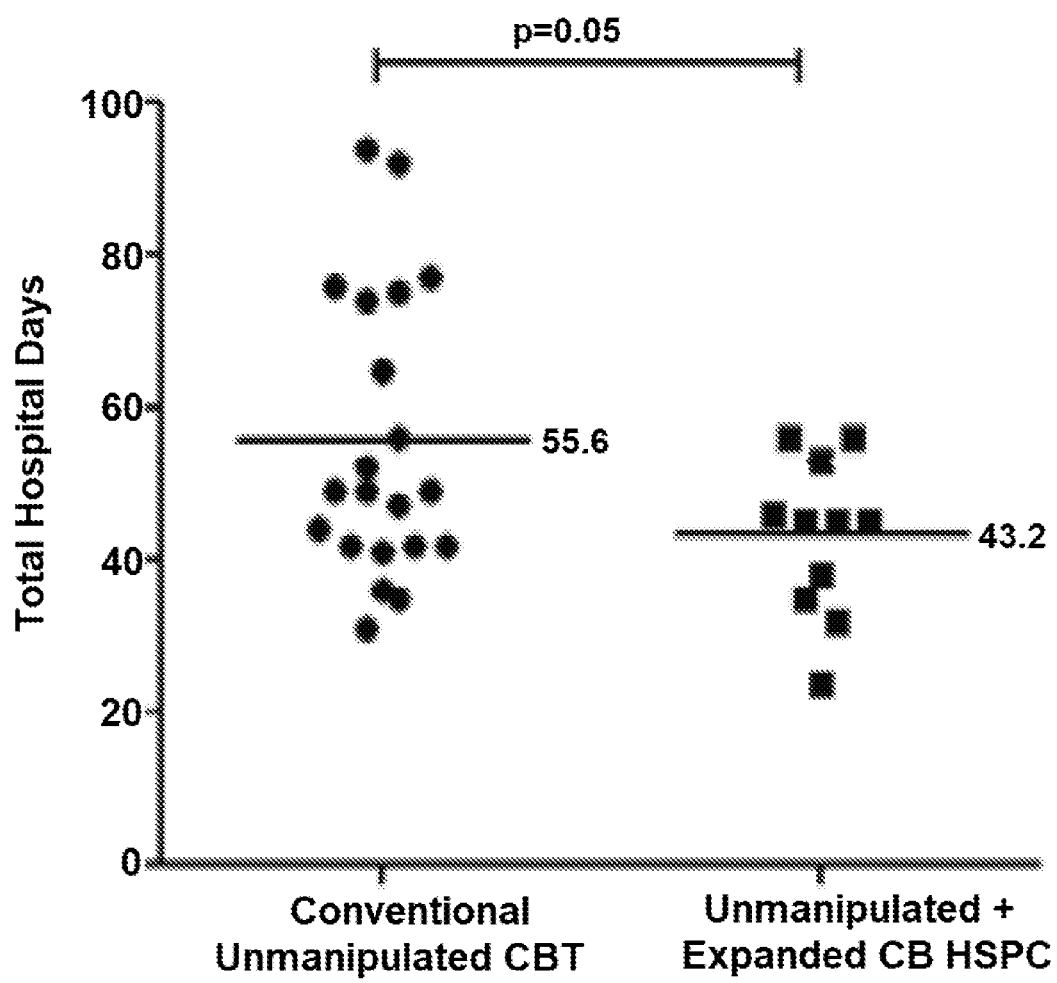

FIG. 11

| Patient Characteristics | Patients (n=15) | Controls (n=50) | p-value |
|---|---|---|---|
| Gender, No (%) | | | |
| Female | 7 (46) | 25 (50) | 1 |
| Age in years, median (range) | 21 (5 to 45) | 21 (0.6 to 43) | 0.58 |
| Weight in kilograms, median (range) | 59 (23 to 89) | 67 (8 to 109) | 0.31 |
| Diagnosis, No (%) | | | |
| ALL | 8 (53) | 16 (32) | |
| AML | 6 (40) | 24 (48) | 0.61 |
| MDS/CML | 1 (7) | 6 (12) | |
| Other | 0 | 4 (8) | |
| CMV seropositive, no. (%) | 11 (73) | 31 (50) | 0.47 |
| Race, no. (%) | | | |
| Caucasian | 6 (40) | 21 (42) | 0.22 |
| Other | 9 (60) | 29 (58) | |
| Disease Risk | | | |
| Low | - | 6 (12) | 0.37 |
| Intermediate | 11 (74) | 30 (60) | |
| High | 3 (20) | 13 (26) | |
| Very high | 1 (6) | 1 (2) | |
| MRD | 6 (40) | 19 (38) | 0.88 |
| Follow-up in years, median (range) | 3.8 (2.4 to 4.3) | 6 (1.7 - 8.8) | |
| Unit Characteristics | | | |
| Number of unmanipulated donors, No (%) | | | |
| 1 | 4 (27) | 9 (18) | |
| 2 | 11 (73) | 41 (82) | 0.46 |
| HLA match unmanipulated donors, No (%)* | | | |
| 4/6 | 9 (60) | 29 (58) | 0.60 |
| 5/6 | 6 (40) | 16 (32) | |
| 6/6 | | 5 (10) | |
| Infused Cell Doses (pre-freeze) | | | |
| Total Unmanipulated TNC/kg x $10^7$ | 6.1 (4.3 - 17.1) | 4.9 (3.4 to 16.6) | 0.03 |
| Total Unmanipulated CD34/kg x $10^6$ | 0.26 (0.08 - 0.98) | 0.19 (0.04 - 0.98) | 0.07 |
| Expanded Product TNC/kg x $10^7$ | 5.8 (2.2 - 10.9) | . | |
| Expanded Product CD34/kg x $10^6$ | 5.2 (3.1 to 11.6) | . | |

* HLA matching reflects the lowest HLA-match of the unmanipulated unit

USES OF EXPANDED POPULATIONS OF HEMATOPOIETIC STEM/PROGENITOR CELLS

CROSS REFERENCE TO RELATED APPLICATION

This application claims priority to U.S. Provisional Patent Application No. 62/263,470 filed on Dec. 4, 2015 and U.S. Provisional Patent Application No. 62/263,573 filed on Dec. 4, 2015, both of which are incorporated by reference herein in their entirety.

STATEMENT OF GOVERNMENT SUPPORT

This invention was made with government support under RC2HL101844 awarded by the National Institutes of Health and HHS0100200800064C awarded by the Department of Health and Human Services. The government has certain rights in this invention.

FIELD OF THE DISCLOSURE

Uses of expanded cord blood hematopoietic stem/progenitor cells (HSPC) are described. Examples include to reduce transplant rejection, to induce immune tolerance, to reduce total parenteral nutrition (TPN) feeding, opioid use, and hospitalization following a medical procedure, to reduce mucositis, and to reduce graft versus host disease (GVHD) following an allogeneic transplant.

BACKGROUND OF THE DISCLOSURE

US 2013/0095079 describes the development of a groundbreaking clinical product including CD34+ enriched and expanded human cord blood stem cells (Exp-CBSC) that could safely be administered to any patient without any degree of immunological matching between the patient and the clinical product. The Exp-CBSC were shown to decrease the time for immunosuppressed patients to recover immune function. For example, the Exp-CBSC helped chemotherapy patients recover immune function faster than they otherwise would have without the Exp-CBSC. The same effect was seen in patients who were severely immunocompromised after conditioning to receive a cord blood transplant as a treatment for acute myelogenous leukemia (AML) and acute lymphoblastic leukemia (ALL). The Exp-CBSC similarly helped these cord blood transplant recipient patients recover immune function faster than they otherwise would have without the Exp-CBSC. The Exp-CBSC greatly improved patient outcomes by reducing infection, disease relapse, and other often fatal treatment complications due to reduced or absent immune function.

SUMMARY OF THE DISCLOSURE

The current disclosure provides that the CD34+ enriched and expanded human cord blood stem cells (Exp-CBSC) described in US 2013/0095079 have additional unanticipated clinical benefits in varied patient populations. For example, the Exp-CBSC reduce transplant rejection, reduce total parental feeding, opioid use, and hospitalization following a medical procedure, to reduce mucositis, and reduce graft versus host disease following an allogeneic transplant. These additional unanticipated clinical benefits of the Exp-CBSC also significantly improve patient outcomes. Reduced transplant rejection, mucositis, and graft versus host disease increases survival and quality of life following a transplant. Reduced total parenteral feeding avoids the numerous complications that can arise due to such artificial feeding. Reducing patient exposure to opioid use can help address the on-going epidemic of pain killer abuse. Finally, reduced hospitalization following a medical procedure decreases costs associated with medical care and similarly reduces lost opportunity costs patients experience while hospitalized. Each of these uses and benefits is described more fully in the following Detailed Description. Individually and collectively they provide further evidence for the immense clinical benefits offered by the Exp-CBSC described in US 2013/0095079 in diverse patient populations.

BRIEF DESCRIPTION OF THE FIGURES

FIG. 2. Cell phenotypes following expansion using methods described herein and in US 2013/0095079.

FIG. 3. Pre- and post-expansion absolute cell numbers and fold expansion following culture using methods described herein and in US 2013/0095079

FIG. 4. Starting, ending and fold expansion numbers for total nucleated cells and CD34+ cells post-expansion for 19 full scale expansions using methods described herein and in US 2013/0095079.

FIG. 5. Total nucleated cell (TNC) and CD34+ cell counts for each of the expanded human cord blood stem cell samples and cell viability prior to cryopreservation, and TNC and CD34+ cell counts in each frozen bag following expansion using methods described herein and in US 2013/0095079.

FIGS. 6A-6C. Infusion of Delta1$^{ext-IgG}$ (DXI)-cultured murine cells reconstitutes major histocompatibility complex-mismatched recipients and mitigates total-body irradiation (TBI)-induced mortality. Experimental design (FIG. 6A). The LSK from B6-Ly5a (H-2b, CD45.1) mice were sorted and cultured on DXI-(5 mg/ml) or IgG-coated flasks for 2 weeks. DXI or IgG-cultured cells, fresh, at the end of culture, or previously cryopreserved were transplanted intravenously into 6- to 8-week-old BALB/cJ (H-2d, CD45.2) mice within 2-4 hours after the mice had been lethally irradiated with 8.5 Gy TBI ($^{137}$Cs γ rays). (FIG. 6B): Flow cytometric analysis of the IgG- (top panels) and DXI-cultured (lower panels) cells at the end of 14-day culture. Percentage of donor cells (45.1+) in peripheral blood (PB) and bone marrow (BM) at indicated time points after transplantation of 1×10$^6$ fresh DXI- or IgG-cultured cells (FIG. 6C). Inset shows flow cytometric analysis of donor (45.1+) cells (left panel) and myeloid and T-lymphoid lineage distribution (right panel) of donor cells in PB from a representative mouse transplanted with allogeneic DXI-cultured cells at 60 days after transplantation. Percentage of donor cells (45.1+)±standard mean error (bars) in PB and BM.

FIGS. 7A-7G. Infusion of cryopreserved allogeneic DXI-cultured cells induces donor-specific immune tolerance and improves skin graft survival. (FIG. 7A): Experimental design. BALB/cJ (H-2d) mice were transplanted with 5×10$^6$ syngeneic BALB/cJ (H-2d) BM cells (control mice, n=20) or cryo-preserved allogeneic DXI-cultured B6-Ly5a (H-2b) cells (DXI mice, n=33) within 2-4 hours after 7.5- or 8.0-Gy TBI. (FIGS. 7B, 7C): Sixty days after transplantation, each mouse received 2 skin grafts. Control mice had syngeneic H-2d (n=9), allogeneic H-2b (n=13), or third-party H-2k (n=12) skin grafts. DXI mice had syngeneic H-2d (n=21), allogeneic H-2b (n=21), or third-party H-2k (n=20) skin grafts. (FIG. 7B): Representative skin grafts in BALB/cJ (H-2d) mice transplanted with syngeneic BM cells with H-2d and H-2b or H-2d and H-2k, or H-2b and H-2k skin grafts. (FIG. 7C): Representative skin grafts in BALB/cJ (H-2d) mice transplanted with allogeneic DXI-cultured cells with H-2d and H-2b or H-2d and H-2k, or H-2b and H-2k skin grafts. (FIG. 7D): Representative healthy H-2b (arrow in bottom left panel and lower arrow in bottom right panel) and H-2d (upper arrow in bottom right panel) skin grafts in BALB/cJ mice transplanted with DXI-cultured cells 60 days after surgery. (FIGS. 7E-7G): Thirty-day skin graft survival rate of syngeneic (H-2d) (9 in control and 21 in DXI mice) (FIG. 7E), allogeneic (H-2b) (13 in control and 21 in DXI mice) (FIG. 7F), and third-party (H-2k) (12 in control and 20 DXI mice) (FIG. 7G) skin grafts. ***, p<0.001.

FIG. 8. Mean duration of initial hospitalization for pediatric patients receiving myeloablative cord blood transplantation with or without ex-vivo expanded progenitors.

FIG. 11. Unit and patient characteristics in recipients of ex-vivo expanded cells and FHCRC historical controls in patients receiving a cord blood transplant.

DETAILED DESCRIPTION

Figure 1:
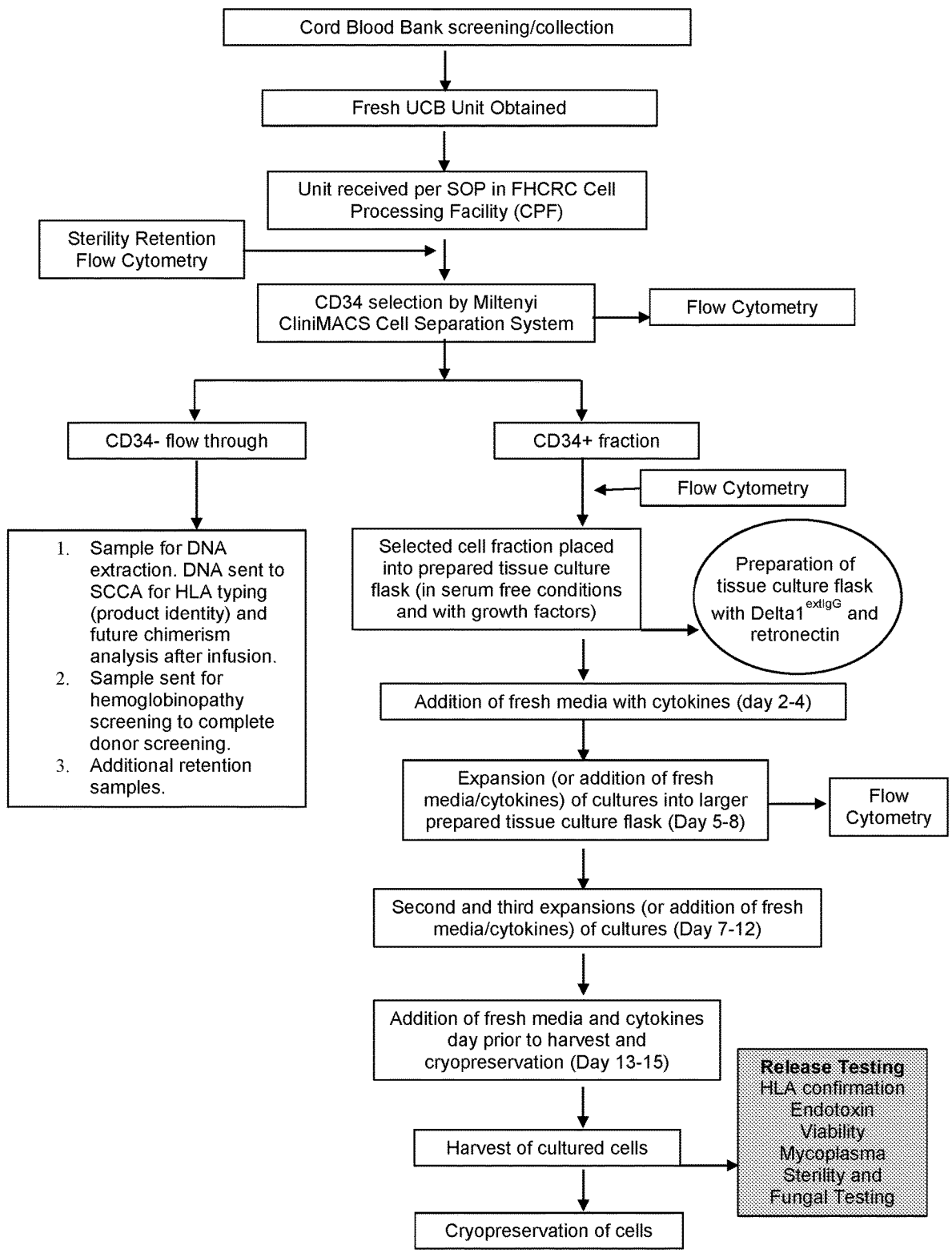
FIG. 1. Flowchart demonstrating an exemplary procedure for enriching a population of CD34+ cells, and expanding the enriched population.

US 2013/0095079 describes the development of a groundbreaking clinical product including CD34+ enriched and expanded human cord blood stem cells (Exp-CBSC) that could safely be administered to any patient without any degree of immunological matching between the patient and the clinical product. The Exp-CBSC were shown to decrease the time for immunosuppressed patients to recover immune function. For example, the Exp-CBSC helped chemotherapy patients recover immune function faster than they otherwise would have without the Exp-CBSC. The same effect was seen in patients who were severely immunocompromised to receive a cord blood transplant as a treatment for acute myelogenous leukemia (AML) and acute lymphoblastic leukemia (ALL). The Exp-CBSC similarly helped these cord blood transplant recipient patients recover immune function faster than they otherwise would have without the Exp-CBSC. The Exp-CBSC greatly improved patient outcomes following immune suppression by reducing infection, disease relapse, and other often fatal treatment complications due to reduced or absent immune function.

The current disclosure provides that the Exp-CBSC described in US 2013/0095079 have additional unanticipated clinical benefits in diverse patient populations. For example, the Exp-CBSC reduce transplant rejection, mucositis, total parental feeding, opioid use, and hospitalization following a medical procedure, and reduce graft versus host disease following an allogeneic transplant. These additional unanticipated clinical benefits of the Exp-CBSC in diverse patient populations also significantly improve patient outcomes. Reduced transplant rejection, mucositis, and graft versus host disease increases survival and quality of life following a solid tissue and/or allogeneic transplant. Reduced total parenteral feeding avoids the numerous complications that can arise due to such artificial feeding. Reducing patient exposure to opioid use can help address the on-going epidemic of pain killer abuse. Finally, reduced hospitalization following a medical procedure decreases costs associated with medical care and similarly reduces lost opportunity costs patients experience while hospitalized. Each of these uses and benefits is described more fully below. Individually and collectively they provide further evidence for the immense clinical benefits offered by the Exp-CBSC described in US 2013/0095079 in diverse patient populations.

Before describing the new uses of the Exp-CBSC, helpful definitions, methods to generate the Exp-CBSC, and their characteristics are provided for completeness.

Hematopoietic Stem Cells. The hematopoietic stem cell is pluripotent and ultimately gives rise to all types of terminally differentiated blood cells. The hematopoietic stem cell can self-renew, or it can differentiate into more committed progenitor cells, which progenitor cells are irreversibly determined to be ancestors of only a few types of blood cell. For instance, the hematopoietic stem cell can differentiate into (i) myeloid progenitor cells, which myeloid progenitor cells ultimately give rise to monocytes and macrophages, neutrophils, basophils, eosinophils, erythrocytes, megakaryocytes/platelets, dendritic cells, or (ii) lymphoid progenitor cells, which lymphoid progenitor cells ultimately give rise to T-cells, B-cells, and lymphocyte-like cells called natural killer cells (NK-cells). Once the stem cell differentiates into a myeloid progenitor cell, its progeny cannot give rise to cells of the lymphoid lineage, and, similarly, lymphoid progenitor cells cannot give rise to cells of the myeloid lineage. For a general discussion of hematopoiesis and hematopoietic stem cell differentiation, see Chapter 17, Differentiated Cells and the Maintenance of Tissues, Alberts et al., 1989, Molecular Biology of the Cell, 2nd Ed., Garland Publishing, New York, N.Y.; Chapter 2 of Regenerative Medicine, Department of Health and Human Services, August 2006, and Chapter 5 of Hematopoietic Stem Cells, 2009, Stem Cell Information, Department of Health and Human Services.

In vitro and in vivo assays have been developed to characterize hematopoietic stem cells, for example, the spleen colony forming (CFU-S) assay and reconstitution assays in immune-deficient mice. Further, presence or absence of cell surface protein markers defined by monoclonal antibody recognition have been used to recognize and isolate hematopoietic stem cells. Such markers include CD34, CD38, CD43, CD45RO, CD45RA, CD59, CD90, CD109, CD117, CD133, CD166, and HLA DR, and combinations thereof. See Chapter 2 of Regenerative Medicine, Department of Health and Human Services, August 2006 and the references cited therein.

Collecting Cord Blood. Human umbilical cord blood and/or human placental blood are sources of cord blood stem cells. Such blood can be obtained by any method known in the art. The use of cord or placental blood as a source of stem cells provides numerous advantages, including that the cord and placental blood can be obtained easily and without trauma to the donor. See, e.g., U.S. Pat. No. 5,004,681 for a discussion of collecting cord and placental blood at the birth of a human. In particular embodiments, cord blood collection is performed by the method disclosed in U.S. Pat. No. 7,147,626 B2 to Goodman et al. Collections should be made under sterile conditions. Immediately upon collection, cord or placental blood should be mixed with an anticoagulent. Such an anticoagulent can be any known in the art, including CPD (citrate-phosphate-dextrose), ACD (acid citrate-dextrose), Alsever's solution (Alsever et al., 1941, N.Y. St. J. Med. 41:126), De Gowin's Solution (De Gowin, et al., 1940, J. Am. Med. Ass. 114:850), Edglugate-Mg (Smith, et al., 1959, J. Thorac. Cardiovasc. Surg. 38:573), Rous-Turner Solution (Rous and Turner, 1916, J. Exp. Med. 23:219), other glucose mixtures, heparin, ethyl biscoumacetate, etc. See, generally, Hurn, 1968, Storage of Blood, Academic Press, New York, pp. 26-160). In particular embodiments, ACD can be used.

The cord blood can be obtained by direct drainage from the cord and/or by needle aspiration from the delivered placenta at the root and at distended veins. See, generally, U.S. Pat. No. 5,004,681.

In certain embodiments, the following tests on the collected blood sample can be performed either routinely, or where clinically indicated:
(i) Bacterial culture: To ensure the absence of microbial contamination, established assays can be performed, such as routine hospital cultures for bacteria under aerobic and anaerobic conditions.
(ii) Diagnostic screening for pathogenic microorganisms: To ensure the absence of specific pathogenic microorganisms, various diagnostic tests can be employed. Diagnostic screening for any of the numerous pathogens transmissible through blood can be done by standard procedures. As one example, the collected blood sample (or a maternal.cndot.blood sample) can be subjected to diagnostic screening for the presence of Human Immunodeficiency Virus-1 or 2 (HIV-1 or HIV-2). Any of numerous assay systems can be used, based on the detection of virions, viral-encoded proteins, HIV-specific nucleic acids, antibodies to HIV proteins, etc. The collected blood can also be tested for other infectious diseases, including human T-Cell lymphotropic virus I and II (HTLV-I and HTLV-II), Hepatitis B, Hepatitis C, Cytomegalovirus, Syphilis, West Nile Virus and other infectious agents as designated by relevant regulatory authorities such as the U.S. Food and Drug Administration.

Preferably, prior to collection of the cord blood, maternal health history is determined in order to identify risks that the cord blood cells might pose in transmitting genetic or infectious diseases, such as cancer, leukemia, immune disorders, neurological disorders, hepatitis or AIDS. The collected cord blood samples can undergo testing for one or more of cell viability, HLA typing, ABO/Rh typing, CD34+ cell count, and total nucleated cell count.

Enrichment of Cord Blood Stem Cells. Once the umbilical cord blood and/or placental blood is collected from a single human at birth, the blood is processed to produce an enriched hematopoietic stem cell population, or enriched hematopoietic stem and progenitor cell population, forming a population of cord blood stem cells. The hematopoietic stem cells, or hematopoietic stem and progenitor cells, can be positive for a specific marker expressed in increased levels on the hematopoietic stem cells or hematopoietic stem and progenitor cells, relative to other types of hematopoietic cells. For example, such markers can be CD34, CD43, CD45RO, CD45RA, CD59, CD90, CD109, CD117, CD133, CD166, HLA DR, or a combination thereof. The hematopoietic stem cells, or hematopoietic stem and progenitor cells, also can be negative for a specific marker, relative to other types of hematopoietic cells. For example, Lin is a combination of lineage-specific antibodies that serve as negative markers. CD38 also provides an example of a negative marker. Preferably, the hematopoietic stem cells, or hematopoietic stem and progenitor cells, are CD34+ cells. Preferably, the CB Stem Cell population is enriched in CD34+ stem cells or CD34+ stem and progenitor cells (and, thus, T cell depleted). Enrichment thus refers to a process wherein the percentage of hematopoietic stem cells, or hematopoietic stem and progenitor cells in the sample is increased (relative to the percentage in the sample before the enrichment procedure). Purification is one example of enrichment. In particular embodiments, the increase in the number of CD34+ cells (or other suitable antigen-positive cells) as a percentage of cells in the enriched sample, relative to the sample prior to the enrichment procedure, is 5-, 50-, 100-, 200-, 350-fold, or more. In particular embodiments, the CD34+ cells are enriched using a monoclonal antibody to CD34, which antibody is conjugated to a magnetic bead, and a magnetic cell separation device to separate out the CD34+ cells.

In particular embodiments, prior to processing for enrichment, the collected cord and/or placental blood is fresh and has not been previously cryopreserved.

Any technique known in the art for cell separation/selection can be used to carry out the enrichment for hematopoietic stem cells, or hematopoietic stem and progenitor cells. For example, methods which rely on differential expression of cell surface markers can be used. For example, cells expressing the cell surface marker CD34 can be positively selected using a monoclonal antibody to CD34, such that cells expressing CD34 are retained, and cells not expressing CD34 are not retained. Moreover, the separation techniques employed should maximize the viability of the cell to be selected. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation/selection include fluorescence activated cell sorters, which can have varying degrees of sophistication, e.g., a plurality of color channels, low angle and obtuse light scattering detecting channels, impedance channels, etc.

The antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the selected cells.

In particular embodiments, a fresh cord blood unit is processed to select for, i.e., enrich for, CD34+ cells using anti-CD34 antibodies directly or indirectly conjugated to magnetic particles in connection with a magnetic cell separator, for example, the CliniMACS® Cell Separation System (Miltenyi Biotec, Bergisch Gladbach, Germany), which employs nano-sized super-paramagnetic particles composed of iron oxide and dextran coupled to specific monoclonal antibodies. The CliniMACS® Cell Separator is a closed sterile system, outfitted with a single-use disposable tubing set. The disposable set can be used for and discarded after processing a single unit of collected cord and/or placental blood to enrich for CD34+ cells. Similarly, CD133+ cells can be enriched using anti-CD133 antibodies. In particular embodiments, CD34+ CD90+ cells are enriched for. Similarly, cells expressing CD43, CD45RO, CD45RA, CD59, CD90, CD109, CD117, CD166, HLA DR, or a combination of the foregoing, can be enriched for using antibodies against the target antigen.

In particular embodiments, one or more umbilical cord blood and/or placental blood samples can be pooled prior to enriching for the hematopoietic stem cells, or hematopoietic stem and progenitor cells. In particular embodiments, individual CB Stem Cell samples can be pooled after enriching for the hematopoietic stem cells, or hematopoietic stem and progenitor cells. In particular embodiments, the number of umbilical cord blood and/or placental blood samples, or CB Stem Cell samples, that are pooled is 2 or more (e.g., 2, 3, 7, 15, 35). In particular embodiments, the umbilical cord blood and/or placental blood samples or CB Stem Cell samples are pooled without regard to the HLA type of the cells that are present. In particular embodiments, without regard means that no steps are taken to determine the degree of HLA matching between the samples in the pool. In certain embodiments, the samples in the pool are derived from the umbilical cord blood and/or placental blood of individuals of the same race, e.g., African-American, Caucasian, Asian, Hispanic, Native-American, Australian Aboriginal, Inuit, Pacific Islander, or derived from umbilical cord blood and/or placental blood of individuals of the same ethnicity, e.g., Irish, Italian, Indian, Japanese, Chinese, Russian, etc.

Optionally, prior to enrichment for hematopoietic stem cells or hematopoietic stem and progenitor cells, the red blood cells and white blood cells of the cord blood can be separated. Once the separation of the red blood cells and the white blood cells has taken place, the red blood cell fraction can be discarded, and the white blood cell fraction can be processed in the magnetic cell separator as above. Separation of the white and red blood cell fractions can be performed by any method known in the art, including centrifugation techniques. Other separation methods that can be used include the use of commercially available products FICOLL™ or FICOLL-PAQUE™ or PERCOLL™ (GE Healthcare, Piscataway, N.J.). FICOLL-PAQUE™ is normally placed at the bottom of a conical tube, and the whole blood is layered above. After being centrifuged, the following layers will be visible in the conical tube, from top to bottom: plasma and other constituents, a layer of mononuclear cells called buffy coat containing the peripheral blood mononuclear cells (white blood cells), FICOLL-PAQUE™, and erythrocytes and granulocytes, which should be present in pellet form. This separation technique allows easy harvest of the peripheral blood mononuclear cells.

Optionally, prior to CD34+ cell selection, an aliquot of the fresh cord blood unit can be checked for total nucleated cell count and/or CD34+ content. In particular embodiments, after the CD34+ cell selection, both CD34+ ("CB Stem Cells") and CD34-cell fractions are recovered. Optionally, DNA can be extracted from a sample of the CD34-cell fraction for initial HLA typing and future chimerism studies, even though HLA matching to the patient is not done. The CD34+ enriched stem cell fraction ("CB Stem Cells") can be subsequently processed prior to expansion, for example, the stem cells can be suspended in an appropriate cell culture medium for transport or storage. In particular embodiments, the cell culture medium includes STEMSPAN™ Serum Free Expansion Medium (StemCell Technologies, Vancouver, British Columbia) supplemented with recombinant human Interleukin-3 (rhIL-3; e.g., 10 ng/ml or other concentrations described herein), recombinant human Interleukin-6 (rhIL-6; e.g., 50 ng/ml or other concentrations described herein), recombinant human Thrombopoietin (rhTPO; 50 ng/ml or other ranges described herein), recombinant human Flt-3 Ligand (rhFlt-3L; e.g., 50 ng/ml or other concentrations described herein), and recombinant human stem cell factor (rhSCF; e.g., 50 ng/ml or other concentrations described herein).

In particular embodiments, the umbilical cord blood and/or placental blood sample are red cell depleted, and the number of CD34+ cells in the red cell depleted fraction is calculated. In particular embodiments, the umbilical cord blood and/or placental blood samples containing more than 3.5 million CD34+ cells can be enriched by the enrichment methods described above, however, samples containing less than 3.5 million CD34+ cells may also be used.

Methods of Cord Blood Stem Cell Expansion. After the CB Stem Cells have been isolated from human cord blood and/or human placental blood collected from one or more humans at birth according to the enrichment methods described above or other methods known in the art, the CB Stem Cells are expanded in order to increase the number of hematopoietic stem cells or hematopoietic stem and progenitor cells, e.g., CD34+ cells. Any method known in the art for expanding the number of CB Stem Cells that gives rise to Expanded CB Stem Cell can be used. The CB Stem Cells can be cultured under cell growth conditions (e.g., promoting mitosis) such that the CB Stem Cells grow and divide (proliferate) to obtain a population of Expanded CB Stem Cells. In particular embodiments, individual populations of CB Stem Cells each derived from the umbilical cord blood and/or placental blood of a single human at birth can be pooled, without regard to the HLA type of the cells, prior to or after the expansion technique. In particular embodiments, the sample that is expanded is not a pool of samples. In particular embodiments, the technique used for expansion is one that has been shown to (i) result in an increase in the number of hematopoietic stem cells, or hematopoietic stem and progenitor cells, e.g., CD34+ cells, in the expanded sample relative to the unexpanded CB Stem Cell sample, and/or (ii) results in an increased number of SCID repopulating cells in the expanded sample determined by limiting-dilution analysis as shown by enhanced engraftment in NOD/SCID mice infused with the expanded sample, relative to that seen with the unexpanded sample, where the unexpanded sample and expanded sample are from different aliquots of the same sample, wherein the expanded sample but not the unexpanded sample is subjected to the expansion technique. In certain embodiments, the technique results in a 5-, 75-, 100-, 200-, 350-, or 500-fold or more increase in the number of hematopoietic stem cells or hematopoietic stem and progenitor cells in the expanded sample, relative to the unexpanded CB Stem Cell sample. The hematopoietic stem cells or hematopoietic stem and progenitor cells can be positive for one or more of CD34, CD43, CD45RO, CD45RA, CD59, CD90, CD109, CD117, CD133, CD166, and HLA DR and/or negative for Lin and/or CD38. In particular embodiments, enhanced engraftment can be detected by detecting an increased percentage of human CD45+ cells in the bone marrow of mice infused with an aliquot of the expanded sample relative to mice infused with an aliquot of the unexpanded sample at, e.g., 10 days, 3 weeks or 9 weeks post-infusion (see Delaney et al., 2010, Nature Med. 16(2): 232-236).

Such expansion techniques include those described in U.S. Pat. No. 7,399,633; Delaney et al., 2010, Nature Med. 16(2): 232-236; Zhang et al., 2008, Blood 111:3415-3423; and Himburg et al., 2010, Nature Med. 16, 475-482, as well as expansion utilizing aryl hydrocarbon receptor antagonists as described in WO/2013/086436), LILRB2 agonists as described in WO/2013/179633, and hydrogels (e.g., zwitterionic hydrogels), as well as those described below.

In particular embodiments, the CB Stem Cells are cultured with growth factors, and are exposed to cell growth conditions (e.g., promoting mitosis) such that the Stem Cells proliferate to obtain an Expanded CB Stem Cell population. In particular embodiments, the CB Stem Cells are cultured with an amount of an agonist of Notch function effective to inhibit differentiation, and are exposed to cell growth conditions (e.g., promoting mitosis) such that the CB Stem Cells proliferate to obtain an Expanded CB Stem Cell population. In particular embodiments, the CB Stem Cells are cultured with an amount of an agonist of Notch function effective to inhibit differentiation and in the presence of growth factors, and are exposed to cell growth conditions (e.g., promoting mitosis) such that the CB Stem Cells proliferate to obtain an Expanded CB Stem Cell population. The Expanded CB Stem Cell population so obtained can be frozen and stored for later use. Optionally, the Notch pathway agonist is inactivated or removed from the Expanded CB Stem Cell population prior to transplantation into the patient (e.g., by separation, dilution).

In specific embodiments, the CB Stem Cells are cultured for 2, 3, 4, 5, 6, 7, 8, 9, 10, 11, 12, 13, 14, 15, 16, 17, 18, 19, 20, 21, 22, 23, 24, or 25 days or more; or, in particular embodiments, the CB Stem Cells are cultured for at least 10 days.

Other exemplary culture condition for expanding CB Stem Cells are set forth in Zhang et al., 2008, Blood 111:3415-3423. In particular embodiments, the CB Stem Cells can be cultured in serum free medium supplemented with heparin, stem cell factor, thrombopoietin, insulin-like growth factor-2 (IGF-2), fibroblast growth factor-1 (FGF-1), and Angpt13 or Angpt15. In particular embodiments, the medium is supplemented with 10 µg/ml heparin, 10 ng/ml stem cell factor, 20 ng/ml thrombopoietin, 20 ng/ml IGF-2, 10 ng/ml FGF-1, and 100 ng/ml Angpt13 or Angpt15 and the cells are cultured for 19-23 days. In particular embodiments, the CB Stem Cells can be expanded by culturing the CB Stem Cells in serum free medium supplemented with 10 µg/ml heparin, 10 ng/ml stem cell factor, 20 ng/ml thrombopoietin, 10 ng/ml FGF-1, and 100 ng/ml Angpt15 for 11-19 days. In particular embodiments, the CB Stem Cells can be expanded by culturing the CB Stem Cells in serum free medium supplemented with 50 ng/ml stem cell factor, 10 ng/ml thrombopoietin, 50 ng/ml Flt-3 receptor ligand, and 100 ng/ml insulin-like growth factor binding protein-2 (IGFBP2) or 500 ng/ml Angpt15 for 10 days. In particular embodiments, the CB Stem Cells can be expanded by culturing the CB Stem Cells in serum free medium supplemented with 10 µg/ml heparin, 10 ng/ml stem cell factor, 20 ng/ml thrombopoietin, 10 ng/ml FGF-1, 500 ng/ml Angpt15, and 500 ng/ml IGFBP2 for 11 days. See Zhang et al., 2008, Blood 111:3415-3423.

Exemplary culture condition for expanding CB Stem Cells is set forth in Himburg et al., 2010, Nature Med., 16, 475-482. In particular embodiments, the CB Stem Cells can be cultured in liquid suspension culture supplemented with thrombopoietin, stem cell factor, Flt-3 receptor ligand, and pleiotrophin. In particular embodiments, the liquid suspension culture is supplemented with 20 ng/ml thrombopoietin, 125 ng/ml stem cell factor, 50 ng/ml Flt-3 receptor ligand, and 10, 100, 500, or 1000 ng/ml pleiotrophin and the CB Stem Cells are cultured for 7 days.

In particular embodiments, after expansion of the CB Stem Cells, the total number of cells and viable CD34+ cells are determined to measure the potency of the sample to provide hematopoietic function. Numerous clinical studies have shown that the total nucleated cell dose and the CD34+ cell dose in stem cell grafts are highly correlated with neutrophil and platelet engraftment as well as the incidence of graft failure and early transplant-related complications (primarily lethal infections) following stem cell transplantation. For example, at day 5-8 post culture initiation during expansion, a sample can be taken for determination of the total viable nucleated cell count. In addition, the total number of CD34+ cells can be determined by multi-parameter flow cytometry, and, thus, the percentage of CD34+ cells in the sample. Similarly, prior to cryopreservation or after thawing, an aliquot of the Expanded CB Stem Cell sample can be taken for determination of total nucleated cells and percentage of viable CD34+ cells in order to calculate the total viable CD34+ cell number in the Expanded CB Stem Cell sample.

In particular embodiments, total viable CD34+ (or other antigen-positive) cell numbers can be considered the potency assay for release of the final product for therapeutic use. Viability can be determined by any method known in the art, for example, by trypan blue exclusion or 7-AAD exclusion. In particular embodiments, the total nucleated cell count (TNC) and other data are used to calculate the potency of the product. The percentage of viable CD34+ cells can be assessed by flow cytometry and use of a stain that is excluded by viable cells. The percentage of viable CD34+ cells=the number of CD34+ cells that exclude 7-AAD (or other appropriate stain) in an aliquot of the sample divided by the TNC (both viable and non-viable) of the aliquot. Viable CD34+ cells in the sample can be calculated as follows: Viable CD34+ cells=TNC of sample x % viable CD34+ cells in the sample. The proportional increase during enrichment or expansion in viable CD34+ cells can be calculated as follows: Total Viable CD34+ cells Post-culture/Total Viable CD34+ cells Pre-culture. As will be apparent, antigens other than or in addition to CD34 can be used.

Notch Agonists. In particular embodiments, the CB Stem Cells are expanded by culturing the cells in the presence of an agonist of Notch function and one of more growth factors or cytokines for a given period of time. Culturing the CB Stem Cells can take place under any suitable culture medium/conditions known in the art (see, e.g., Freshney Culture of Animal Cells, Wiley-Liss, Inc., New York, N.Y. (1994)). The time in culture is for a time sufficient to produce an Expanded CB Stem Cell population, as defined herein. For example, the CB Stem Cells can be cultured in a serum-free medium in the presence of an agonist of Notch function and one or more growth factors or cytokines for 2, 3, 4, 5, 6, 7, 8, 9, 10, 11, 12, 13, 14, 15, 16, 17, 18, 19, 20, 21, 22, 23, 24, or 25 days; or, in particular embodiments, for at least 10 days. Optionally, at any point during the culturing period, the culture medium can be replaced with fresh medium or fresh medium can be added.

A Notch agonist is an agent that promotes, i.e., causes or increases, activation of Notch pathway function. As used herein, "Notch pathway function" shall mean a function mediated by the Notch signaling (signal transduction) pathway, including nuclear translocation of the intracellular domain of Notch, nuclear translocation of RBP-Jκ or its Drosophila homolog Suppressor of Hairless; activation of bHLH genes of the Enhancer of Split complex, e.g., Mastermind; activation of the HES-1 gene or the KBF2 (also called CBF 1) gene; inhibition of Drosophila neuroblast segregation; and binding of Notch to Delta, Jagged/Serrate, Fringe, Deltex or RBP-Jκ/Suppressor of Hairless, or homologs or analogs thereof. See generally the review article by Kopan et al., 2009, Cell 137:216-233 for a discussion of the Notch signal transduction pathway and its effects upon activation; see also Jarriault et al., 1998, Mol. Cell. Biol. 18:7423-7431.

Notch activation is carried out by exposing a cell to a Notch agonist. The agonist of Notch can be a soluble molecule, a molecule that is recombinantly expressed on a cell-surface, a molecule on a cell monolayer to which the precursor cells are exposed, or a molecule immobilized on a solid phase. Exemplary Notch agonists are the extracellular binding ligands Delta and Serrate which bind to the extracellular domain of Notch and activate Notch signal transduction, or a fragment of Delta or Serrate that binds to the extracellular domain of Notch and activates Notch signal transduction. Nucleic acid and amino acid sequences of Delta and Serrate have been isolated from several species, including human, are known in the art, and are disclosed in International Patent Publication Nos. WO 93/12141, WO 96/27610, WO 97/01571, Gray et al., 1999, Am. J. Path. 154:785-794. In particular embodiments, the Notch agonist is an immobilized fragment of a Delta or Serrate protein including the extracellular domain of the protein fused to a myc epitope tag (Delta$^{ext-myc}$ or Serrate$^{ext-myc}$, respectively) or an immobilized fragment of a Delta or Serrate protein including the extracellular domain of the protein fused to the Fc portion of IgG (Delta$^{ext-IgG}$ or Serrate$^{ext-IgG}$, respectively). Notch agonists include Notch proteins and analogs and derivatives (including fragments) thereof; proteins that are other elements of the Notch pathway and analogs and derivatives (including fragments) thereof; antibodies thereto and fragments or other derivatives of such antibodies containing the binding region thereof; nucleic acids encoding the proteins and derivatives or analogs; as well as proteins and derivatives and analogs thereof which bind to or otherwise interact with Notch proteins or other proteins in the Notch pathway such that Notch pathway activity is promoted. Such agonists include Notch proteins and derivatives thereof including the intracellular domain, Notch nucleic acids encoding the foregoing, and proteins including the Notch-interacting domain of Notch ligands (e.g., the extracellular domain of Delta or Serrate). Other agonists include RBPR/Suppressor of Hairless or Deltex. Fringe can be used to enhance Notch activity, for example in conjunction with Delta protein. These proteins, fragments and derivatives thereof can be recombinantly expressed and isolated or can be chemically synthesized.

In particular embodiments, the Notch agonist is a cell which recombinantly expresses a protein or fragment or derivative thereof, which agonizes Notch. The cell expresses the Notch agonist in such a manner that it is made available to the CB Stem Cells in which Notch signal transduction is to be activated, e.g., it is secreted, expressed on the cell surface, etc.

In particular embodiments, the agonist of Notch is a peptidomimetic or peptide analog or organic molecule that binds to a member of the Notch signaling pathway. Such an agonist can be identified by binding assays selected from those known in the art, for example the cell aggregation assays described in Rebay et al., 1991, Cell 67:687-699 and in International Patent Publication No. WO 92/19734.

In particular embodiments, the agonist is a protein including at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes, as used herein, shall mean the genes Notch, Delta, Serrate, RBPJκ, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in Drosophila). Exemplary fragments of Notch-binding proteins containing the region responsible for binding to Notch are described in U.S. Pat. Nos. 5,648,464; 5,849,869; and 5,856,441.

Notch agonists can be obtained commercially, produced by recombinant expression, or chemically synthesized.

In particular embodiments, exposure of the cells to a Notch agonist is not done by incubation with other cells recombinantly expressing a Notch ligand on the cell surface (although in other embodiments, this method can be used), but rather is by exposure to a cell-free Notch ligand, e.g., incubation with a cell-free ligand of Notch, which ligand is immobilized on the surface of a solid phase, e.g., immobilized on the surface of a tissue culture dish.

In specific embodiments, Notch activity is promoted by the binding of Notch ligands (e.g., Delta, Serrate) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate molecules, including the extracellular domains of the proteins or Notch-binding portions thereof, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which Delta or Serrate is expressed as a fusion protein (e.g., a myc epitope tag, which is recognized by the antibody 9E10) or a protein which interacts with an epitope tag with which Delta or Serrate is expressed as a fusion protein (e.g., an immunoglobulin epitope tag, which is bound by Protein A).

In particular embodiments, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway, for example molecules that trigger the dissociation of the Notch ankyrin repeats with RBP-Jκ, thereby promoting the translocation of RBP-Jκ from the cytoplasm to the nucleus.

Growth Factors/Cytokines. In particular embodiments, the CB Stem Cells are expanded by culturing the cells in the presence of an agonist of Notch function and one of more growth factors or cytokines for a given period of time. Alternatively, the CB Stem Cells are expanded by culturing the cells in the presence of one of more growth factors or cytokines for a given period of time. Wherein expansion of the CB Stem Cells without differentiation is to be achieved, the CB Stem Cells are cultured in the presence of growth factors that support growth but not differentiation. The growth factor can be any type of molecule, such as a protein or a chemical compound, that promotes cellular proliferation and/or survival.

Exposing the CB Stem Cells to one or more growth factors can be done prior to, concurrently with, or following exposure of the cells to a Notch agonist. In specific exemplary embodiments, the growth factors present in the expansion medium include one or more of the following growth factors: stem cell factor (SCF), also known as the c-kit ligand or mast cell growth factor, Flt-3 ligand (Flt-3L), interleukin-6 (IL-6), interleukin-3 (IL-3), interleukin-11 (IL-11) and thrombopoietin (TPO), granulocyte-macrophage colony stimulating factor (GM-CSF), granulocyte colony stimulating factor (G-CSF), angiopoietin-like proteins (Angptls) (Angptl2, Angptl3, Angptl5, Angptl7, and Mfap4), insulin growth factor-2 (IFG-2), fibroblast growth factor-1 (FGF-1). The amount of SCF, Flt-3L, IL-6, or TPO can be in the range of 10-1000 ng/ml, in particular embodiments, 50-500 ng/ml, and in particular embodiments 100-300 ng/ml. In particular embodiments, the amount of SCF, Flt-3L, IL-6, or TPO is 100, 125, 150, 175, 200, 225, 250, 275, 300, 325, 350, 375, 400, 425 or 450 ng/ml. The amount of 1L-3, IL-11, G-CSF, or GM-CSF can be in the range of 2-100 ng/ml, in particular embodiments, 5-50 ng/ml, and in particular embodiments 7.5-25 ng/ml, and in particular embodiments 10-15 ng/ml. In particular embodiments, the amount of 1L-3, IL-11, G-CSF, or GM-CSF is 5, 6, 7, 8, 9, 10, 12.5, or 15 ng/ml.

In particular embodiments, for expanding CB Stem Cells, the cells are cultured in a tissue culture dish onto which an extracellular matrix protein is bound. In particular embodiments, the extracellular matrix protein is fibronectin (FN), or a fragment thereof. Such a fragment can be CH-296 (Dao et al., 1998, Blood 92(12):4612-21) or RetroNectin® (a recombinant human fibronectin fragment) (Clontech Laboratories, Inc., Madison, Wis.).

In particular embodiments for expanding CB Stem Cells, the cells are cultured on a plastic tissue culture dish containing immobilized Delta ligand, e.g., the extracellular domain of Delta, and fibronectin in the presence of 100 ng/ml of each of SCF and TPO, and 10 ng/ml GM-CSF. In particular embodiments, for expanding CB Stem Cells, the cells are cultured on a plastic tissue culture dish containing immobilized Delta ligand and fibronectin in the presence of 100 ng/ml of each of SCF, Flt-3L, TPO and IL-6 and 10 ng/ml of IL-3. In particular embodiments, for expanding Stem Cells, the cells are cultured on a plastic tissue culture dish containing immobilized Delta ligand and fibronectin in the presence of 100 ng/ml of each of SCF and Flt-3L and 10 mg/ml of each of G-CSF and GM-CSF. In particular embodiments, for expanding CB Stem Cells, the cells are cultured on a plastic tissue culture dish containing immobilized Delta ligand and fibronectin in the presence of 100 ng/ml of each of SCF, Flt-3L and TPO and 10 mg/ml of GM-CSF. In particular embodiments, for expanding CB Stem Cells, the cells are cultured on a plastic tissue culture dish containing immobilized Delta ligand and fibronectin in the presence of 300 ng/ml of each of SCF and Flt-3L, 100 ng/ml of each of TPO and IL-6, and 10 mg/ml of IL-3. In particular embodiments, for expanding CB Stem Cells, the cells are cultured on a plastic tissue culture dish containing immobilized Delta ligand and fibronectin in the presence of 100 ng/ml of each of SCF, Flt-3L, and TPO and 10 mg/ml of each of G-CSF and GM-CSF. In particular embodiments, fibronectin is excluded from the tissue culture dishes or is replaced by another extracellular matrix protein. See also U.S. Pat. No. 7,399,633 B2 to Bernstein et al. for additional exemplary culture conditions for CB Stem Cell expansion.

The growth factors can be obtained commercially, produced by recombinant expression, or chemically synthesized. For example, Flt-3L (human), IGF-1 (human), IL-6 (human and mouse), IL-11 (human), SCF (human), TPO (human and murine) can be purchased from Sigma (St. Louis, Mo.). IL-6 (human and murine), IL-7 (human and murine), and SCF (human) can be purchased from Life Technologies, Inc. (Rockville, Md.).

In other embodiments, the growth factors are produced by recombinant expression or by chemical peptide synthesis (e.g. by a peptide synthesizer). Growth factor nucleic acid and peptide sequences are generally available from GenBank.

In particular embodiments, the growth factor(s) used to expand the CB Stem Cells in the presence of a Notch agonist is derived from the same species as the CB Stem Cells.

The amount or concentration of growth factors suitable for expanding the CB Stem Cells will depend on the activity of the growth factor preparation, and the species correspondence between the growth factors and the CB Stem Cells, etc. Generally, when the growth factor(s) and the CB Stem Cells are of the same species, the total amount of growth factor in the culture medium ranges from 1 ng/ml to 5 µg/ml, in particular embodiments, from 5 ng/ml to 1 µg/ml, and in particular embodiments, from 10 ng/ml to 200 ng/ml. In particular embodiments, the CB Stem Cells are expanded by exposing the CB Stem Cells to a Notch agonist and 100 ng/ml of SCF. In particular embodiments, the CB Stem Cells are expanded by exposing the CB Stem Cells to a Notch agonist and 100 ng/ml of each of Flt-3L, IL-6 and SCF and 10 ng/ml of IL-11.

Cryopreservation and Thawing Cryopreservation. Once the Expanded CB Stem Cell population is obtained after expanding CB Stem Cells from cord blood, the Expanded CB Stem Cell population can be cryopreserved. In particular embodiments, an Expanded CB Stem Cell population can be divided and frozen in one or more bags (or units). In particular embodiments, two or more Expanded CB Stem Cell populations can be pooled, divided into separate aliquots, and each aliquot is frozen. In particular embodiments, the Expanded CB Stem Cells are fresh, i.e., they have not been previously frozen prior to expansion or cryopreservation. The terms "frozen/freezing" and "cryopreserved/cryopreserving" are used interchangeably in the present application. Cryopreservation can be by any method known in the art that freezes cells in viable form. The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroy the cell. For a discussion, see Mazur, P., 1977, Cryobiology 14:251-272.

These injurious effects can be circumvented by (a) use of a cryoprotective agent, (b) control of the freezing rate, and (c) storage at a temperature sufficiently low to minimize degradative reactions.

Cryoprotective agents which can be used include dimethyl sulfoxide (DMSO) (Lovelock and Bishop, 1959, Nature 183:1394-1395; Ashwood-Smith, 1961, Nature 190: 1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In particular embodiments, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO.

A controlled slow cooling rate can be critical. Different cryoprotective agents (Rapatz et al., 1968, Cryobiology 5(1):18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1):17-32; and Mazur, 1970, Science 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1° to 3° C./minute from 0° C. to −80° C. In particular embodiments, this cooling rate can be used for the neonatal cells. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 ml) can be frozen in polyolefin bags (e.g., Dehned) held between metal plates for better heat transfer during cooling. Bags of bone marrow cells have been successfully frozen by placing them in −80° C. freezers which, fortuitously, gives a cooling rate of 3° C./minute).

In particular embodiments, the methanol bath method of cooling can be used. The methanol bath method is well-suited to routine cryopreservation of multiple small items on a large scale. The method does not require manual control of the freezing rate nor a recorder to monitor the rate. In particular embodiments, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, the Expanded CB Stem Cells can be transferred to a long-term cryogenic storage vessel. In particular embodiments, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Suitable racking systems are commercially available and can be used for cataloguing, storage, and retrieval of individual specimens.

Considerations and procedures for the manipulation, cryopreservation, and long-term storage of the hematopoietic stem cells, particularly from bone marrow or peripheral blood, are largely applicable to the Expanded CB Stem Cells. Such a discussion can be found, for example, in the following references, incorporated by reference herein: Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and envisioned for use (e.g., cold metal-mirror techniques; Livesey and Linner, 1987, Nature 327:255; Linner et al., 1986, J. Histochem. Cytochem. 34(9):1123-1135; see also U.S. Pat. No. 4,199, 022 by Senkan et al., U.S. Pat. No. 3,753,357 by Schwartz, U.S. Pat. No. 4,559,298 by Fahy).

Thawing. Frozen cells are preferably thawed quickly (e.g., in a water bath maintained at 37°-41° C.) and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In particular embodiments, the Expanded CB Stem Cell sample as thawed, or a portion thereof, can be infused for providing hematopoietic function in a human patient in need thereof. Several procedures, relating to processing of the thawed cells are available, and can be employed if deemed desirable.

The cryoprotective agent, if toxic in humans, should be removed prior to therapeutic use of the thawed Expanded CB Stem Cells. In embodiments employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, 1977, Biochemical Methods in Cell Culture and Virology, Dowden, Hutchinson & Ross, Stroudsburg, Pa., pp. 18-19; 1964, Methods in Medical Research, Eisen et al., eds., Vol. 10, Year Book Medical Publishers, Inc., Chicago, pp. 39-47) can be done to confirm cell survival. The percentage of viable antigen (e.g., CD34) positive cells in a sample can be determined by calculating the number of antigen positive cells that exclude 7-AAD (or other suitable dye excluded by viable cells) in an aliquot of the sample, divided by the total number of nucleated cells (TNC) (both viable and non-viable) in the aliquot of the sample. The number of viable antigen positive cells in the sample can be then determined by multiplying the percentage of viable antigen positive cells by TNC of the sample.

Prior to cryopreservation and/or after thawing, the total number of nucleated cells, or in particular embodiments, the total number of CD34+ or CD133+ cells can be determined. For example, total nucleated cell count can be performed by using a hemocytometer and exclusion of trypan blue dye. Specimens that are of high cellularity can be diluted to a concentration range appropriate for manual counting. Final cell counts for products are corrected for any dilution factors. Total nucleated cell count=viable nucleated cells per mL×volume of product in mL. The number of CD34+ or CD133+ positive cells in the sample can be determined, e.g., by the use of flow cytometry using anti-CD34 or anti-CD133 monoclonal antibodies conjugated to a fluorochrome.

In certain embodiments, the identity and purity of the starting umbilical cord blood and/or placental blood, the CB Stem Cells, and the Expanded CB Stem Cells prior to cryopreservation, or the Expanded CB Stem Cells after thawing can be subjected to multi-parameter flow cytometric immunophenotyping, which provides the percentage of viable antigen positive cells present in a sample. Each sample can be tested for one or more of the following cell phenotypes using a panel of monoclonal antibodies directly conjugated to fluorochromes: 1. CD34+ HPC; 2. T cells (CD3+, including both CD4+ and CD8+ subsets; 3. B cells (CD 19+ or CD20+); 4. NK cells (CD56+); 5. Monocytes (CD14+); 6. Myelomonocytes (CD 15+); 7. Megakaryocytes (CD41+); 8. Dendritic Cells (lineage negative/HLA-DRbright and CD123bright, or lineage negative/HLA-DRbright and CD11cbright).

The following provides a specific exemplary protocol based on the methods just described. Umbilical cord blood/placental blood unit(s) can be collected from a single human at birth. The collected blood can then be mixed with an anti-coagulant to prevent clotting. The blood can be stored under quarantine at 4° C. in a monitored refrigerator. The received unit(s) can be assessed, and which unit(s) will be processed for expansion can be determined. The following information can be collected on the units: date received, age in hours of the unit, gestational age of the donor in weeks, sex of the donor, and volume of the unit. Further, total nucleated cell count and total CD34+ cell count of each unit can be determined and percent CD34+ cells can be calculated. When a unit is selected for expansion, it can be removed from quarantine and assigned a unique Lot Number identifier, which it can retain throughout the manufacturing process.

Prior to planned initiation of expansion cultures, tissue culture vessels can be first coated overnight at 4° C. or a minimum of 2 hours at 37° C. with Delta1$^{ext-IgG}$ at 2.5 µg/ml and RetroNectin® (a recombinant human fibronectin fragment) (Clontech Laboratories, Inc., Madison, Wis.) at 5 µg/ml in phosphate buffered saline (PBS). The flasks can then be washed with PBS and blocked with PBS-2% Human Serum Albumin (HSA). The fresh cord blood unit can be processed to select for CD34+ cells using the CliniMACS® Plus Cell Separation System. Prior to CD34 selection, an aliquot of the fresh cord blood unit can be checked for total cell count and CD34 content. Both CD34+ and CD34− cell fractions can be recovered after processing. After enrichment according to this procedure, the percentage of CD34+ cells in the sample generally increases by 88- to 223-fold relative to the percentage of CD34+ cells in the sample prior to enrichment. The enriched CD34+ cell fraction can be resuspended in final culture media, which includes STEM-SPAN™ Serum Free Expansion Medium (StemCell Technologies, Vancouver, British Columbia) supplemented with rhIL-3 (10 ng/ml), rhIL-6 (50 ng/ml), rhTPO (50 ng/ml), rhFlt-3L (50 ng/ml), rhSCF (50 ng/ml).

The CD34+ enriched cells can be added to the specifically labeled and prepared tissue culture vessels (e.g., at a concentration of $1.8×10^4$ total nucleated cells/cm$^2$) of vessel surface area, and then placed into individually monitored and alarmed incubators dedicated solely to that lot of product. After 2-4 days of culture, 50% of the original volume of fresh culture media (as above) can be added to the vessels. The cell culture vessels can be removed from the incubator periodically (every 1-3 days), and examined by inverted microscope for cell growth and signs of contamination. On day 5-8, the vessel can be gently agitated to mix the cells, and a 1 ml sample can be removed for in process testing. The sample of cells can be counted and phenotyped for expression of CD34, CD7, CD14, CD15 and CD56. Throughout the culture period, cells can be transferred to additional flasks as needed when cell density increases to $≥8×10^5$ cells/ml. On the day prior to harvesting the cells for cryopreservation, fresh media can be added.

On day 14-16, the expanded cell population can be harvested for cryopreservation. The vessels can be agitated and the entire contents transferred to sterile 500 ml centrifuge tubes. The harvested cells can be centrifuged and then washed one time by centrifugation in PBS and resuspended in a cryoprotectant solution containing HSA, Normosol-R (Hospira, Lake Forrest, Ill.) and Dimethylsulfoxide (DMSO). Samples for completion of release testing can be taken. The Expanded CB Stem cell population product can be frozen in a controlled-rate freezer and transferred to storage in a vapor-phase liquid nitrogen (LN2) freezer.

At the end of the culture period, the resulting cell population should be heterogeneous, including CD34+ progenitor cells and more mature myeloid and lymphoid precursors, as evidenced by flow cytometric analysis for the presence of CD34, CD7, CD14, CD 15 and CD56 antigens. Typical flow cytometry characterization of cells expanded by this process at the end of the expansion period are presented in FIG. 2.

There should be a significant increase of CD34+ and total cell numbers during the culture period, ranging from 100 to 387 fold expansion of CD34+ cells and 617 to 3337 fold expansion of total cell numbers (N=9 individual cord blood units, processed per the final clinical expansion procedures as described above). There should be essentially a complete lack of T cells as measured by immunophenotyping. Functionally, the cells are capable of multi-lineage human hematopoietic engraftment in a NOD/SCID mouse model.

FIG. 3 shows data from ten full-scale ex vivo expansions performed according to this protocol. The average fold expansion for total cell numbers was 1723±230 (mean±sem) and for CD34+ cells was 179±30 (mean±sem). FIG. 4 sets forth the starting, ending and fold expansion numbers for total nucleated cells and CD34+ cells post-expansion for 19 full scale ex vivo expansions. These 19 expanded human cord blood stem cells were cryopreserved in one or more bags. FIG. 5 sets forth total nucleated cell (TNC) and CD34+ cell counts for each of the expanded human cord blood stem cell sample and cell viability prior to cryopreservation, and TNC and CD34+ cell counts in each frozen bag. Further, an additional 12 samples of enriched CD34+ cells were expanded with Delta1$^{ext-IgG}$, and showed an average 141-fold expansion (SEM 17) of CD34+ cells, prior to cryopresevation.

Following the foregoing description, it is now helpful to provide the following definition of terms:

"CB Stem Cells," referred to herein interchangeably as "a CB Stem Cell Sample," refers to a population enriched in hematopoietic stem cells, or enriched in hematopoietic stem and progenitor cells, derived from human umbilical cord blood and/or human placental blood collected at birth. The hematopoietic stem cells, or hematopoietic stem and progenitor cells, can be positive for a specific marker expressed in increased levels on hematopoietic stem cells or hematopoietic stem and progenitor cells, relative to other types of hematopoietic cells. For example, such markers can be CD34, CD43, CD45RO, CD45RA, CD59, CD90, CD109, CD117, CD133, CD166, HLA DR, or a combination thereof. Also, the hematopoietic stem cells, or hematopoietic stem and progenitor cells, can be negative for an expressed marker, relative to other types of hematopoietic cells. For example, such markers can be Lin, CD38, or a combination thereof. In particular embodiments, the hematopoietic stem cells, or hematopoietic stem and progenitor cells, are CD34+ cells.

"Expanded CB Stem Cells," referred to herein interchangeably as "an Expanded CB Stem Cell Sample," and "Ex-CBSC" refer to CB Stem Cells that have been subjected to a technique for expanding the cord blood hematopoietic stem cells, or hematopoietic stem and progenitor cells, which technique has been shown to result in (i) an increase in the number of hematopoietic stem cells, or hematopoietic stem and progenitor cells, in an aliquot of the sample thus expanded, and/or (ii) an increased number of SCID repopulating cells determined by limiting-dilution analysis as shown by enhanced engraftment in NOD/SCID mice infused with an aliquot of the sample thus expanded; relative to that seen with an aliquot of the sample that is not subjected to the expansion technique. In particular embodiments, the enhanced engraftment in NOD/SCID mice can be detected by detecting an increased percentage of human CD45+ cells in the bone marrow of mice infused with an aliquot of the expanded sample relative to mice infused with an aliquot of the sample prior to expansion, at, e.g., 10 days, 3 weeks or 9 weeks post-infusion (see Delaney et al., 2010, Nature Med. 16(2): 232-236). In particular embodiments, the expansion technique results in an at least 50-, 75-, 100-, 150-, 200-, 250-, 300-, 350-, 400-, 450-, or 500-fold increase in the number of hematopoietic stem cells or hematopoietic stem and progenitor cells, in an aliquot of the sample expanded, and in particular embodiments, is at least a 100 fold increase.

Use of Ex-CBSC for Reduced Solid Tissue Transplant Rejection. There are many diseases and conditions that culminate in organ dysfunction or failure. Under certain conditions, the best therapeutic option for treatment of organ dysfunction or failure is organ transplantation. Additionally, organ transplant can benefit or even be life-saving for individuals who have experienced a traumatic or degenerative event. For example, burn and/or crash victims can benefit from skin grafts. Even face transplants are entering the clinical realm.

Major histocompatibility complex (MHC) molecules (human leukocyte antigens (HLA) in humans) exist on the surfaces of cells and the particular structures of these molecules are typically unique for each individual (with the exception of identical twins).

HLA class I antigens (HLA-A, HLA-B and HLA-C) are transmembrane proteins that are expressed on the surface of almost all the cells of the body (except for red blood cells and the cells of the central nervous system) and present peptides on the cell surface, which peptides are produced from digested proteins that are broken down in the proteasomes.

HLA class II antigens (HLA-DP, HLA-DM, HLA-DOA, HLA-DOB, HLA-DQ, and HLA-DR) present antigens from outside of the cell to T-lymphocytes. These particular antigens stimulate T-helper cells to multiply, and these T-helper cells then stimulate antibody-producing B-cells to produce antibodies to that specific antigen. Self-antigens are suppressed by suppressor T-cells.

HLA class III antigens encode components of the complement system.

Diversity of HLA in the human population is one aspect of disease defense, and, as a result, the chance of two unrelated individuals having identical HLA molecules on all loci is very low. Thus, there is a need for HLA typing to determine suitable allele matching to avoid rejection of donor tissue by the recipient. Most tissue typing (e.g., for immunological matching to a recipient) is done using serological methods with antibodies specific for identified HLA antigens. DNA-based methods for detecting polymorphisms in the HLA antigen-encoding gene are also used for typing HLA alleles, and are rapidly becoming the preferred method for HLA typing. HLA typing can be done (1) by determining the HLA allele, which is done on the DNA sequence level by determining the allele-specific sequences (high resolution typing), and/or (2) by determining the HLA antigen serologically, by way of antibodies specific for the HLA-antigen (low resolution typing).

Each individual's immune system is programmed to attack foreign or "non-self" MHC- or HLA-bearing tissues. Because of this, one challenge to therapeutic transplantation is the damaging effects of the recipient (host's) immune system on the transplant. If these damaging effects are not managed, transplant rejection can occur which can be fatal when, for example, a vital organ is rejected. Thus, as used herein transplant rejection refers to rejection of solid tissue transplanted material (e.g., an organ, a group of cells (e.g. islet beta cells), a skin graft, or hair) by the immune system of the recipient/host. In particular embodiments, transplant rejection means an occurrence of more than 80% or 90% cell or tissue necrosis of the transplanted material as a result of the recipient/host's immune response against the transplanted material. In particular embodiments, transplant rejection means a decrease in the viability of transplanted material such that the intended function of the transplanted material is decreased by 80% or 90% or more as compared to the viability of the transplanted material prior to transplantation as a result of the recipient/host's immune response against the transplanted material.

Due to the risk of transplant rejection, an effort is made to optimize the degree of MHC/HLA matching between donor and recipient. Here, it is helpful to clarify the distinction between matched/mismatched transplants and unmatched or non-matched transplants as the terms are used herein. Immunological matching that refers to "matched" or "mismatched" refers to a degree of matching. For example, when 6 HLA antigens are typed and matched, a sample could be said to be matched at 4/6; 5/6; or 6/6 HLA antigens. The 4/6 and 5/6 same samples could also be said to be "mismatched" at 2/6 or 1/6 HLA antigens. In both instances, there is a high degree of matching between the donor and recipient (>50% matched). Conversely, "without matching", "unmatched" or "non-matched" means that the degree of matching between a donor and a recipient is unknown because, for example, neither the donor nor recipient was HLA-typed.

In transplant medicine, the highest degree of immunological matching possible between donor and recipient is preferred. This is because a high degree of matching generally reduces the magnitude of the recipient's rejection response. Medications to suppress the recipient/host's immune response against the transplant can also be used. Examples of such immuno-suppressants ("antirejection drugs") include prednisone, cyclosporine A, and cyclophosphamide.

Despite advances in the ability to perform transplants, transplant maintenance remains a challenge. For example, immunosuppression to prevent transplant rejection enhances the risk for opportunistic infections and cancer. Therefore, there is a need for more effective anti-rejection medical treatments that prolong transplant (and thus patient) survival and improve quality of life.

The present disclosure provides that administration of Ex-CBSC reduces transplant rejection. More particularly, and as shown in Example 1, administration of Ex-CBSC significantly reduces transplant rejections as demonstrated through prolonged maintenance of skin grafts. The ability of the Ex-CBSC to reduce rejection of allogeneic skin grafts demonstrates that the Ex-CBSC will also reduce rejection of other types of solid tissues as well. This is because maintenance of skin grafts is particularly difficult and thus these types of grafts have become the "gold standard" for experimental transplant research (Anderson & Matzinger, Nat. Med. 2001. (7)1: 80-87). A predominant mechanism responsible for solid tissue rejection across all tissue types is T cell activation caused by non-self, donor-derived peptides presented by MHC molecules. A subset of T cells that respond to non-self, donor-derived antigens become memory T cells, which will subsequently prevent development of a regulatory immune response to the donor tissue. Memory T cells are an important determinant of rejection of skin grafts (Benichou et al. Immunotherapy. 2011. 3(6): 757-770), as well as other organ types, such as liver (Donckier et al. Tranplantation. 2013. 96(3):306-15), heart (Azzawi, J Heart Lung Transplant. 1998. 17:881-887) and kidney (Heeger, J Immunol. 1999: 163:2267-2275). Without being bound by theory, one reason the Ex-CBSC induce tolerance to skin grafts is because they promote activity of donor-specific regulatory T cells by depleting secondary lymph tissue of donors-specific memory T cells upon expansion of the Ex-CBSC. Suppression of donor-specific memory T cells and enhancement of regulatory T cells can promote tolerance of many organ types. Therefore, the Ex-CBSC will be useful for preventing rejection of many types of solid organs and tissues.

Further, Example 1 also indicates that the reduced solid tissue rejection can be attributed to immune tolerance. In this context, immune tolerance refers to a decrease in the intensity of an immune response by the host against transplanted material. In particular embodiments, the intensity of an immune response can be decreased by 5-100%, 25-100% or 75-100% as compared to the average host immune response against transplant material that have not received Ex-CBSC as disclosed herein. In particular embodiments, the intensity of an immune response can be measured by determining the time point at which transplanted material is rejected. For example, immune tolerance can allow the transplanted material to survive and function for a longer period of time. In particular embodiments, immune tolerance can refer to a state of the immune system (host) in which certain foreign antigens do not elicit or elicit a reduced immune response.

Based on the foregoing, the Ex-CBSC can be used to induce immune tolerance in diverse patient populations and contexts. Thus, particular embodiments disclosed herein include administering Ex-CBSC to render a subject immune tolerant to a transplant. A subject that is immune tolerant fails to mount an immune response that significantly rejects or destroys transplanted material. In particular embodiments, a subject that is immune tolerant does not respond to an antigen by producing antibodies capable of binding to the antigen, or responds at level that is reduced by a statistically-significant degree and/or by a degree of clinical significance.

In particular embodiments, the current disclosure provides administration of Exp-CBSC to reduce transplant rejection of adipose tissue, blood vessels, bone, bone marrow, cardiac cells, cartilage, cartilaginous cells, chondral cells, cochlea, connective tissue, corneas, cultured cell monolayers, dental tissues, eye, face, fascia, fibrous tissue, foot, functional spine unit, hair, hand, heart, heart valves, intestine, islet cells, kidney, lenses, ligaments, liver, lung, meniscus, muscle-tendon grafts, muscle tissue, neural cells, neural tissue, osteochondral cells, osteogenic cells, ovary, pancreas, semi-tendinous tissues, skin, spleen, stem cells, stomach, tendons, testis, tooth or teeth, and vertebral discs.

As indicated previously, the beneficial effects of the Ex-CBSC in reducing transplant rejection can reduce the need for immune suppression in patients receiving transplants. Thus, following administration of Ex-CBSC, patients may be administered less immuno-suppressants. Exemplary immuno-suppressants include cyclosporin, cyclosporine A, cyclophosphamide, prednisone, dexamethasone, methotrexate, azathioprine, mycophenolate mofetil, thalidomide, FK-506 (tacrolimus), sirolimus, systemic steroids, topical steroids as well as a broad range of antibodies, receptor agonists, receptor antagonists, and other such agents as known to one skilled in the art. The reduction in administration of immuno-suppressants can be reflected through a lower dose, more time between doses and/or by stopping their administration earlier in time.

In particular embodiments, experimental transplant rejection can be analyzed by transplanting mice (e.g., C57BL/6 mice) with transplanted material under the renal capsules and administering Ex-CBSC. Reduced transplant rejection can be confirmed by sacrificing the transplant recipients and staining for cell viability, or performing immunocytochemical staining at the site of the transplanted material (i.e., an organ or tissue present at the site of the transplanted material) at a suitable post-transplantation time point. The time point at which staining (for example hematoxylin and eosin or immunostaining) of the site of the transplanted material is made can vary, for example, according to the average survival time, or the expected survival time of a transplanted animal.

In various models, a site of transplant can be analyzed, for example by staining, 1 day to 10 years (i.e., 1, 5, 10, 30, 100 or more days, 1, 2, or more years) post-transplantation, in particular embodiments, 10 days to 1 year post-transplantation and in more particular embodiments, 10-100 days post-transplantation. For example, if transplanted material is introduced under the renal capsule of a mouse, the kidney of the transplanted mouse can be inspected. Transplanted material is successfully engrafted (i.e., not rejected) if, the transplanted material is still detectable and/or, in particular embodiments, the transplanted material has proliferated into a tissue mass.

Detection of transplanted material and proliferation of the transplanted material can be determined, for example, by hematoxylin/eosin staining of a frozen section prepared from the transplant site (e.g., the kidney) and the detection of new growth that is not derived from the transplant recipient (e.g., not host kidney derived). In the case of xenogeneic transplantation, transplanted material is successfully engrafted if specific immunostaining with antisera specific for an antigen from the species from which the transplanted material is derived, according to methods of immunocytochemical staining known in the art, identifies positive cells. Alternatively, in embodiments wherein a xenogeneic transplantation is performed, transplanted material is successfully engrafted if molecules (i.e., a protein or an antigen) derived from the transplant species (that is the species from which the transplanted material is derived) are detected in the blood of the transplant recipient.

Reduced Total Parenteral Nutrition. Total parenteral nutrition (TPN) involves satisfying a patient's nutritional needs by means of intravenous feedings. TPN, which sometimes is also referred to as hyperalimentation, provides all the carbohydrates, proteins, fats, water, electrolytes, vitamins and minerals needed for the building of tissue, expenditure of energy and other physiologic activities.

TPN originated as an emergency procedure which was first used following surgery for severe and massive trauma of the gastrointestinal tract. Parenteral nutrition, whether it be total or supplemental, is now employed in a wide variety of chronic conditions, including following medical interventions that render a patient unable or unwilling to eat.

Although total parenteral nutrition is a lifesaving feeding program for many patients, every patient may suffer adverse reactions due to sensitivity to some of the elements in the nutrient mix and the possibility of feeding tube infections. Other complications that may develop include cardiac overload, choline deficiency, dehydration, electrolyte imbalance, hyperglycemia, mechanical trauma to the heart, metabolic acidosis, metabolic bone disease, phlebitis, renal diseases, and thrombosis of the vena cava. Thus, reducing the amount of time a patient receives TPN is of important clinical benefit.

The present disclosure provides use of Ex-CBSC to reduce TPN in patients following a medical procedure. As described in Example 2, the Ex-CBSC disclosed herein had a dramatic effect in reducing TPN following cord blood transplant in pediatric patients. Strikingly, the mean duration for TPN dropped from 30.1 days to 20.7 days following administration of Ex-CBSC. This significant reduction can help alleviate complications associated with TPN.

Reduced Opioid Use. Opioids are often administered after medical procedures to reduce pain associated with the procedure. The abuse of opioids, however, has risen to epidemic proportions in the United States. FDA Consumer Health Information, FDA Acts to Reduce Harm from Opioid Drugs, April 2011. The FDA estimates that in 2007, more than 33 million Americans misused opioids, an increase from 29 million five years earlier. While the U.S. government plans to address the epidemic through education and monitoring programs, such strategies may not sufficiently address the core of the problem, which is the addictive nature of the underlying opioid compounds.

As used herein, opioids include compounds that stimulate opioid receptors. Opioid receptors are G protein-coupled receptors (GPCRs) that are activated both by endogenous opioid peptides and by clinically important alkaloid analgesic drugs such as morphine. There are three principal types of opioid receptors: the $\delta$-opioid receptor, the $\kappa$-opioid receptor, and the $\mu$-opioid receptor. Examples of opioids include anileridine, allylprodine, alfentanil, alphaprodine, benzylmorphine, buprenorphine, bezitramide, butorphanol, codeine, clonitazene, cyclazocine, dezocine, desomorphine, dihydromorphine, dextromoramide, diampromide, dihydrocodeine, diethylthiambutene, dimenoxadol, dimepheptanol, dimethylthiambutene, dipipanone, dioxaphetyl butyrate, eptazocine, ethylmorphine, ethylmethylthiambutene, etonitazine, ethoheptazine, fentanyl, hydrocodone, heroin, 6-hydroxymorphone, hydroxypethidine, hydromorphone, isomethadone, ketobemidone, levallorphan, levophenacylmorphan, lofentanil, levorphanol, morphine, myrophine, meperidine, meptazinol, metazocine, methadone, metopon, morphine, narceine, nalbuphine, nalorphine, nicomorphine, norlevorphanol, normethadone, normorphine, norpipanone, opium, oxycodone, oxymorphone, piritramide, papaveretum, pentazocine, phenadoxone, phenazocine, phenoperidine, piminodine, phenomorphan, propheptazine, promedol, properidine, propiram, propoxyphene, sufentanil, tilidine, tramadol, stereoisomers thereof, metabolites thereof, salts thereof, ethers thereof, esters thereof, and/or derivatives thereof, and/or mixtures thereof.

Opioid agonists that target the mu opioid receptor are often administered in combination with a second analgesic, such as an antipyretic drug and/or a non-steroidal anti-inflammatory drug (NSAID). In some cases, it is believed that such combinations result in an additive, and in some cases, a synergistic effect when used for the treatment of pain. Examples of FDA approved combinations include PERCOCET® (oxycodone/acetaminophen) and VICODIN® (hydrocodone/acetaminophen). Due to the improved analgesic effect, such combinations may be dosed in a manner that lessens the amount of opioid administered to a patient ("opioid sparing"). Thus, the combinations provide a potential means for lessening the abuse potential of highly addictive opioids. Further, they may also lessen other side effects caused by opioids.

Nonetheless, additional methods to curb opioid use are needed and the present disclosure provides use of Ex-CBSC to reduce opioid use in patients following a medical procedure. In fact, as described in Example 2, the Ex-CBSC disclosed herein had a dramatic effect in reducing opioid use following cord blood transplant in pediatric patients. Strikingly, the mean duration for continuous opiate medications dropped from 18.1 days to 9.7 days following administration of Ex-CBSC.

Reduced Hospitalization. Health care costs are rising dramatically throughout the United States and other nations having advanced health-care systems. Any method that decreases the required hospitalization time associated with medical procedures will help alleviate these rising costs. Moreover, patients incur lost opportunity costs while undergoing medical procedures requiring extended hospitalization. Reducing required hospitalization time similarly assists patients in returning to more enjoyable and/or profitable endeavors. Thus, any method to reduce required hospitalization times associated with medical procedures would provide great societal and individual benefit.

As described in Example 2, the Ex-CBSC disclosed herein had a significant effect in hospitalization days following cord blood transplant in pediatric patients. On average, patients were released 12 days earlier (43.2 days in the hospital versus 55.6 days in the hospital), following administration of Ex-CBSC.

Without being bound by theory, the observed reductions of TPN, opioid use, and hospitalization following administration of Ex-CBSC may be related to the reduced mucositis that is also observed following administration of Ex-CBSC, as documented by professional medical care providers at patient bedside. Mucositis is an inflammatory reaction, characterized by lesions of the epithelial tissue of the gastrointestinal tract from mouth to anus. It may result from exposure to either ionizing radiation or chemotherapeutic agents. Stomatitis is any inflammatory reaction affecting the oral mucosa, with or without accompanying ulceration. Mucositis can be diagnosed, measured and monitored using clinically accepted standards. Thus, particular embodiments disclosed herein include administering Ex-CBSC to reduce mucositis in a patient in need thereof.

Maintaining the health of the gastrointestinal tract lining (e.g., the gut mucosa) may lead to some of the beneficial clinical effects described herein by reducing or preventing bacterial translocation. Bacterial translocation is the process whereby luminal bacteria migrate to extra-intestinal sites. Animal models are available, known to those of skill in the art and described in, for example, van Minnen et al., J Gastrointest Surg. 2007 May; 11(5):682-9.

In particular embodiments, the Ex-CBSC can be administered in combination with antimicrobial compounds. Examples of antimicrobials include antimicrobial compounds, anti-bacterials (e.g., antibiotics), antifungal agents, anti-infective agents, and antiviral agents. As is understood by one of ordinary skill in the art, particular compounds can fall within more than one of these generalized classifications.

Exemplary anti-microbials include antimicrobial compounds including antimicrobial peptides (AMPs), chlorhexidine diacetate, and silver carbonate.

Exemplary anti-bacterials (e.g., antibiotics) include aclarubicin, actinomycin D, actinoplanone, adriamycin, aeroplysinin derivative, aminoglycosides (e.g., gentamycin or neomycin), amoxicillin, ampicillin, amrubicin, anthracycline, azinomycin-A, azithromycin, aztreonam, bisucaberin, bleomycin sulfate, bryostatin-1, calichemycin, cefepime, cefixime, ceftriaxone, cephalosporin C, cephamandol, cephazolin, chloramphenicol, chromoximycin, ciprofloxacin, clindamycin, dactinomycin, daunorubicin, ditrisarubicin B, doxorubicin, doxorubicin-fibrinogen, doxycycline, elsamicin-A, epirubicin, erbstatin, erythromycin, esorubicin, esperamicin-Al, esperamicin-Alb, fostriecin, glidobactin, gregatin-A, grincamycin, herbimycin, idarubicin, illudins, imipenem, kazusamycin, kesarirhodins, menogaril, meropenem, metronidazole, mitomycin, neoenactin, netilmycin, oxalysine, oxaunomycin, penicillins (e.g., oxacillin or mezlocillin), peplomycin, pilatin, pirarubicin, porothramycin, pyrindanycin A, rifampicin, spectinomycin, streptomycin, tetracycline, tigecycline, tobramycin, and trimethoprim.

Exemplary antifungal agents include polyene antifungals, such as amphotericin B, candicidin, filipin, hamycin, imidaxole, natamycin, nystatin, rimocidin, thiazole antifungals, and triazole. Imidazole antifungal agents include bifonazole, blotrimazole, butoconazole, econazole, fenticonazole, isoconazole, ketoconazole, miconazole, omoconazole, oxiconazole, sertaconazole, sulconazole, and tioconazole. Triazole based antifungal agents include albaconazole, fluconazole, isavuconazole, itraconazole, posaconazole, ravuconazole, terconazole, and voriconazole. Thiazole antifungal agents include abafungin. Examples of allylamine antifungal agents include amorolfin, butenafine, naftifine and terbinafine. Echinocandin anti-fungal agents include anidulafungin, caspofungin, and micafungin. Additional antifungal agents include benzoic acid, ciclopirox, crystal violet, flucytosine or 5-fluorocytosine, griseofulvin, haloprogin, polygodial, tolnaftate and undecylenic acid. Essential oils having antifungal properties include allicin, citronella oil, coconut oil, lemon myrtle, lugol's iodine, neem seed oil, olive leaf, orange oil, oregano, palmarosa oil, patchouli, selenium, and tea tree oil.

Exemplary anti-infective agents include pyrimidine analogs. A pyrimidine analog generally refers to a compound with a pyrimidine ring structure (1,3-diazine) substituted with one or more atoms or chemical groups or oxidized at one or more carbons in the pyrimidine ring structure. In particular embodiments, the pyrimidine analog contains a halogen substituent, such as F, Cl, Br, or I, at a carbon in the pyrimidine ring structure. Exemplary fluoropyrimidines include 5-fluorocytosine, 5-fluorothymidine, 5-FU, 5-FUdR (5-fluoro-deoxyuridine; floxuridine), capecitabine, fluorodeoxyuridine monophosphate (5-dFUMP), fluorouridine triphosphate (5-FUTP), trifluorothymidine, and trifluridine. Other halogenated pyrimidine analogs include 5-bromocytosine, 5-bromodeoxyuridine (5-BudR), 5-bromouracil, 5-chlorocytosine, 5-chlorodeoxyuridine, 5-chlorouracil, 5-iodocytosine, 5-iododeoxyuridine (5-IudR), and 5-iodouracil.

Uracil pyrimidine analogs refer to compounds that contain a uracil ring structure substituted with one or more atoms or chemical groups. The uracil analog contains a halogen substituent, such as F, Cl, Br, or I. In certain embodiments, the uracil analog contains an F substituent, and is referred to as a fluorouracil analog. Exemplary fluorouracil analogs include 5-FU, carmofur, doxifluridine, emitefur, floxuridine, and tegafur.

Other exemplary anti-infectives include chlorhexidine, silver compounds, silver ions, silver particles, or other metallic compounds, ions or particles (such as gold). Additional anti-infective agents include 2-p-sulfanilyanilinoethanol, 4-sulfanilamidosalicylic acid, 4,4'-sulfinyldianiline, acetosulfone, amifloxacin, amikacin, amoxicillin, amphotericin B, apalcillin, apicycline, apramycin, arbekacin, aspoxicillin, azaserine, azidamfenicol, azithromycin, aztreonam, bacitracin, bambermycin(s), biapenem, brodimoprim, butirosin, candicidin(s), capreomycin, carbenicillin, carbomycin, carumonam, cefadroxil, cefamandole, cefatrizine, cefbuperazone, cefclidine, cefdinir, cefditoren, cefepime, cefetamet, cefinenoxime, cefixime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlorhexidine, chlorphenesin, chlortetracycline, ciprofloxacin, ciprofloxacin, clarithromycin, clinafloxacin, clindamycin, clomocycline, colistin, cyclacillin, dapsone, demeclocycline, dermostatin(s), diathymosulfone, dibekacin, dihydrostreptomycin, dirithromycin, enoxacin, enviomycin, epicillin, erythromycin, filipin, fleroxacin, flomoxef, fortimicin(s), fungichromin, gentamicin(s), glucosulfone solasulfone, gold compounds (such as gold chloride, auranofin), gold ions, gold particles, gramicidin S, gramicidin(s), grepafloxacin, guamecycline, hetacillin, imipenem, iodine, isepamicin, josamycin, kanamycin(s), leucomycin(s), lincomycin, lomefloxacin, lucensomycin, lymecycline, meclocycline, mepartricin, meropenem, methacycline, micronomicin, midecamycin(s), minocycline, moxalactam, mupirocin, nadifloxacin, natamycin, neomycin, netilmicin, norfloxacin, nystatin, ofloxacin, oleandomycin, oligomycin(s), oxytetracycline, panipenem, paromomycin, pazufloxacin, pefloxacin, penicillin N, perimycin A, pipacycline, pipemidic acid, polymyxin, povidone/iodine, primycin, p-sulfanilylbenzylamine, quinacillin, ribostamycin, rifamide, rifampin, rifamycin SV, rifapentine, rifaximin, ristocetin, ritipenem, rokitamycin, rolitetracycline, rosaramycin, rosoxacin, roxithromycin, salazosulfadimidine, sancycline, silver chloride, silver compounds (e.g. silver ions, silver nitrate, silver oxide), silver particles, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, tubercidin, and vancomycin.

Exemplary anti-viral agents include 5-bromouridine, acyclovir, alovudine, amantadine, antiviral proteins, arbidol, brivudine, cidofovir, daclatasvir, docosanol, double-stranded RNA (dsRNA) activated caspase oligomerizer (DRACO), famciclovir, FGI-104, fialuridine, fomivirsen, foscarnet, FV-100, ganciclovir, ibacitabine, idoxuridine, imiquimod, inosine, inosine pranobex, interferon, maribavir, methisazone, moroxydine, nucleotide antivirals, oragen, penciclovir, pleconaril, podophyllotoxin, prosetta, PSI-6130, reciGen, resiquimod, ribavirin, rintatolimod, semapimod, setrobuvir, simeprevir, sofosbuvir, sorivudine, taribavirin, tecovirimat, telbivudine, tenofovir alafenamide fumarate, theaflavin, tilorone, trifluridine, tromantadine, valaciclovir, valganciclovir, and vidarabine.

HSPC and antimicrobials can also be administered in combination with anti-septics. Exemplary anti-septics include alcohols (e.g., ethanol, 1-propanol, 2-propanol), quaternary ammonium salts also known as quats or QAC's (e.g., benzalkonium chloride (BAC), cetyl trimethylammonium bromide (CTMB), cetylpyridinium chloride (Cetrim, CPC) and benzethonium chloride (BZT)), boric acid, brilliant green, calcium hypochlorite, chlorhexidine gluconate, hydrogen peroxide, iodine (e.g., providone-iodine and Lugol's iodine), Mercurochrome, octenidine dihydrochloride, phenol (carbolic acid) compounds, polyhexanide (polyhexamethylene biguanide, PHMB), sodium bicarbonate, sodium chloride, and sodium hyposhlorite.

Reduced Graft versus Host Disease Following Allogeneic Hematopoietic Cell Transplantation. Hematopoietic cell transplantation (HCT) can be used to extend life, or can be the only curative treatment available for a variety of different hematologic cancers and diseases, including acute lymphoblastic leukemia, acute myeloid leukemia, chronic myelogenous leukemia, chronic lymphocytic leukemia, myelodysplastic syndrome (ALL, AML, CML, CLL, and MDS, respectively), lymphomas, multiple myeloma, severe aplastic anemia, and immune deficiency and autoimmune disorders, among many others.

One major obstacle to more widespread and successful application of HCT and other types of organ transplants is the risk of graft vs. host disease (GVHD) in the transplant recipient. GVHD is characterized by the donor tissue (graft or transplant) including or producing immune system cells that attack tissues of the recipient (host). GVHD occurs when functional immune cells in the transplant recognize the recipient as "foreign" and mount an immunologic attack. Many life-threatening complications occur due to GVHD and GVHD can be fatal when immune cells derived from transplanted material attack and sufficiently damage the recipient's organs.

GVHD can be acute or chronic. Acute GVHD is characterized by selective damage to the liver, skin, mucosa, gastrointestinal tract (GI), immune system (the hematopoietic system, e.g., the bone marrow and the thymus) itself, and the lungs (in the form of idiopathic pneumonitis). Acute GVHD is staged as follows: overall grade (skin-liver-gut) with each organ staged individually from a low of 1 (I) to a high of 4 (IV). Skin GVHD results in a diffuse maculopapular rash, sometimes in a lacy pattern. Liver GVHD can be measured by bilirubin level. The gut can be assessed based on presence and/or severity of intestinal inflammation, sloughing of the mucosal membrane, diarrhea, abdominal pain, nausea, and vomiting. Gut GVHD can be staged via intestinal biopsy. Kidney function also can be assessed by measuring creatinine and/or BUN levels. The described I-IV staging is clinically practiced and well accepted.

Patients with grade IV GVHD usually have a poor prognosis. If the GVHD is severe, controlling the disease can require intense additional immunosuppression involving steroids and additional agents, and the patient may develop severe, or even fatal, infections as a result of the immunosuppression. Chronic GVHD also attacks the above organs, but over its long-term course can also cause damage to the connective tissue and exocrine glands.

The pathophysiology of GVHD involves donor T cell interactions with host antigen presenting cells and the subsequent production of proinflammatory cytokines (cytokine storm), alongside activation of alloreactive T effector cells (T effectors) that cause target organ damage. By contrast, donor derived mature foxp3+T regulatory cells (Tregs) can downregulate alloreactivity. Thus, one hypothesis is that the ratio between donor T effectors and donor Tregs plays a key role in the severity of GVHD. Attempts to reduce GVHD by T cell depletion in transplanted hematopoietic cells, however, have led to significant relapse of malignancies in the cancer treatment context due to the loss of the therapeutic graft versus leukemia (GVL) effect, a failure of hematopoietic cell engraftment in the patient (host), and an increase in the rate of opportunistic infections.

Allogeneic, or genetically non-identical and therefore mismatched, hematopoietic stem cell transplants have been performed using umbilical cord blood because this stem cell type is more easily obtainable, carries a lower risk to the recipient of chronic GVHD, is painless for the donor, and importantly requires less of an HLA tissue type match between donor and recipient thus extending access to HCT for patients who cannot identify a matched related or a sufficiently matched unrelated adult volunteer donor. Currently in the clinical setting for cord blood transplants, HLA typing of the donor tissue and the recipient concerns determining six HLA antigens or alleles, usually two each at the loci HLA-A, HLA-B and HLA-DR, or one each at the loci HLA-A, HLA-B and HLA-C and one each at the loci HAL-DRB1, HLA-DQB1 and HLA-DPB1 (see e.g., Kawase et al., 2007, Blood 110:2235-2241). A 4/6 or 5/6 mismatch or a 6/6 match is the standard of clinical care.

A significant barrier to using cord blood as a source of cells for human blood transplants, however, has been that there are often not enough blood-forming stem/progenitor cells in a single cord blood unit to safely perform the transplant due to significantly delayed white blood cell and platelet recovery (hematopoietic reconstitution) as well as increased risk of graft failure. Thus, these patients are at significant risk of transplant related mortality. Because the size of a single cord blood unit (i.e., the number of blood-forming cells contained within that single donor donation) was often insufficient for a blood transplant, two cord blood units were frequently required. Use of two cord blood units dramatically reduced the risk of rejection/graft failure, but the time to hematopoietic recovery remained significantly delayed resulting in increased risk of life threatening infections and bleeding. Further, the risk of acute GVHD was also increased with the two cord blood unit approach, and cord blood transplant recipients remained at higher risk of early transplant related mortality.

Given the immune tolerance observed following administration of Ex-CBSC in the solid tissue transplant context, whether such immune tolerance could also be generated to reduce acute GVHD was examined. Initially, it was believed that acute GVHD was a significant risk associated with non-matched administration of Ex-CBSC due to the potential for significant HLA-mismatch. As described in Example 3, however, the current disclosure provides that unmatched Ex-CBSC unexpectedly reduce the occurrence and severity of acute GVHD in patients receiving HLA-matched (6/6) or mismatched (4/6 or 5/6) cord blood transplants for the treatment of high-risk acute leukemia, chronic myeloid leukemia, and myelodysplastic syndrome. No patients receiving unmatched Ex-CBSC in combination with the HLA-matched or mismatched cord blood units experienced Grade III-IV GVHD while 26% of patients who did not receive the Ex-CBSC in combination with the cord blood units did experience Grade III-IV GVHD. This result is significant because, as indicated earlier, patients with grade IV GVHD usually have a poor prognosis. Reducing the occurrence and severity of GVHD relieves the need for intense immunosuppression also reducing the risk of fatal infections and/or cancer development. This finding also supports that the Ex-CBSC induce immune tolerance in a diverse array of patients and transplant contexts.

In this context, immune tolerance refers to a decrease in the intensity of an immune response by the transplanted material against the host. In particular embodiments, the intensity of an immune response can be decreased by 5-100%, 25-100% or 75-100% as compared to the average graft immune response against a host as compared to transplant recipients that have not received Ex-CBSC as disclosed herein. In particular embodiments, the intensity of an immune response can be measured by determining the time point at which GVHD begins. For example, immune tolerance can allow the host and host organs to survive and function for a longer period of time. In particular embodiments, immune tolerance can refer to a state of the immune system (graft) in which certain foreign antigens do not elicit or elicit a reduced immune response.

Based on the foregoing, particular embodiments disclosed herein include administering Ex-CBSC to render an allogeneic hematopoietic cell transplant immune tolerant to a host. An allogeneic hematopoietic cell transplant (graft) that is immune tolerant fails to mount a significant immune response against a host such that the host has reduced occurrence and/or severity of GVHD, in particular embodiments, acute GHVD, and in more particular embodiments, acute Stage III or Stage IV GVHD. In particular embodiments, an allogeneic hematopoietic cell transplant that is immune tolerant does not respond to an antigen by producing antibodies capable of binding to the antigen, or responds at level that is reduced by a statistically-significant degree.

As indicated previously, the beneficial effects of the Ex-CBSC can reduce the need for immune suppression in patients receiving allogeneic hematopoietic cell transplants. Thus, following administration of Ex-CBSC, allogeneic hematopoietic cell transplant recipients may be administered less immuno-suppressants. As indicated previously, the reduction in administration of immuno-suppressants can be reflected through a lower dose, more time between doses and/or by stopping their administration earlier in time.

It is worthwhile to note that there are numerous references describing reduced GVHD following cord blood transplant. These references predominantly describe reduced GVHD following cord blood transplant as compared to GVHD that occurs following more standard bone marrow transplants. Furthermore, the reduced GVHD is generally reduced chronic GVHD. The current disclosure provides that administration of Ex-CBSC reduces GVHD associated with cord blood transplant even further. The Ex-CBSC further reduce acute GVHD, and more particularly the most dangerous forms of acute GVHD, Stages III and IV.

Outside of the clinical context, efficacy of acute GVHD reductions can also be confirmed using animal models. For example, immunodeficient NOD.SCIDyc−/− (NSG) mice (e.g., from the Jackson Laboratory) can be irradiated at 2 Gy before injection of 2106 total Peripheral Blood Mononuclear cells (PBMC) from healthy donors. Weight loss and survival of injected mice over time can be assessed as clinical parameters of GVHD appearance and severity. Weight loss can be represented as the percentage of initial weight of the injected mice at different time points after PBMC injection. Blood and spleen cells can also be harvested and frequencies of T cells can be determined by flow cytometry using human-specific fluorescent mAbs.

Selecting an Exp-CBSC Unit for Patient Administration. Throughout this disclosure, the importance of immunological matching (e.g., HLA matching) of solid tissue transplanted materials and cord blood units has been described. In contrast, the Exp-CBSC do not need to be immunologically matched, and instead are provided as an off-the-shelf product that can be administered to any patient without regard for immunological matching.

In particular embodiments, the Exp-CBSC are administered without immunologically matching the HLA-type of the Exp-CBSC to the HLA type of the patient. In particular embodiments, "without matching the HLA-type," and "without immunological matching" means that no steps are taken to have any of the HLA antigens or alleles match between the patient and the sample. In particular embodiments, the selection of the Exp-CBSC to be administered to the patient is done without taking into account whether the patient to whom the Exp-CBSC will be administered matches or mismatches the Exp-CBSC at any of the HLA antigens or alleles. Thus, the Exp-CBSC sample may have the same HLA type as the patient or the HLA type of the Exp-CBSC may differ from the HLA type of the patient at 1, 2, 3, 4, 5, 6 or more of the typed HLA antigens and/or alleles. In particular embodiments, the HLA type of Exp-CBSC sample may differ from the HLA type of the patient at all of the HLA antigens and/or alleles typed. For the avoidance of doubt, however, the transplant material (e.g., solid tissue or an allogeneic hematopoietic cell transplant) are immunologically matched within current clinical standards of care. Current clinical standards of care can allow some degree of mismatch within immunological matching. In particular embodiments, the Exp-CBSC can differentiate into cells of the myeloid lineage. In particular embodiments, the Exp-CBSC can differentiate into cells of the lymphoid lineage. In particular embodiments, Exp-CBSC are T cell depleted. T cell depletion can be the result of an active process and/or can be due to passive removal during CD34+ selection and expansion cultures.

Optional parameters for consideration in the selection of an unmatched Exp-CBSC can include one or more of total nucleated cell count, total CD34+ (or other suitable antigen) cell count, age of sample, age of patient, race or ethnic background of donor, weight of the patient, type of medical condition being treated and its level of severity in a particular patient, panel reactive antibody result of the patient, etc.

In particular embodiments, to prepare Exp-CBSC for administration to a patient cells can be harvested from a culture medium, and washed and concentrated into a carrier in a therapeutically-effective amount. Exemplary carriers include saline, buffered saline, physiological saline, water, Hanks' solution, Ringer's solution, Normosol-R (Abbott Labs), Plasma-Lyte A® (Baxter Laboratories, Inc., Morton Grove, Ill.), glycerol, and combinations thereof.

In particular embodiments, carriers can be supplemented with human serum albumin (HSA) or other human serum components or fetal bovine serum. In particular embodiments, a carrier for infusion includes buffered saline with 5% HSA or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. In particular embodiments, formulations can be calibrated to provide 1 million-20 million HSPC per kilogram when administered to a subject.

In formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml or more (e.g., $10^9$ cells/ml).

The formulations disclosed herein can be prepared for administration by, for example, injection, infusion, perfusion, or lavage. The formulations can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

The Exp-CBSC formulations are administered to subjects. Subjects include humans, veterinary animals (dogs, cats, reptiles, birds, etc.), livestock (horses, cattle, goats, pigs, chickens, etc.), and research animals (monkeys, rats, mice, fish, etc.). The Exp-CBSC formulations are administered to subjects in therapeutically effective amounts.

Therapeutically effective amounts include those that provide effective amounts, prophylactic treatments, and/or therapeutic treatments.

An "effective amount" is the amount of Exp-CBSC necessary to result in a desired physiological change in a subject. Effective amounts are often administered for research purposes. In experimental models, effective amounts disclosed herein do one or more of: (i) reduce transplant rejection; (ii) reduce TPN; (iii) reduce opioid use after a physiological procedure; (iv) reduce time to recovery as a proxy for hospitalization time; (v) reduce acute GVHD; (vi) induce immune tolerance; and/or (vi) reduce mucositis.

A "prophylactic treatment" includes a treatment administered to a subject who does not display signs or symptoms of a condition such that treatment is administered for the purpose of diminishing, preventing, or decreasing the risk of developing the condition (e.g., transplant rejection; GVHD). Thus, a prophylactic treatment functions as a preventative treatment against, for example, transplant rejection and/or Stage III and/or Stage IV GVHD.

A "therapeutic treatment" includes a treatment administered to a subject who displays symptoms or signs of a condition and is administered to the subject for the purpose of reducing the severity or progression of the condition. A therapeutic treatment can also partially or completely resolve the condition. Within the context of the current disclosure, conditions include one or more of transplant rejection, use of TPN, use of opioids following a medical procedure, hospitalization, GVHD, and mucositis.

Methods to assess the presence and/or severity of the noted conditions are provided throughout this disclosure, such that therapeutically effective amounts can be readily identified by those of ordinary skill in the art.

The actual amount of Exp-CBSC administered to a particular subject can be determined by a physician, veterinarian, or researcher taking into account parameters such as physical and physiological factors including target; body weight; type of condition; type of transplant; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells. In particular embodiments, therapeutically effective amounts include 1 million-20 million HSPC per kilogram.

Exp-CBSC can be administered by, for example, injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

In particular embodiments, amount of Exp-CBSC are administered without HLA matching (no steps are taken to determine degree the degree of matching between the subject and the Exp-CBSC).

Exp-CBSC are administered within clinically relevant time windows. In particular embodiments, in subjects undergoing a solid tissue transplant or an allogeneic hematopoietic cell transplant, the clinically relevant time window can be within 12 hours of the transplant (see, e.g., WO2006/047569 and WO2007/095594). In particular embodiments, the clinically relevant time window can be within 24 hours; 36 hours; 48 hours; or 1 week of a medical procedure, such as a transplant. The outer limits of clinically relevant time windows can be determined experimentally by increasing the delay between a medical intervention and administration of Exp-CBSC until the Exp-CBSC no longer provide the relevant clinical benefit.

Kits. Kits can include one or more containers including one or more Exp-CBSC formulations described herein. In particular embodiments, the kits can include one or more containers containing one or more Exp-CBSC formulations to be used in combination with other cells, compositions or formulations. Associated with such container(s) can be a notice in the form prescribed by a governmental agency regulating the manufacture, use, or sale of pharmaceuticals or biological products, which notice reflects approval by the agency of manufacture, use, or sale for human administration. The notice may state that the provided Exp-CBSC formulations can be administered to a subject without immunological matching. The kits can include further instructions for using the kit, for example, instructions regarding preparation of cells and/or formulations for administration; proper disposal of related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary medical supplies needed to use the kit effectively, such as syringes, ampules, tubing, facemask, a needleless fluid transfer device, an injection cap, sponges, sterile adhesive strips, Chloraprep, gloves, and the like. Variations in contents of any of the kits described herein can be made. The instructions of the kit will direct use of the Exp-CBSC to effectuate a new clinical use described herein.

EXEMPLARY EMBODIMENTS

1. A method of reducing allogeneic skin graft rejection in a subject in need thereof including: administering a therapeutically effective amount of a CD34+ enriched and expanded cord blood sample (Exp-CBSC) to the subject in need thereof within a clinically relevant time window of receiving an allogeneic skin graft thereby reducing allogeneic skin graft rejection in the subject.
2. A method of embodiment 1 wherein (i) the allogeneic skin graft and the subject are immunologically matched and (ii) the Exp-CBSC is administered to the subject without immunological matching.
3. A method of embodiment 1 or 2 wherein the Exp-CBSC were previously cryo-preserved.
4. A method of any of embodiments 1 wherein the Exp-CBSC do not include T cells.
5. A method of any of embodiments 1-3 wherein the subject is in need thereof due to trauma to the skin.
6. A method of embodiment 5 wherein the trauma is due to fire, heat, pressure, puncture, and/or abrasion.
7. A method of any of embodiments 1-6 wherein the clinically relevant time window occurs before receipt of the allogeneic skin graft.
8. A method of any of embodiments 1-7 wherein the clinically relevant time window is within 36 hours of receiving the allogeneic skin graft.
9. A method of any of embodiments 1-7 wherein the clinically relevant time window is within 12 hours of receiving the allogeneic skin graft.
10. A method of any of embodiments 1-9 wherein the Exp-CBSC includes at least 75 million CD34+ cells.
11. A method of any of embodiments 1-10 wherein the Exp-CBSC is derived from the umbilical cord blood and/or placental blood of a single human at birth.
12. A method of any of embodiments 1-10 wherein the Exp-CBSC includes a pool of two or more different expanded human cord blood stem cell samples, each different sample in the pool derived from the umbilical cord blood and/or placental blood of a different human at birth.
13. A method of any of embodiments 1-12 wherein the therapeutically effective amount includes 1 million-20 million CD34+ cells per kilogram of the subject.
14. Use of an unmatched CD34+ enriched and expanded cord blood sample (Exp-CBSC) to reduce allogeneic skin graft rejection in a subject in need thereof.
15. A use of embodiment 14 wherein the use includes administering a therapeutically effective amount to the subject in need thereof within a clinically relevant time window.
16. A use of embodiment 14 or 15 wherein the Exp-CBSC were previously cryo-preserved.
17. A use of any of embodiments 14-16 wherein the Exp-CBSC do not include T cells.

18. A use of any of embodiments 14-17 wherein the subject is in need thereof due to trauma to the skin.
19. A use of embodiment 18 wherein the trauma is due to fire, heat, pressure, puncture, and/or abrasion.
20. A use of any of embodiments 15-19 wherein the clinically relevant time window occurs before receipt of the allogeneic skin graft.
21. A use of any of embodiments 15-20 wherein the clinically relevant time window is within 36 hours of receiving the allogeneic skin graft.
22. A use of any of embodiments 15-20 wherein the clinically relevant time window is within 12 hours of receiving the allogeneic skin graft.
23. A use of any of embodiments 14-22 wherein the Exp-CBSC includes at least 75 million CD34+ cells.
24. A use of any of embodiments 14-23 wherein the Exp-CBSC is derived from the umbilical cord blood and/or placental blood of a single human at birth.
25. A use of any of embodiments 14-23 wherein the Exp-CBSC includes a pool of two or more different expanded human cord blood stem cell samples, each different sample in the pool derived from the umbilical cord blood and/or placental blood of a different human at birth.
26. A use of any of embodiments 15-25 wherein the therapeutically effective amount includes 1 million-20 million CD34+ cells per kilogram of the subject.
27. Use of an unmatched CD34+ enriched and expanded cord blood sample (Exp-CBSC) to induce immune tolerance in a transplant recipient.
28. A use of embodiment 27 wherein the use includes administering a therapeutically effective amount to the subject in need thereof within a clinically relevant time window.
29. A use of embodiment 27 or 28 wherein the Exp-CBSC were previously cryopreserved.
30. A use of any of embodiments 27-29 wherein the Exp-CBSC do not include T cells.
31. A use of any of embodiments 27-30 wherein the transplant recipient is a solid tissue transplant recipient.
32. A method embodiment 31 wherein the solid tissue includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
33. A use of any of embodiments 27-30 wherein the transplant recipient is a hematopoetic cell transplant recipient.
34. A use of any of embodiments 27-33 wherein the transplant recipient is an allogeneic transplant recipient.
35. A use of any of embodiments 27-30 wherein the transplant recipient is an allogeneic cord blood transplant recipient.
36. A use of any of embodiments 27-35 wherein the induced immune tolerance reduces the administration of immuno-suppressant drugs to the subject.
37. A use of embodiment 36 wherein the immuno-suppressant drugs include one or more of cyclosporin, cyclosporine A, cyclophosphamide, prednisone, dexamethasone, methotrexate, azathioprine, mycophenolate, mofetil, thalidomide, lithium, FK-506, sirolimus, ATG, infliximab, and systemic steroids.
38. A use of any of embodiments 28-37 wherein the clinically relevant time window occurs before receipt of the transplant.
39. A use of any of embodiments 28-38 wherein the clinically relevant time window is within 36 hours of transplant receipt.
40. A use of any of embodiments 28-38 wherein the clinically relevant time window is within 12 hours of transplant receipt.
41. A use of any of embodiments 27-40 wherein the Exp-CBSC includes at least 75 million CD34+ cells.
42. A use of any of embodiments 27-41 wherein the Exp-CBSC is derived from the umbilical cord blood and/or placental blood of a single human at birth.
43. A use of any of embodiments 27-41 wherein the Exp-CBSC includes a pool of two or more different expanded human cord blood stem cell samples, each different sample in the pool derived from the umbilical cord blood and/or placental blood of a different human at birth.
44. A use of any of embodiments 28-43 wherein the therapeutically effective amount includes 1 million-20 million CD34+ cells per kilogram of the subject.
45. A method of inducing immune tolerance to a solid tissue transplant in a solid tissue transplant recipient including: administering a therapeutically effective amount of a CD34+ enriched and expanded cord blood sample (Exp-CBSC) to the transplant recipient within a clinically relevant time window of receiving a solid tissue transplant thereby inducing immune tolerance to the solid tissue transplant in the solid tissue transplant recipient.
46. A method of embodiment 45 wherein (i) the solid tissue transplant and the subject are immunologically matched and (ii) the Exp-CBSC is administered to the subject without immunological matching.
47. A method of embodiment 45 or 46 wherein the Exp-CBSC were previously cryo-preserved.
48. A method of any of embodiments 45-47 wherein the Exp-CBSC do not include T cells.
49. A method of any of embodiments 45-48 wherein immune tolerance is evidenced by improved solid tissue transplant outcome.
50. A method of embodiment 49 wherein the improved solid tissue transplant outcome is evidenced by reduced transplant rejection as compared to a reference population not receiving Exp-CBSC.
51. A method of any of embodiments 49-50 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
52. A method of any of embodiments 49-51 wherein the improved solid tissue transplant outcome is evidenced by reduced administration of immuno-suppressant drugs as compared to a reference population not receiving Exp-CBSC.
53. A method of embodiment 52 wherein the immuno-suppressant drugs include one or more of cyclosporin, cyclosporine A, cyclophosphamide, prednisone, dexamethasone, methotrexate, azathioprine, mycophenolate, mofetil, thalidomide, lithium, FK-506, sirolimus, ATG, infliximab, and systemic steroids.

54. A method of any of embodiments 45-53 wherein the clinically relevant time window occurs before receipt of the solid tissue transplant.

55. A method of any of embodiments 45-54 wherein the clinically relevant time window is within 36 hours of receiving the solid tissue transplant.

56. A method of any of embodiments 45-54 wherein the clinically relevant time window is within 12 hours of receiving the solid tissue transplant.

57. A method of any of embodiments 45-56 wherein the Exp-CBSC includes at least 75 million CD34+ cells.

58. A method of any of embodiments 45-57 wherein the Exp-CBSC is derived from the umbilical cord blood and/or placental blood of a single human at birth.

59. A method of any of embodiments 45-57 wherein the Exp-CBSC includes a pool of two or more different expanded human cord blood stem cell samples, each different sample in the pool derived from the umbilical cord blood and/or placental blood of a different human at birth.

60. A method of any of embodiments 45-59 wherein the therapeutically effective amount includes 1 million-20 million CD34+ cells per kilogram of the subject.

61. Use of an unmatched CD34+ enriched and expanded cord blood sample (Exp-CBSC) to reduce administration of immuno-suppressant drugs in a subject in need thereof.

62. A use of embodiment 61 wherein the use includes administering a therapeutically effective amount to the subject in need thereof within a clinically relevant time window.

63. A use of embodiment 61 or 62 wherein the Exp-CBSC were previously cryopreserved.

64. A use of any of embodiments 61-63 wherein the Exp-CBSC do not include T cells.

65. A method of any of embodiments 61-64 wherein the immuno-suppressant drugs include one or more of cyclosporin, cyclosporine A, cyclophosphamide, prednisone, dexamethasone, methotrexate, azathioprine, mycophenolate, mofetil, thalidomide, lithium, FK-506, sirolimus, ATG, infliximab, and systemic steroids.

66. A use of any of embodiments 61-65 wherein the subject is receiving immuno-suppressant drugs due to a transplant procedure.

67. A use of embodiment 66 wherein the transplant procedure includes a solid tissue transplant procedure.

68. A use of embodiment 67 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

69. A use of any of embodiments 66 wherein the transplant procedure includes a hematopoietic cell transplant procedure.

70. A use of any of embodiments 66-69 wherein the transplant procedure includes an allogeneic transplant procedure.

71. A use of any of embodiments 66 wherein the transplant procedure includes an allogeneic cord blood transplant procedure.

72. A use of any of embodiments 62-71 wherein the clinically relevant time window occurs before the transplant procedure.

73. A use of any of embodiments 62-72 wherein the clinically relevant time window is within 36 hours of transplant procedure.

74. A use of any of embodiments 62-72 wherein the clinically relevant time window is within 12 hours of transplant procedure.

75. A use of any of embodiments 61-74 wherein the Exp-CBSC is derived from the umbilical cord blood and/or placental blood of a single human at birth.

76. A use of any of embodiments 61-74 wherein the Exp-CBSC includes a pool of two or more different expanded human cord blood stem cell samples, each different sample in the pool derived from the umbilical cord blood and/or placental blood of a different human at birth.

77. A use of any of embodiments 62-76 wherein the therapeutically effective amount includes 1 million-20 million CD34+ cells per kilogram of the subject.

78. A method of reducing the amount of immuno-suppressant drugs required by a solid tissue transplant recipient including:
administering a therapeutically effective amount of a CD34+ enriched and expanded cord blood sample (Exp-CBSC) to the transplant recipient within a clinically relevant time window of receiving a solid organ transplant thereby reducing the amount of immuno-suppressant drugs required by the solid tissue transplant recipient.

79. A method of embodiment 78 wherein (i) the solid tissue transplant and the subject are immunologically matched and (ii) the Exp-CBSC is administered to the subject without immunological matching.

80. A method of embodiment 78 or 79 wherein the Exp-CBSC were previously cryo-preserved.

81. A method of any of embodiments 78-80 wherein the Exp-CBSC do not include T cells.

82. A method of any of embodiments 78-81 wherein the immuno-suppressant drugs include one or more of cyclosporin, cyclosporine A, cyclophosphamide, prednisone, dexamethasone, methotrexate, azathioprine, mycophenolate, mofetil, thalidomide, lithium, FK-506, sirolimus, ATG, infliximab, and systemic steroids.

83. A method of any of embodiments 78-82 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

84. A method of any of embodiments 78-83 wherein the solid tissue transplant includes an allogeneic solid tissue transplant.

85. A method of any of embodiments 78-84 wherein the clinically relevant time window occurs before the solid tissue transplant.

86. A method of any of embodiments 78-85 wherein the clinically relevant time window is within 36 hours of receiving the solid tissue transplant.

87. A method of any of embodiments 78-85 wherein the clinically relevant time window is within 12 hours of receiving the solid tissue transplant.

88. A method of any of embodiments 78-87 wherein the Exp-CBSC includes at least 75 million CD34+ cells.
89. A method of any of embodiments 78-88 wherein the Exp-CBSC is derived from the umbilical cord blood and/or placental blood of a single human at birth.
90. A method of any of embodiments 78-88 wherein the Exp-CBSC includes a pool of two or more different expanded human cord blood stem cell samples, each different sample in the pool derived from the umbilical cord blood and/or placental blood of a different human at birth.
91. A method of any of embodiments 78-90 wherein the therapeutically effective amount includes 1 million-20 million CD34+ cells per kilogram of the subject.
92. Use of an unmatched CD34+ enriched and expanded cord blood sample (Exp-CBSC) to reduce total parenteral nutrition (TPN) in a subject in need thereof.
93. A use of embodiment 92 wherein the use includes administering a therapeutically effective amount to the subject in need thereof within a clinically relevant time window.
94. A use of embodiment 92 or 93 wherein the Exp-CBSC were previously cryo-preserved.
95. A use of any of embodiments 92-94 wherein the Exp-CBSC do not include T cells.
96. A use of any of embodiments 92-95 wherein the subject receives TPN following a medical procedure.
97. A use of embodiment 96 wherein the medical procedure includes a transplant.
98. A use of embodiment 97 wherein the transplant includes a solid tissue transplant.
99. A use of embodiment 98 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
100. A use of any of embodiments 97 wherein the transplant includes a hematopoietic cell transplant procedure.
101. A use of any of embodiments 97-100 wherein the transplant includes an allogeneic transplant procedure.
102. A use of any of embodiments 97 wherein the transplant includes an allogeneic cord blood transplant procedure.
103. A use of any of embodiments 92-102 wherein the subject is a pediatric subject.
104. A use of any of embodiments 93-103 wherein the clinically relevant time window occurs before the medical procedure.
105. A use of any of embodiments 93-104 wherein the clinically relevant time window is within 36 hours of the medical procedure.
106. A use of any of embodiments 93-104 wherein the clinically relevant time window is within 12 hours of the medical procedure.
107. A use of any of embodiments 92-106 wherein the Exp-CBSC includes at least 75 million CD34+ cells.
108. A use of any of embodiments 92-107 wherein the Exp-CBSC is derived from the umbilical cord blood and/or placental blood of a single human at birth.
109. A use of any of embodiments 92-107 wherein the Exp-CBSC includes a pool of two or more different expanded human cord blood stem cell samples, each different sample in the pool derived from the umbilical cord blood and/or placental blood of a different human at birth.
110. A use of any of embodiments 93-109 wherein the therapeutically effective amount includes 1 million-20 million CD34+ cells per kilogram of the subject.
111. A method including:
identifying a pediatric patient who will receive total parenteral nutrition (TPN) following receipt of an allogeneic transplant;
administering an unmatched CD34+ enriched and expanded cord blood sample (Exp-CBSC) to the pediatric patient within a clinically relevant time window of the allogeneic transplant;
thereby reducing total parenteral nutrition (TPN) use by the pediatric patient following the allogeneic transplant.
112. A method of embodiment 111 wherein (i) the allogeneic transplant and the subject are immunologically matched and (ii) the Exp-CBSC is administered to the subject without immunological matching.
113. A method of embodiment 111 or 112 wherein the Exp-CBSC were previously cryo-preserved.
114. A method of any of embodiments 111-113 wherein the Exp-CBSC do not include T cells.
115. A method of any of embodiments 111-114 wherein the allogeneic transplant includes a solid tissue transplant.
116. A method of embodiment 115 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
117. A method of any of embodiments 111-114 wherein the allogeneic transplant includes a hematopoietic cell transplant.
118. A method of any of embodiments 111-114 wherein the allogeneic transplant includes a cord blood transplant procedure.
119. A method of any of embodiments 111-118 wherein the clinically relevant time window occurs before the transplant.
120. A method of any of embodiments 111-119 wherein the clinically relevant time window is within 36 hours of receiving the transplant.
121. A method of any of embodiments 111-119 wherein the clinically relevant time window is within 12 hours of receiving the transplant.
122. A method of any of embodiments 111-121 wherein the Exp-CBSC includes at least 75 million CD34+ cells.
123. A method of any of embodiments 111-122 wherein the therapeutically effective amount includes 1 million-20 million CD34+ cells per kilogram of the subject.
124. A method of reducing total parenteral nutrition (TPN) use by a subject following a medical procedure including administering a therapeutically effective amount of a CD34+ enriched and expanded cord blood sample (Exp-CBSC) to the subject within a clinically relevant time window of the medical procedure thereby reducing TPN use by the subject following the medical procedure.
125. A method of embodiment 124 wherein the Exp-CBSC is administered to the subject without immunological matching.
126. A method of embodiment 124 or 125 wherein the Exp-CBSC were previously cryo-preserved.
127. A method of any of embodiments 124-126 wherein the Exp-CBSC do not include T cells.

128. A method of any of embodiments 124-127 wherein the medical procedure includes a transplant.

129. A method of embodiment 128 wherein the transplant includes a solid tissue transplant.

130. A method of embodiment 129 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

131. A method of any of embodiments 128 wherein the transplant includes a hematopoietic cell transplant.

132. A method of any of embodiments 128-131 wherein the transplant includes an allogeneic transplant.

133. A method of any of embodiments 128 wherein the transplant includes an allogeneic cord blood transplant.

134. A method of any of embodiments 124-133 wherein the subject is a pediatric subject.

135. A method of any of embodiments 124-134 wherein the clinically relevant time window occurs before the transplant.

136. A method of any of embodiments 124-135 wherein the clinically relevant time window is within 36 hours of receiving the transplant.

137. A method of any of embodiments 124-135 wherein the clinically relevant time window is within 12 hours of receiving the transplant.

138. A method of any of embodiments 124-137 wherein the Exp-CBSC includes at least 75 million CD34+ cells.

139. A method of any of embodiments 124-138 wherein the therapeutically effective amount includes 1 million-20 million CD34+ cells per kilogram of the subject.

140. Use of an unmatched CD34+ enriched and expanded cord blood sample (Exp-CBSC) to reduce opioid use in a subject in need thereof.

141. A use of embodiment 140 wherein the use includes administering a therapeutically effective amount to the subject in need thereof within a clinically relevant time window.

142. A use of embodiment 140 or 141 wherein the Exp-CBSC were previously cryo-preserved.

143. A use of any of embodiments 140-142 wherein the Exp-CBSC do not include T cells.

144. A use of any of embodiments 140-143 wherein the opioid is selected from one or more of anileridine, allylprodine, alfentanil, alphaprodine, benzylmorphine, buprenorphine, bezitramide, butorphanol, codeine, clonitazene, cyclazocine, dezocine, desomorphine, dihydromorphine, dextromoramide, diampromide, dihydrocodeine, diethylthiambutene, dimenoxadol, dimepheptanol, dimethylthiambutene, dipipanone, dioxaphetyl butyrate, eptazocine, ethylmorphine, ethylmethylthiambutene, etonitazine, ethoheptazine, fentanyl, hydrocodone, heroin, 6-hydroxymorphone, hydroxypethidine, hydromorphone, isomethadone, ketobemidone, levallorphan, levophenacylmorphan, lofentanil, levorphanol, morphine, myrophine, meperidine, meptazinol, metazocine, methadone, metopon, morphine, narceine, nalbuphine, nalorphine, nicomorphine, norlevorphanol, normethadone, normorphine, norpipanone, opium, oxycodone, oxymorphone, piritramide, papaveretum, pentazocine, phenadoxone, phenazocine, phenoperidine, piminodine, phenomorphan, propheptazine, promedol, properidine, propiram, propoxyphene, sufentanil, tilidine, tramadol, stereoisomers thereof, metabolites thereof, salts thereof, ethers thereof, esters thereof, and/or derivatives thereof, and/or mixtures thereof.

145. A use of any of embodiments 140-144 wherein the opioid is mixed with a second active ingredient.

146. A use of embodiment 145 wherein the opioid and second active ingredient include oxycodone and acetaminophen or hydrocodone and acetaminophen.

147. A use of any of embodiments 140-146 wherein the subject receives opioids following a medical procedure.

148. A use of embodiment 147 wherein the medical procedure includes a transplant.

149. A use of embodiment 148 wherein the transplant includes a solid tissue transplant.

150. A use of embodiment 149 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

151. A use of any of embodiments 148 wherein the transplant includes a hematopoietic cell transplant.

152. A use of any of embodiments 148-151 wherein the transplant includes an allogeneic transplant.

153. A use of any of embodiments 148 wherein the transplant includes an allogeneic cord blood transplant.

154. A use of any of embodiments 141-153 wherein the subject is a pediatric subject.

155. A use of any of embodiments 142-154 wherein the clinically relevant time window occurs before the medical procedure.

156. A use of any of embodiments 142-155 wherein the clinically relevant time window is within 36 hours of the medical procedure.

157. A use of any of embodiments 142-155 wherein the clinically relevant time window is within 12 hours of the medical procedure.

158. A use of any of embodiments 141-157 wherein the Exp-CBSC includes at least 75 million CD34+ cells.

159. A use of any of embodiments 141-158 wherein the Exp-CBSC is derived from the umbilical cord blood and/or placental blood of a single human at birth.

160. A use of any of embodiments 141-158 wherein the Exp-CBSC includes a pool of two or more different expanded human cord blood stem cell samples, each different sample in the pool derived from the umbilical cord blood and/or placental blood of a different human at birth.

161. A use of any of embodiments 142-160 wherein the therapeutically effective amount includes 1 million-20 million CD34+ cells per kilogram of the subject.

162. A method including:
identifying a pediatric patient who will receive opioids following receipt of an allogeneic transplant;
administering an unmatched CD34+ enriched and expanded cord blood sample (Exp-CBSC) to the pediatric patient within a clinically relevant time window of the allogeneic transplant;
thereby reducing opioid use by the pediatric patient following the allogeneic transplant.

163. A method of embodiment 162 wherein (i) the allogeneic transplant and the subject are immunologically matched and (ii) the Exp-CBSC is administered to the subject without immunological matching.

164. A method of embodiment 162 or 163 wherein the Exp-CBSC were previously cryo-preserved.

165. A method of any of embodiments 162-164 wherein the Exp-CBSC do not include T cells.

166. A method of any of embodiments 162-165 wherein the opioid is selected from one or more of anileridine, allylprodine, alfentanil, alphaprodine, benzylmorphine, buprenorphine, bezitramide, butorphanol, codeine, clonitazene, cyclazocine, dezocine, desomorphine, dihydromorphine, dextromoramide, diampromide, dihydrocodeine, diethylthiambutene, dimenoxadol, dimepheptanol, dimethylthiambutene, dipipanone, dioxaphetyl butyrate, eptazocine, ethylmorphine, ethylmethylthiambutene, etonitazine, ethoheptazine, fentanyl, hydrocodone, heroin, 6-hydroxymorphone, hydroxypethidine, hydromorphone, isomethadone, ketobemidone, levallorphan, levophenacylmorphan, lofentanil, levorphanol, morphine, myrophine, meperidine, meptazinol, metazocine, methadone, metopon, morphine, narceine, nalbuphine, nalorphine, nicomorphine, norlevorphanol, normethadone, normorphine, norpipanone, opium, oxycodone, oxymorphone, piritramide, papaveretum, pentazocine, phenadoxone, phenazocine, phenoperidine, piminodine, phenomorphan, propheptazine, promedol, properidine, propiram, propoxyphene, sufentanil, tilidine, tramadol, stereoisomers thereof, metabolites thereof, salts thereof, ethers thereof, esters thereof, and/or derivatives thereof, and/or mixtures thereof.

167. A method of any of embodiments 162-166 wherein the opioid is mixed with a second active ingredient.

168. A method of embodiment 167 wherein the opioid and second active ingredient include oxycodone and acetaminophen or hydrocodone and acetaminophen.

169. A method of any of embodiments 162-168 wherein the allogeneic transplant includes a solid tissue transplant.

170. A method of embodiment 169 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

171. A method of any of embodiments 162-168 wherein the allogeneic transplant includes a hematopoietic cell transplant.

172. A method of any of embodiments 162-168 wherein the allogeneic transplant includes a cord blood transplant procedure.

173. A method of any of embodiments 162-172 wherein the clinically relevant time window occurs before the transplant.

174. A method of any of embodiments 162-173 wherein the clinically relevant time window is within 36 hours of receiving the transplant.

175. A method of any of embodiments 162-173 wherein the clinically relevant time window is within 12 hours of receiving the transplant.

176. A method of any of embodiments 162-175 wherein the Exp-CBSC includes at least 75 million CD34+ cells.

177. A method of any of embodiments 162-176 wherein the therapeutically effective amount includes 1 million-20 million CD34+ cells per kilogram of the subject.

178. A method of reducing opioid use by a subject following a medical procedure including administering a therapeutically effective amount of a CD34+ enriched and expanded cord blood sample (Exp-CBSC) to the subject within a clinically relevant time window of the medical procedure thereby reducing opioid use by the subject following the medical procedure.

179. A method of embodiment 178 wherein the Exp-CBSC is administered to the subject without immunological matching.

180. A method of embodiment 178 or 179 wherein the Exp-CBSC were previously cryo-preserved.

181. A method of any of embodiments 178-180 wherein the Exp-CBSC do not include T cells.

182. A method of any of embodiments 178-181 wherein the opioid is selected from one or more of anileridine, allylprodine, alfentanil, alphaprodine, benzylmorphine, buprenorphine, bezitramide, butorphanol, codeine, clonitazene, cyclazocine, dezocine, desomorphine, dihydromorphine, dextromoramide, diampromide, dihydrocodeine, diethylthiambutene, dimenoxadol, dimepheptanol, dimethylthiambutene, dipipanone, dioxaphetyl butyrate, eptazocine, ethylmorphine, ethylmethylthiambutene, etonitazine, ethoheptazine, fentanyl, hydrocodone, heroin, 6-hydroxymorphone, hydroxypethidine, hydromorphone, isomethadone, ketobemidone, levallorphan, levophenacylmorphan, lofentanil, levorphanol, morphine, myrophine, meperidine, meptazinol, metazocine, methadone, metopon, morphine, narceine, nalbuphine, nalorphine, nicomorphine, norlevorphanol, normethadone, normorphine, norpipanone, opium, oxycodone, oxymorphone, piritramide, papaveretum, pentazocine, phenadoxone, phenazocine, phenoperidine, piminodine, phenomorphan, propheptazine, promedol, properidine, propiram, propoxyphene, sufentanil, tilidine, tramadol, stereoisomers thereof, metabolites thereof, salts thereof, ethers thereof, esters thereof, and/or derivatives thereof, and/or mixtures thereof.

183. A method of any of embodiments 178-182 wherein the opioid is mixed with a second active ingredient.

184. A method of embodiment 183 wherein the opioid and second active ingredient include oxycodone and acetaminophen or hydrocodone and acetaminophen.

185. A method of any of embodiments 178-184 wherein the medical procedure includes a transplant.

186. A method of embodiment 185 wherein the transplant includes a solid tissue transplant.

187. A method of embodiment 186 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

188. A method of any of embodiments 185-184 wherein the transplant includes a hematopoietic cell transplant.

189. A method of any of embodiments 185-188 wherein the transplant includes an allogeneic transplant.

190. A method of any of embodiments 185 wherein the transplant includes an allogeneic cord blood transplant.

191. A method of any of embodiments 178-190 wherein the subject is a pediatric subject.
192. A method of any of embodiments 178-191 wherein the clinically relevant time window occurs before the transplant.
193. A method of any of embodiments 178-192 wherein the clinically relevant time window is within 36 hours of receiving the transplant.
194. A method of any of embodiments 178-192 wherein the clinically relevant time window is within 12 hours of receiving the transplant.
195. A method of any of embodiments 178-194 wherein the Exp-CBSC includes at least 75 million CD34+ cells.
196. A method of any of embodiments 178-195 wherein the therapeutically effective amount includes 1 million-20 million CD34+ cells per kilogram of the subject.
197. Use of an unmatched CD34+ enriched and expanded cord blood sample (Exp-CBSC) to reduce hospitalization in a subject in need thereof.
198. A use of embodiment 197 wherein the use includes administering a therapeutically effective amount to the subject in need thereof within a clinically relevant time window.
199. A use of embodiment 197 or 198 wherein the Exp-CBSC were previously cryo-preserved.
200. A use of any of embodiments 197-199 wherein the Exp-CBSC do not include T cells.
201. A use of any of embodiments 197-200 wherein the subject is hospitalized due to a transplant procedure.
202. A use of embodiment 201 wherein the transplant procedure includes a solid tissue transplant.
203. A use of embodiment 202 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
204. A use of any of embodiments 201 wherein the transplant procedure includes a hematopoietic cell transplant.
205. A use of any of embodiments 201-204 wherein the transplant procedure includes an allogeneic transplant.
206. A use of embodiment 201 wherein the transplant procedure includes an allogeneic cord blood transplant.
207. A use of any of embodiments 197-206 wherein the subject is a pediatric subject.
208. A use of any of embodiments 198-207 wherein the clinically relevant time window occurs before the medical procedure.
209. A use of any of embodiments 198-208 wherein the clinically relevant time window is within 36 hours of the medical procedure.
210. A use of any of embodiments 198-208 wherein the clinically relevant time window is within 12 hours of the medical procedure.
211. A use of any of embodiments 197-210 wherein the Exp-CBSC includes at least 75 million CD34+ cells.
212. A use of any of embodiments 197-211 wherein the Exp-CBSC is derived from the umbilical cord blood and/or placental blood of a single human at birth.
213. A use of any of embodiments 197-211 wherein the Exp-CBSC includes a pool of two or more different expanded human cord blood stem cell samples, each different sample in the pool derived from the umbilical cord blood and/or placental blood of a different human at birth.
214. A use of any of embodiments 198-213 wherein the therapeutically effective amount includes 1 million-20 million CD34+ cells per kilogram of the subject.
215. A method including:
identifying a pediatric patient who will be hospitalized following receipt of an allogeneic transplant;
administering an unmatched CD34+ enriched and expanded cord blood sample (Exp-CBSC) to the pediatric patient within a clinically relevant time window of the allogeneic transplant;
thereby reducing hospitalization time of the pediatric patient following the allogeneic transplant.
216. A method of embodiment 215 wherein (i) the allogeneic transplant graft and the subject are immunologically matched and (ii) the Exp-CBSC is administered to the subject without immunological matching.
217. A method of embodiment 215 or 216 wherein the Exp-CBSC were previously cryo-preserved.
218. A method of any of embodiments 215-217 wherein the Exp-CBSC do not include T cells.
219. A method of any of embodiments 215-218 wherein the allogeneic transplant includes a solid tissue transplant.
220. A method of embodiment 219 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
221. A method of any of embodiments 215-218 wherein the allogeneic transplant includes a hematopoietic cell transplant.
222. A method of any of embodiments 215-218 wherein the allogeneic transplant includes a cord blood transplant procedure.
223. A method of any of embodiments 215-222 wherein the clinically relevant time window occurs before the transplant.
224. A method of any of embodiments 215-223 wherein the clinically relevant time window is within 36 hours of receiving the transplant.
225. A method of any of embodiments 215-223 wherein the clinically relevant time window is within 12 hours of receiving the transplant.
226. A method of any of embodiments 215-225 wherein the Exp-CBSC includes at least 75 million CD34+ cells.
227. A method of any of embodiments 215-226 wherein the therapeutically effective amount includes 1 million-20 million CD34+ cells per kilogram of the subject.
228. A method of reducing hospitalization time for a subject following a medical procedure including administering a therapeutically effective amount of a CD34+ enriched and expanded cord blood sample (Exp-CBSC) to the subject within a clinically relevant time window of the medical procedure thereby reducing hospitalization time for the subject following the medical procedure.
229. A method of embodiment 228 wherein the Exp-CBSC is administered to the subject without immunological matching.
230. A method of embodiment 228 or 229 wherein the Exp-CBSC were previously cryo-preserved.

231. A method of any of embodiments 228-230 wherein the Exp-CBSC do not include T cells.
232. A method of any of embodiments 228-231 wherein the medical procedure includes a transplant.
233. A method of embodiment 232 wherein the transplant includes a solid tissue transplant.
234. A method of embodiment 233 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
235. A method of any of embodiments 232 wherein the transplant includes a hematopoietic cell transplant.
236. A method of any of embodiments 232-235 wherein the transplant includes an allogeneic transplant.
237. A method of any of embodiments 228-231 wherein the transplant includes an allogeneic cord blood transplant.
238. A method of any of embodiments 228-237 wherein the subject is a pediatric subject.
239. A method of any of embodiments 228-238 wherein the clinically relevant time window occurs before the transplant.
240. A method of any of embodiments 228-239 wherein the clinically relevant time window is within 36 hours of receiving the transplant.
241. A method of any of embodiments 228-239 wherein the clinically relevant time window is within 12 hours of receiving the transplant.
242. A method of any of embodiments 228-241 wherein the Exp-CBSC includes at least 75 million CD34+ cells.
243. A method of any of embodiments 228-242 wherein the therapeutically effective amount includes 1 million-20 million CD34+ cells per kilogram of the subject.
244. Use of an unmatched CD34+ enriched and expanded cord blood sample (Exp-CBSC) to reduce mucositis in a subject in need thereof.
245. A use of embodiment 244 wherein the use includes administering a therapeutically effective amount to the subject in need thereof within a clinically relevant time window.
246. A use of embodiment 244 or 245 wherein the Exp-CBSC were previously cryo-preserved.
247. A use of any of embodiments 244-246 wherein the Exp-CBSC do not include T cells.
248. A use of any of embodiments 244-247 wherein the subject is in need thereof due to a transplant procedure.
249. A use of embodiment 248 wherein the transplant procedure includes a solid tissue transplant.
250. A use of embodiment 249 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
251. A use of embodiment 248 wherein the transplant procedure includes a hematopoietic cell transplant.
252. A use of any of embodiments 248-251 wherein the transplant procedure includes an allogeneic transplant.
253. A use of embodiment 248 wherein the transplant procedure includes an allogeneic cord blood transplant.
254. A use of any of embodiments 244-253 wherein the subject is a pediatric subject.
255. A use of any of embodiments 245-254 wherein the clinically relevant time window occurs before the medical procedure.
256. A use of any of embodiments 245-255 wherein the clinically relevant time window is within 36 hours of the medical procedure.
257. A use of any of embodiments 245-255 wherein the clinically relevant time window is within 12 hours of the medical procedure.
258. A use of any of embodiments 244-257 wherein the Exp-CBSC includes at least 75 million CD34+ cells.
259. A use of any of embodiments 244-258 wherein the Exp-CBSC is derived from the umbilical cord blood and/or placental blood of a single human at birth.
260. A use of any of embodiments 244-258 wherein the Exp-CBSC includes a pool of two or more different expanded human cord blood stem cell samples, each different sample in the pool derived from the umbilical cord blood and/or placental blood of a different human at birth.
261. A use of any of embodiments 245-260 wherein the therapeutically effective amount includes 1 million-20 million CD34+ cells per kilogram of the subject.
262. A method including:
identifying a pediatric patient at risk for developing mucositis based on receipt of an allogeneic transplant;
administering an unmatched CD34+ enriched and expanded cord blood sample (Exp-CBSC) within a clinically relevant time window of the allogeneic transplant;
thereby reducing mucositis in the pediatric patient at risk.
263. A method of embodiment 262 wherein (i) the allogeneic transplant graft and the subject are immunologically matched and (ii) the Exp-CBSC is administered to the subject without immunological matching.
264. A method of embodiment 262 or 263 wherein the Exp-CBSC were previously cryo-preserved.
265. A method of any of embodiments 262-264 wherein the Exp-CBSC do not include T cells.
266. A method of any of embodiments 262-265 wherein the allogeneic transplant includes a solid tissue transplant.
267. A method of embodiment 266 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.
268. A method of any of embodiments 262-265 wherein the allogeneic transplant includes a hematopoietic cell transplant.
269. A method of any of embodiments 262-265 wherein the allogeneic transplant includes a cord blood transplant procedure.
270. A method of any of embodiments 262-269 wherein the clinically relevant time window occurs before the transplant.
271. A method of any of embodiments 262-270 wherein the clinically relevant time window is within 36 hours of receiving the transplant.

272. A method of any of embodiments 262-270 wherein the clinically relevant time window is within 12 hours of receiving the transplant.

273. A method of any of embodiments 262-272 wherein the Exp-CBSC includes at least 75 million CD34+ cells.

274. A method of any of embodiments 262-273 wherein the therapeutically effective amount includes 1 million-20 million CD34+ cells per kilogram of the subject.

275. A method of reducing mucositis for a subject following a medical procedure including administering a therapeutically effective amount of a CD34+ enriched and expanded cord blood sample (Exp-CBSC) to the subject within a clinically relevant time window of the medical procedure thereby reducing mucositis for the subject following the medical procedure.

276. A method of embodiment 275 wherein the Exp-CBSC is administered to the subject without immunological matching.

277. A method of embodiment 275 or 276 wherein the Exp-CBSC were previously cryo-preserved.

278. A method of any of embodiments 275-277 wherein the Exp-CBSC do not include T cells.

279. A method of any of embodiments 275-278 wherein the medical procedure includes a transplant.

280. A method of embodiment 279 wherein the transplant includes a solid tissue transplant.

281. A method of embodiment 280 wherein the solid tissue transplant includes adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

282. A method of any of embodiments 279 wherein the transplant includes a hematopoietic cell transplant.

283. A method of any of embodiments 279-282 wherein the transplant includes an allogeneic transplant.

284. A method of any of embodiments 279 wherein the transplant includes an allogeneic cord blood transplant.

285. A method of any of embodiments 275-284 wherein the subject is a pediatric subject.

286. A method of any of embodiments 275-285 wherein the clinically relevant time window occurs before the medical procedure.

287. A method of any of embodiments 275-286 wherein the clinically relevant time window is within 36 hours of receiving the transplant.

288. A method of any of embodiments 275-286 wherein the clinically relevant time window is within 12 hours of receiving the transplant.

289. A method of any of embodiments 275-288 wherein the Exp-CBSC includes at least 75 million CD34+ cells.

290. A method of any of embodiments 275-289 wherein the therapeutically effective amount includes 1 million-20 million CD34+ cells per kilogram of the subject.

291. Use of an unmatched CD34+ enriched and expanded cord blood sample (Exp-CBSC) to reduce acute graft versus host disease in a subject in need thereof.

292. A use of embodiment 291 wherein the use includes administering a therapeutically effective amount to the subject in need thereof within a clinically relevant time window.

293. A use of embodiment 291 or 292 wherein the Exp-CBSC were previously cryo-preserved.

294. A use of any of embodiments 291-293 wherein the Exp-CBSC do not include T cells.

295. A use of any of embodiments 291-294 wherein the reduced acute GVHD includes reduced Stage III acute GVHD.

296. A use of any of embodiments 291-295 wherein the reduced acute GVHD includes reduced Stage IV acute GVHD.

297. A use of any of embodiments 291-296 wherein the subject is in need thereof due to an allogeneic hematopoietic cell transplant.

298. A use of embodiment 297 wherein the allogeneic hematopoietic cell transplant includes a cord blood transplant.

299. A use of embodiment 298 wherein the cord blood transplant and the subject match at 4/6; 5/6; or 6/6 HLA antigens.

300. A use of any of embodiments 291-299 wherein the subject is a pediatric subject.

301. A use of any of embodiments 292-300 wherein the clinically relevant time window occurs before the medical procedure.

302. A use of any of embodiments 292-301 wherein the clinically relevant time window is within 36 hours of the medical procedure.

303. A use of any of embodiments 292-301 wherein the clinically relevant time window is within 12 hours of the medical procedure.

304. A use of any of embodiments 291-303 wherein the Exp-CBSC includes at least 75 million CD34+ cells.

305. A use of any of embodiments 291-304 wherein the Exp-CBSC is derived from the umbilical cord blood and/or placental blood of a single human at birth.

306. A use of any of embodiments 291-304 wherein the Exp-CBSC includes a pool of two or more different expanded human cord blood stem cell samples, each different sample in the pool derived from the umbilical cord blood and/or placental blood of a different human at birth.

307. A use of any of embodiments 292-306 wherein the therapeutically effective amount includes 1 million-20 million CD34+ cells per kilogram of the subject.

308. A method including:
identifying a patient at risk for acute graft versus host disease (GVHD) based on receipt of an allogeneic transplant;
administering an unmatched CD34+ enriched and expanded cord blood sample (Exp-CBSC) within a clinically relevant time window of the allogeneic transplant;
thereby reducing acute GVHD in the patient at risk.

309. A method of embodiment 308 wherein (i) the allogeneic transplant graft and the subject are immunologically matched and (ii) the Exp-CBSC is administered to the subject without immunological matching.

310. A method of embodiment 308 or 309 wherein the Exp-CBSC were previously cryo-preserved.

311. A method of any of embodiments 308-310 wherein the Exp-CBSC do not include T cells.

312. A method of any of embodiments 308-311 wherein the reduced acute GVHD includes reduced Stage III acute GVHD.

313. A method of any of embodiments 308-312 wherein the reduced acute GVHD includes reduced Stage IV acute GVHD.

314. A method of any of embodiments 308-313 wherein the subject is in need thereof due to an allogeneic hematopoietic cell transplant.

315. A method of embodiment 314 wherein the allogeneic hematopoietic cell transplant includes a cord blood transplant.

316. A method of embodiment 315 wherein the cord blood transplant and the subject match at 4/6; 5/6; or 6/6 HLA antigens.

317. A method of any of embodiments 308-316 wherein the subject is a pediatric subject.

318. A method of any of embodiments 308-317 wherein the clinically relevant time window occurs before the medical procedure.

319. A method of any of embodiments 308-318 wherein the clinically relevant time window is within 36 hours of the medical procedure.

320. A method of any of embodiments 308-318 wherein the clinically relevant time window is within 12 hours of the medical procedure.

321. A method of any of embodiments 308-320 wherein the Exp-CBSC includes at least 75 million CD34+ cells.

322. A method of any of embodiments 308-321 wherein the Exp-CBSC is derived from the umbilical cord blood and/or placental blood of a single human at birth.

323. A method of any of embodiments 308-321 wherein the Exp-CBSC includes a pool of two or more different expanded human cord blood stem cell samples, each different sample in the pool derived from the umbilical cord blood and/or placental blood of a different human at birth.

324. A method of any of embodiments 308-323 wherein the therapeutically effective amount includes 1 million-20 million CD34+ cells per kilogram of the subject.

Example 1

Reduced Transplant Rejection in MHC Mismatched Recipients Receiving Notch-Expanded Murine Hematopoietic Stem and Progenitor Cells. Infusion of ex vivo expanded murine hematopoietic stem and progenitor cells (HSPCs) into completely major histocompatibility complex mismatched recipients improves survival of donor-derived but not third-party skin grafts. This finding shows that ex vivo expanded mismatched HSPCs convey donor-specific immune tolerance in a murine h-ARS model.

Allogeneic hematopoietic stem cell transplants (HCT) promote donor-specific immune tolerance and subsequently decreases the risk for acute and chronic graft rejection in recipients of solid organ transplants (Millan et al., 2002, Transplantation; 73:1386-1391; Scandling et al., 2008, N Engl J Med 358:362-368; Granados et al., 2015, Curr Opin Organ Transplant. 20:49-56). Successful conveyance of allograft immune tolerance in the nonmyeloablative HCT setting with persistent mixed chimerism and complete withdrawal of immunosuppressive drugs has been observed in renal transplant recipients (Kawai et al., Am J Transplant 2014, 14: 1599-1611; Scandling et al., Am J Transplant 2015, 15:695-704; Sorof et al., Transplantation 1995, 59:1633-1635). Interestingly, renal allograft tolerance has been induced even with transient chimerism in nonhuman primates and humans (Sorof et al., Transplantation 1995, 59:1633-1635, Kawai and Sachs, Curr Opin Organ Transplant 2013, 18:402-407). Kawai hypothesized that this phenomenon was due to transient expansion of donor hematopoietic cells, such as immature dendritic cells or T cells, which may result in thymic deletion of donor-reactive recipient T cells or induction of donor-specific regulatory T cells.

This example reports that infusion of a MHC mismatched cryopreserved ex vivo expanded mouse HSPC (Lin-Sca1+ cKit+ [LSK] cells) product after a lethal dose of radiation induces donor-specific immune tolerance, resulting in longer survival of donor skin allografts. These data reinforce that this clinically relevant, cryopreserved, universal donor, off-the-shelf cell products could induce donor-specific tolerance in organ transplant recipients, reducing transplant rejection.

Methods. Mice. Female or male B6-Ly5a (H-2b, CD45.1+) mice were bred and maintained in the Animal Health Resources center of the Fred Hutchinson Cancer Research Center (FHCRC) under specific pathogen-free conditions. Female BALB/cJ (H-2d, CD45.2+) and C3H (H-2k, CD45.2+) mice were purchased from the Jackson Laboratory (Bar Harbor, Me.). Mice were maintained under standard conditions, and all experiments were performed under the approval and guidance of the FHCRC Institutional Animal Care and Use Committee (IACUC).

Isolation and Expansion of Mouse Hematopoietic Stem and Progenitor Cells. LSK cells from B6-Ly5a mouse BM were enriched by using the fluorescence-activated cells sorter (FACS) Aria (Becton Dickinson [BD], Franklin Lakes, N.J.) as previously described (Varnum-Finney, et al., Blood 1998, 91:4084-4091). After each sort, the purity of the sorted populations was confirmed and exceeded 90%. Non-tissue culture-treated 6-well plates were coated with engineered Notch ligand (Delta1ext-IgG; DXI) or human IgG at a concentration of 5 mg/ml for 2 hours at 37° C., then washed with phosphate-buffered saline (PBS) and blocked for at least 30 minutes with PBS containing 2% bovine serum albumin. Sorted LSK cells were cultured in the presence of DXI or IgG in Iscove's modified Dulbecco medium (Thermo Fisher Scientific Life Sciences, Waltham, Mass.) supplemented with 20% fetal bovine serum (Hyclone FBS, Thermo Fisher Scientific Life Sciences), 1% penicillin-streptomycin, and the following cytokines: murine stem cell factor, human Flt-3 ligand, human IL-6 (100 ng/ml each), and human IL-11 (10 ng/ml; all cytokines purchased from PeproTech, Rocky Hill, N.J.) (Varnum-Finney et al., 2003, 101:1784-1789). Cell density was maintained at $1\times10^6$ cells/ml during the 14-day culture. At the end of 14 days, expanded LSK cells were harvested and fresh cells were used for transplantation experiments or cryopreserved in 90% FBS+10% dimethyl sulfoxide. On the day of transplantation, post-thaw cell recovery and preservation of LSK phenotype were determined by using trypan blue dye exclusion and flow cytometry, respectively.

Irradiation, Hematopoietic Stem Cell Transplantation, and Tracking Donor Chimerism. Female BALB/cJ mice, 6-8 weeks old, received a single dose of 6.5-8.5 Gy γ-irradiation using a Cesium source (JL Shepherd & Associates, San Fernando, Calif.) at a rate of 81.4 cGy/min. Four to 72 hours later, mice were injected intravenously with IgG- or DXI-expanded fresh or cryopreserved LSK cells (1, 3, 5, and $15\times10^6$ cells as indicated). To omit the effect of sex, avoid confounding variables, and decrease experimental size, only female mice were used as recipients. Once it was confirmed that IgG-expanded cells did not result in donor reconstitution, control mice were injected with saline solution in subsequent experiments. Mice were observed daily, and moribund animals that met the specific criteria established by the IACUC-approved protocol were euthanized and documented as an experimental death due to radiation-induced toxicity. Donor chimerism (% CD45.1+ cells) and lympho-myeloid lineage distribution were documented in the peripheral blood (PB) and BM in a separate cohort of mice, by flow cytometry following irradiation.

Flow Cytometry. LSK cells from Ly5a mice BM were enriched by using FACS as previously described (Varnum- Finney et al., Blood 1998, 91:4084-4091). Briefly, BM cells from B6-Ly5a mice were incubated with a lineage (LIN) cocktail prepared in house. The LIN cocktail included antibody against CD2 (clone RM2-5), CD3 (clone 17A2), CD5 (clone 53-7.3), CD8a (clone 53-6.7), CD11b (clone M1/70), GR1 (clone RB6-8), B220 (clone RA3-6B2), and TER-119 (clone TER-119). All antibodies were from BD Biosciences and raised in rats. After 10 minutes' incubation with LIN cocktail, the samples were washed and sheep anti-rat IgG beads (Dynabeads, Thermo Fisher Scientific Life Sciences) were added. The LIN-positive cells were separated using DynaMag magnets (Thermo Fisher Scientific Life Sciences). LIN-negative cells were stained with Sca1-PE (clone E13-161.7) and c-kit-fluorescein isothiocyanate (FITC) (clone 2B8), and LSK cells were isolated using an FACS ARIA II cell sorter.

Blood samples were collected by using the retro-orbital technique, and BM cells were aspirated from the right or left femur under general anesthesia. Following red cell lysis, PB and BM cells were incubated with a blocking reagent (PBS with 2% FBS, an anti CD16/CD32 antibody (2.4G2), and stained with the following antimouse-specific antibodies (all from BD un-less noted); CD45.1-PE-Cy7 (cloneA20), CD45.2-allophycocyanin (APC)-Cy7 (clone104), CD3-FITC (clone 17A2), Gr1-APC (cloneRB6-8C5), B220-APC (cloneRA3-6B2). Flow cytometric analysis was performed by using LSRII (BD Biosciences). All flow cytometry data were analyzed by using FlowJo software, version 9.0 (TreeStar, CA).

Skin Graft Procedure. In a subset of mice surviving >40 days, donor-specific tolerance was evaluated by subjecting these mice to bilateral allogeneic and syngeneic skin grafting. Bilateral allogeneic and syngeneic skin grafting was performed in two groups of BALB/cJ mice. The first group received a BALB/cJ skin graft on the left side and either a B6-Ly5a or a C3H (H-2k, CD45.2) skin graft on the right side. The second group of BALB/cJ mice received a B6-Ly5a skin graft on the left and a C3H skin graft on the right side. The technique was adapted from a previously reported method (McFarland and Rosenberg, Curr Protoc Immunol 2009, Chapter 4: Unit 4.4). Briefly, donor BALB/cJ, B6-Ly5a, and C3H mice were euthanized and the ventral and lateral trunk skin was collected, cut into small squares, and kept in cold PBS. Control (reconstituted with BALB/cJ bulk BM cells) and chimeric BALB/cJ mice were anesthetized with isoflurane, 7- to 10-mm graft beds were prepared bilaterally on the dorso-lateral thorax, the skin graft was placed and trimmed to size in situ, and the corners were anchored with interrupted sutures (5.0 wax-coated braided silk). Grafts were dressed with nonadherent absorbent gauze pads, paper tape, and vet wrap. After 7 days, the dressings and sutures were removed and the grafts were scored daily thereafter. The day of rejection was defined as >80% of the graft being necrotic, scabbed, or dislodged from the graft bed.

Statistical Analysis. All statistical analyses were performed by using Prism software, vVersion 6.0f (GraphPad, San Diego, Calif.) and p values <0.05 were considered to represent statistically significant differences. Results of experiments are represented as the mean 6 SEM. Engraftment data were analyzed by using a standardized Student t test, and overall survival and graft survival were analyzed by using Kaplan-Meier survival curve analyses. Logistic regression was used to calculate the dose of radiation expected to cause death to 50% of an exposed population within 30 days and to 70% of an exposed population within 30 days (LD70/30). The skin graft survival data were analyzed by using a stratified Wilcoxon (Breslow) test for equality of survivor functions.

Figure 6A:
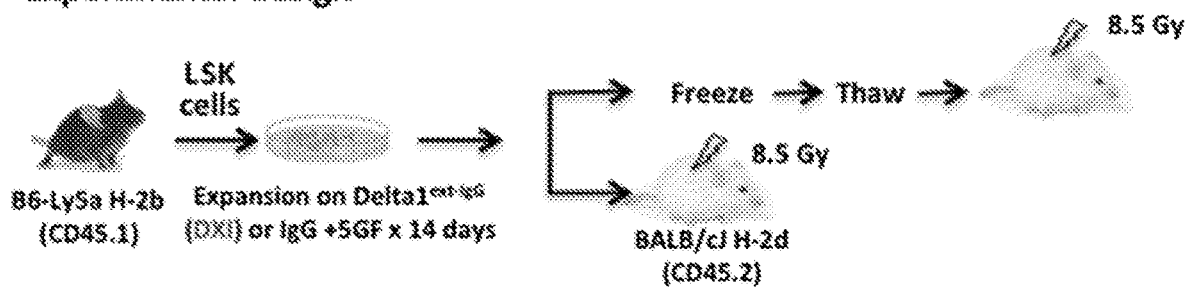
Figure 6B:
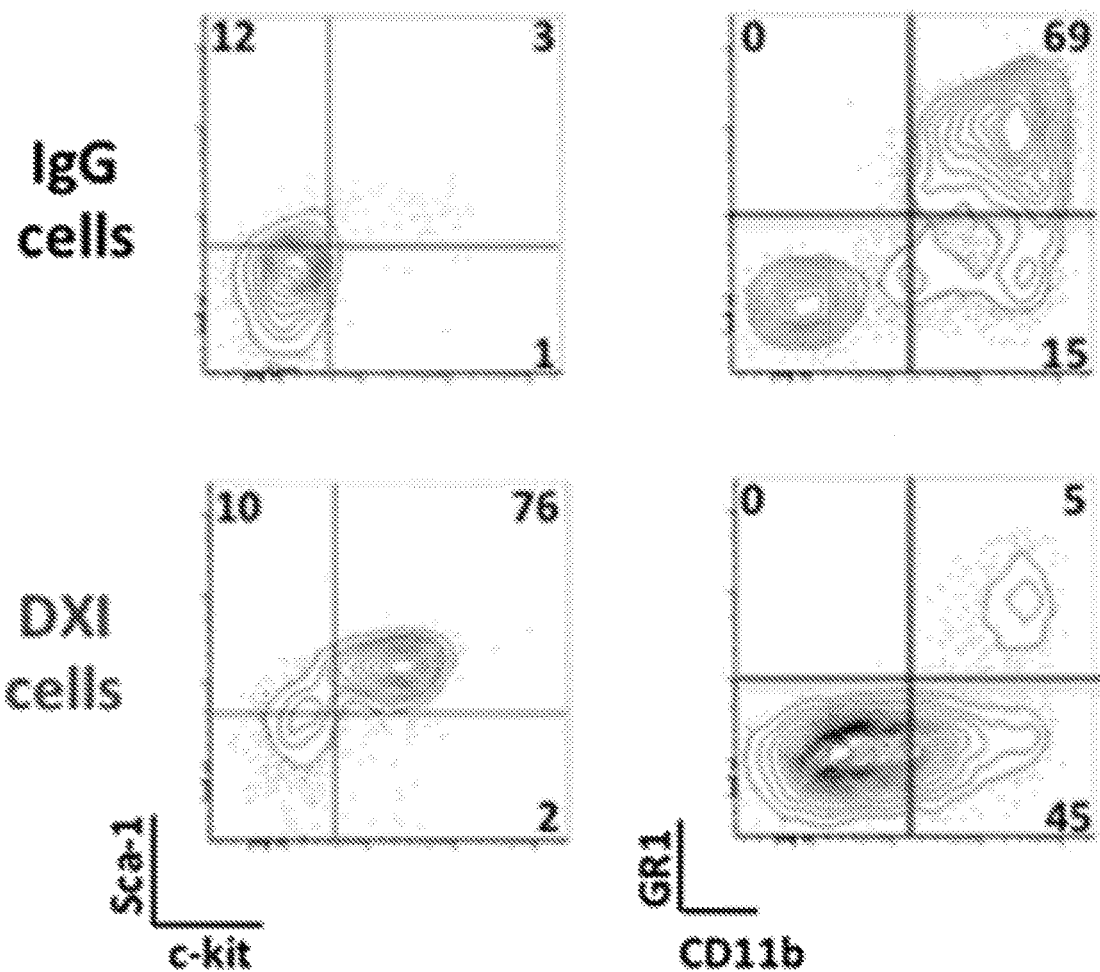

Infusion of Mismatched Expanded Murine Progenitor Cells After Lethal Radiation Results in Rapid Myeloid Recovery. It has previously been shown that mouse and human HSPCs expanded in cultures containing fibronectin fragments and immobilized Notch ligand efficiently repopulate syngeneic and xenogenic recipients (Varnum-Finney et al., 2003, 101:1784-1789; Delaney C et al., Blood 2005, 106:2693-2699). This study tested whether expanded murine HSPCs could similarly provide rapid hematopoietic reconstitution when infused into MHC mismatched recipients after lethal radiation. To achieve this, fresh $1 \times 10^6$ B6-Ly5a (H-2b, CD45.1) LSK cells, expanded with IgG or Delta1ext-IgG for 14 days, were injected into lethally irradiated (8.5 Gy) 6- to 8-week-old female BALB/cJ (H-2d, CD45.2) mice (FIG. 6A). As expected, at the end of the 14-day culture period, 76% of the Delta1ext-IgG-cultured cells were Sca-1+ c-Kit+ (FIG. 6B, left lower panel), and few expressed the granulocyte-associated (GR-1 and CD11b) antigens (FIG. 6B, right lower panel). In contrast, few cells cultured with control IgG were Sca-1+ c-Kit+, and most were GR-1+ and CD11b+ granulocytes, indicating differentiation (FIG. 6B, left and right top panels).

As early as 7 days after infusion with fresh DXI-cultured cells, a high level of engraftment was observed in both PB and BM of MHC mismatched mice (FIG. 6C). In these mice, donor cells continued to decrease over 8 weeks, resulting in a low level of donor cells in PB (4.5% 6 0.6%) up to 60 days after transplant. In contrast, donor engraftment at day 7 was low (24% 6 4%) in mice infused with control IgG-cultured cells and was detected only in the BM. By day 14, no donor engraftment was detected in this group (FIG. 6C). Early donor-derived hematopoietic reconstitution with DXI-cultured cells was predominantly myeloid (data not shown), whereas at 2 months after transplant, the donor-derived hematopoiesis was predominantly T-lymphoid cells, progeny of short-term repopulating cells expanded ex vivo (FIG. 6C, inset).

Figure 7B:
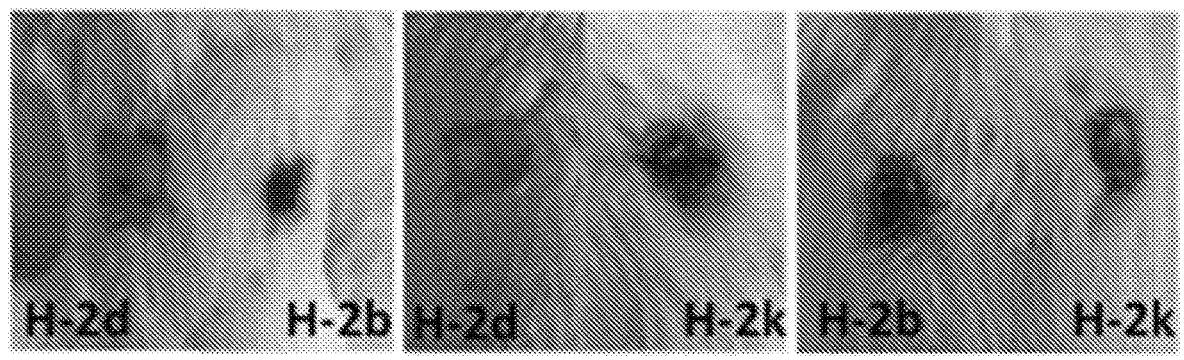

Infusion of Mismatched DXI-Cultured Cells Induces Donor-Specific Tolerance and Improves Skin Graft Survival (i.e., reduces transplant rejection). Long-term persistence of low levels of donor T cells in the PB of mice transplanted with DXI-cultured cells, with no evidence of graft-versus-host disease (GVHD), suggested the presence of donor-specific transplantation tolerance across full MHC barriers. To address whether these mice had developed donor-specific tolerance, they were challenged by surgical placement of a syngeneic (BALB/cJ, H-2d), donor (B6-Ly5a, H-2b), or third-party (C3H, H-2k) skin graft 60 days after they had been transplanted with control syngeneic BM or DXI-cultured cells. Every mouse was implanted with two skin grafts, one on each side of the flank; the origin of the graft on each flank was syngeneic/donor, syngeneic/third party or donor/third party (FIG. 7A). Six and four graft failures resulting from technical problems occurred in the control and DXI groups, respectively. None of the syngeneic skin grafts were rejected in mice previously transplanted with syngeneic BM (FIGS. 7B, 7E) or allogeneic DXI-cultured cells (FIGS. 7C, 7E), whereas all third-party skin grafts were rejected in all mice within the first 13 days after the graft placement, leaving behind contracted scar tissue (FIGS. 7B, 7C, 7G).

Figure 7C:
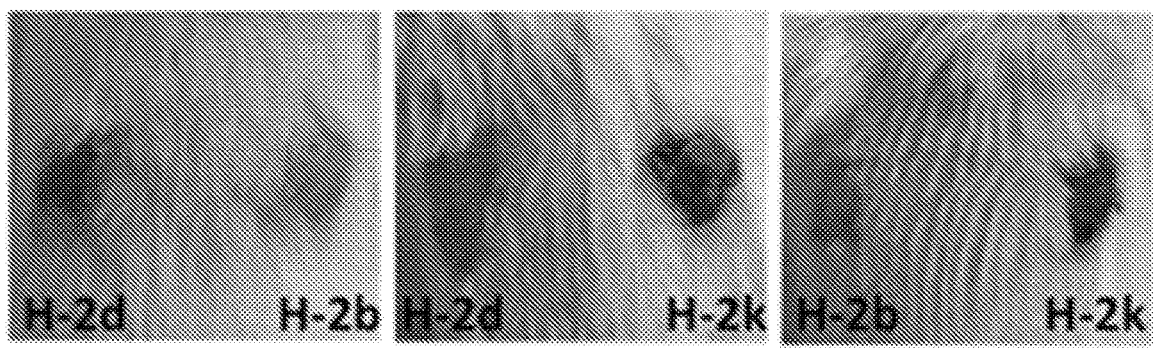
Figure 7D:
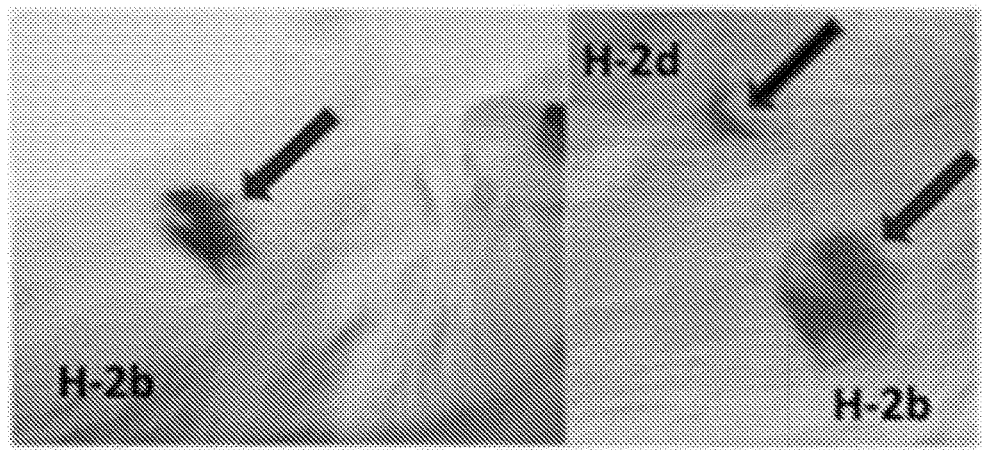
Figure 7E:
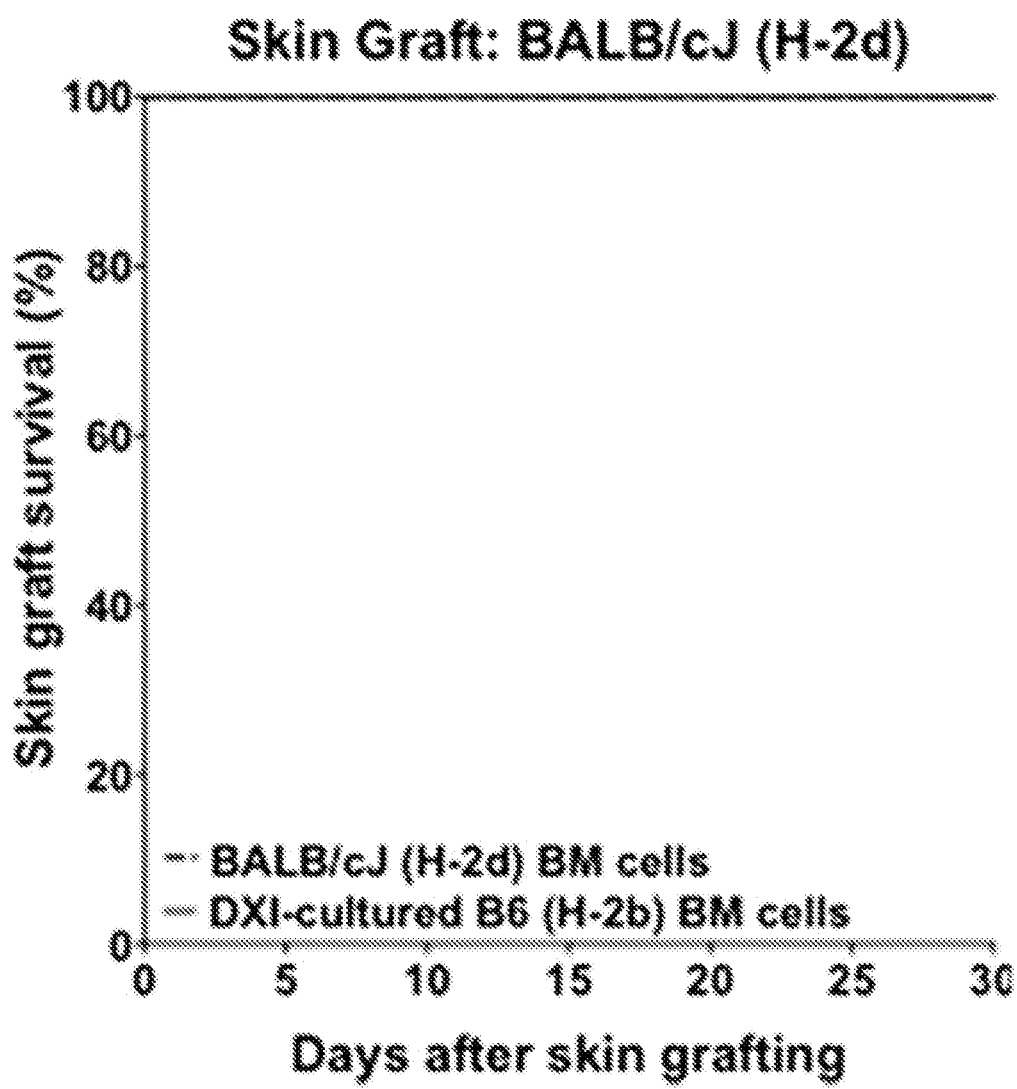
Figure 7F:
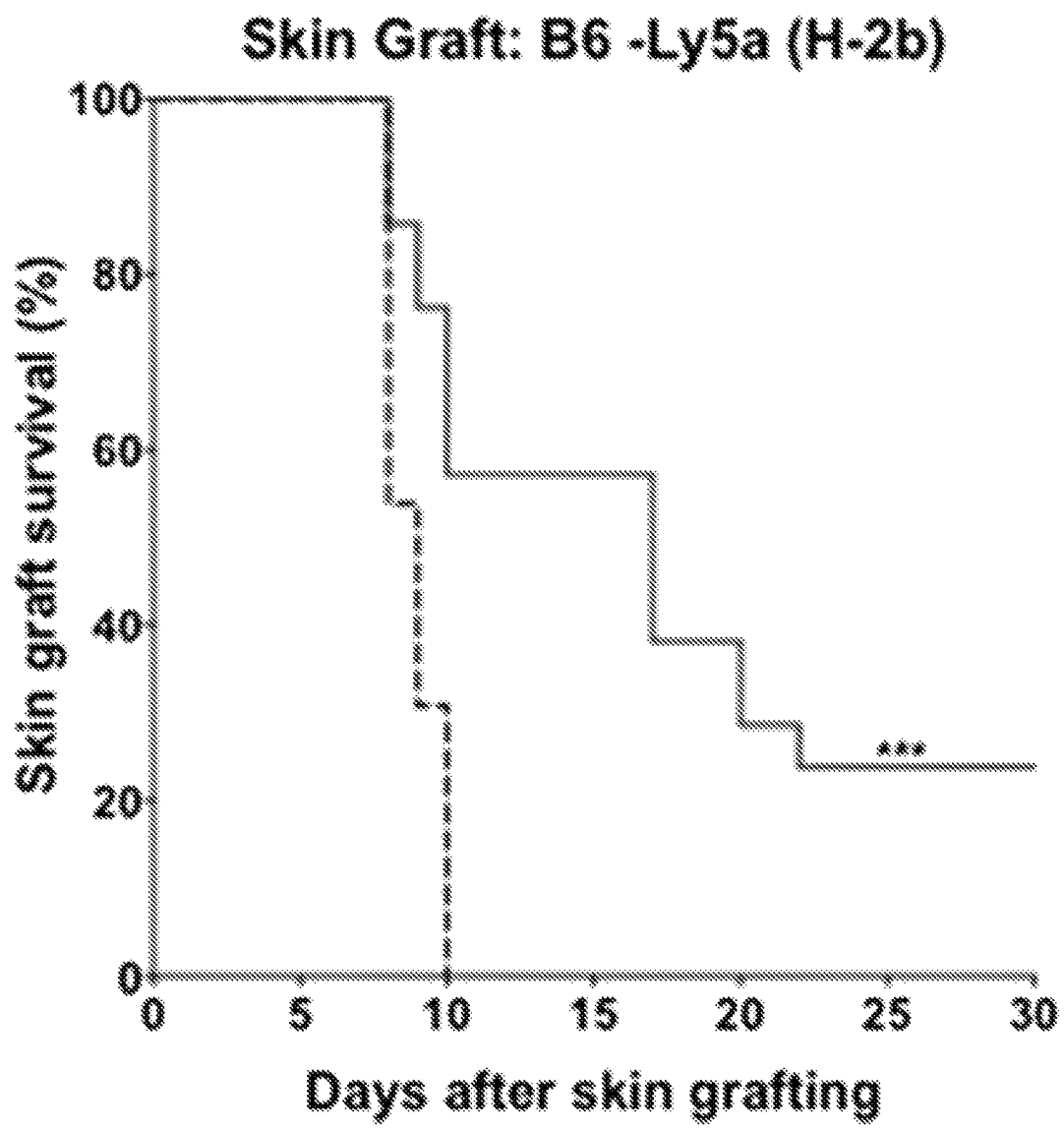
Figure 7G:
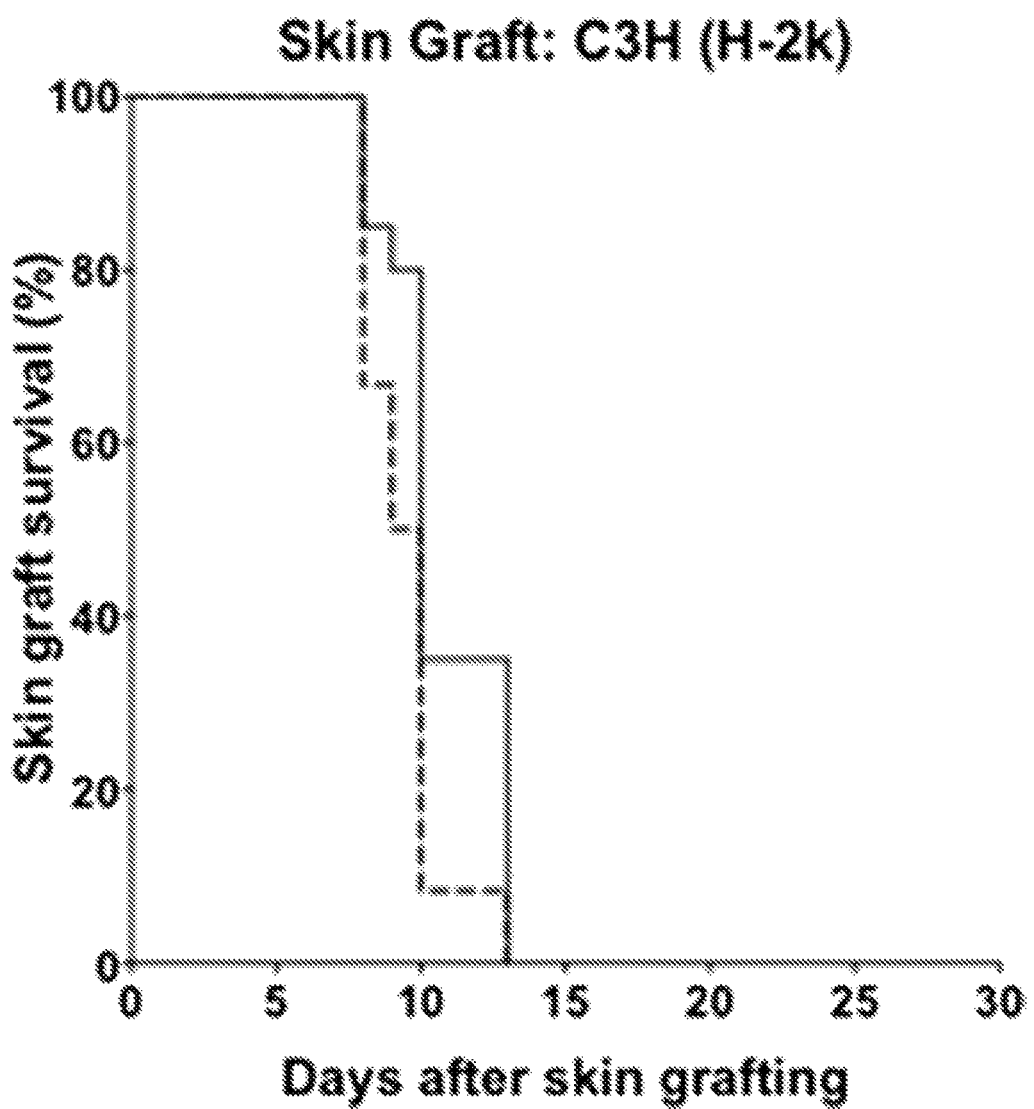

In contrast, the 30-day survival rate of donor grafts was significantly prolonged in the DXI group; by day 30, 48% (10 of 21) of the skin grafts appeared healthy and showed no signs of rejection (crusting and scarring) (FIGS. 7C, 7F;

p≤0.001). Moreover, 14% of these grafts showed complete engraftment, with evidence of black hair growth on a white hair background at the surgical site (FIG. 7D). Prolonged graft survival in these mice was not due to immune deficiency because the mice rejected all third-party skin grafts (FIGS. 7C, 7G). In stark contrast, all donor grafts were rejected in mice transplanted with syngeneic BM cells (FIGS. 7B, 7F). Intriguingly, the level of persistent donor engraftment in the PB at the time of skin grafting did not correlate with graft survival. Without being bound by theory, these results support the view that improved skin graft survival resulted from induction of donor-specific immune tolerance by infusion of cryopreserved allogeneic DXI-cultured cells. None of the mice surviving beyond the initial 30 days after TBI developed any long-term complications of radiation exposure during the experiment (90 days).

This example demonstrates that treatment with cryopreserved, ex vivo DXI-expanded murine HSPCs in MHC mismatched murine recipients after a wide range of lethal TBI doses led to rapid recovery of donor-derived myeloid cells by day 7 after the infusion of the expanded cell product, despite the major mismatch between the cells and the recipients. This example also demonstrates that sustained mixed donor chimerism in the BM and PB is possible across major H2 histocompatibility barriers in fully mismatched mice without any evidence of GVHD. Importantly, this study did not use post-transplant immunosuppression or anti-host antibody therapy, which was found to be required in previous studies (Cobbold et al., Nature 1986, 323:164-166; Yamada et al., Am J Transplant 2015, 15: 3055-3066; de Vries-van der Zwan et al., Bone Marrow Transplant 1998, 22:91-98).

In lethally irradiated mice, donor-derived engraftment peaked at day 7 with a predominance of myeloid cells. Thereafter, the level of donor engraftment declined, and by day 60, donor engraftment stabilized at a low level that was almost exclusively derived of predominantly CD3+ T lymphocytes without any evidence of GVHD. T lymphoid donor chimerism in these mice transplanted with MHC mismatched cells is similar to what was previously reported in mice transplanted with MHC matched, DXI-expanded cells (Varnum-Finney et al., 2003, 101:1784-1789), and the cells are the progeny of short-term lymphoid myeloid repopulating cells generated ex vivo. There does not seem to be an impact of Notch signaling on development of progeny T-cells generated from expanded repopulating cells because the Notch ligand Delta1 was used to induce proliferation while inhibiting differentiation of LSKs. Without being bound by theory, the induction of immune tolerance across full MHC barriers was demonstrated by a significantly higher skin graft survival rate in mice transplanted with DXI-expanded cells. There was not any observed correlation between the level of chimerism and graft survival, as previously reported by others (Sorof et al., Transplantation 1995, 59:1633-1635; Ildstad et al., J Exp Med 1985, 162: 231-244). A low level of T-cell chimerism (3.4% 6 5%; range, 0.2%-11.2%) was sufficient to convey donor-specific immunological tolerance to the skin grafts. However, the graft survival rate was higher (40%) in mice exposed to 8.0-Gy TBI than in mice exposed to 7.5-Gy TBI, in which only 1 of 10 skin grafts was not rejected at day 30. This study documented that prolonged skin allograft survival in these mice was specifically due to the recipients' lack of responsiveness against specific donor antigens by showing that they were responsive against third-party (C3H) antigens and rapidly rejected third-party skin grafts.

The current Example is the first to show the induction of donor-specific tolerance in recipients treated with cryopreserved, ex vivo expanded allogeneic, and mismatched HLA-HSPCs.

Example 2

Opioid Use, TPN Feeding and Days of Hospitalization following a Medical Procedure. Infusion of ex vivo expanded cord blood progenitor cells is associated with reduced hospital days and utilization of opiate infusion and total parental nutrition in pediatric patients receiving myeloablative cord blood transplantation.

Methods: Pediatric patients (<21 years old, n=34) receiving myeloablative conditioning (FLU/CY/13.2 Gy TBI) with or without expanded CB HSPC (fresh or cryopreserved) were included in this Example. Duration of initial hospitalization, use of opiate pain medications (by continuous infusion or PCA), and use of TPN were determined for each patient. Statistical comparisons between groups were made with two-tailed, unpaired t-tests.

Figure 9:
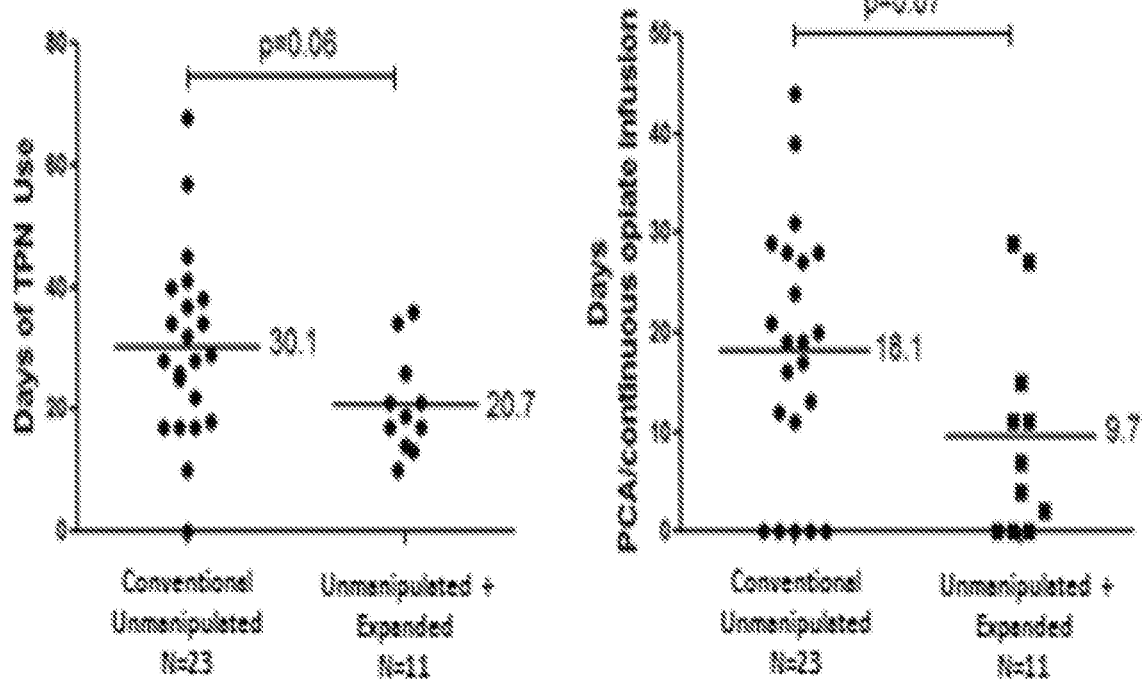
FIG. 9. Mean use of total parental nutrition (TPN, left panel) and opiate infusion (right panel) in pediatric patients receiving myeloablative cord blood transplantation with or without ex-vivo expanded progenitors.

Results: 11 patients received expanded CB HSPC in addition to 1-2 unmanipulated CB units while a concurrent cohort of 23 patients received the same conditioning regimen without expanded cell infusion. The mean duration of initial hospitalization following the medical procedures was 43.2 v. 55.6 days (p=0.05) (FIG. 8), the mean duration for continuous opiate medications 9.7 v. 18.1 days (p=0.07), and mean time receiving TPN was 20.7 v. 30.1 days (p=0.06) (FIG. 9).

This Example demonstrates important additional benefits of the Exp-CBSC. Reduced total parenteral feeding avoids the numerous complications that can arise due to such artificial feeding. Reducing patient exposure to opioid use can help address the on-going epidemic of pain killer abuse. Finally, reduced hospitalization following a medical procedure decreases costs associated with medical care and similarly reduces lost opportunity costs patients experience while hospitalized.

Example 3

Reduced Acute GVHD. A prospective open-label single arm study to assess the safety, feasibility and preliminary efficacy in patients undergoing a single or double CBT followed by infusion of a non HLA-matched, previously ex vivo expanded and cryopreserved CB progenitor cell product was conducted.

Patients. Eligible patients were 6 months to ≤45 years of age and had high-risk acute leukemia, chronic myeloid leukemia, or myelodysplastic syndrome. Additional inclusion requirements included adequate performance status, adequate organ function, and availability of one or two CB units matched at four of more HLA loci by intermediate-resolution for HLA class I alleles (A and B) or by high-resolution typing for the HLA class II DRB1 allele. Single unit CBT was permitted for 6/6 units with total nucleated cell count (TNC)≥2.5×10$^7$/kg, 5/6 and 4/6 units with TNC≥4.0×10$^7$/kg. If these thresholds were not met, double unit CBT (dCBT) was performed, with each unit required to have a TNC≥1.5×10$^7$/kg.

Ex-vivo expanded progenitor cell products: Cell processing and manufacturing. Briefly, human CB samples were obtained from normal full-term deliveries with Institutional Review Board approval and donor eligibility determined as per 21CFR1271 by the Puget Sound Blood Center Cord Blood Bank. The CB units were red cell depleted and underwent clinical grade selection of CD34+ cells using the Miltenyi CliniMACS per the manufacturer's instructions. The negative fraction was discarded.

Cultures were initiated with the purified CD34+ cells and cultured for 14-16 days in non-tissue culture treated 75-225 cm$^2$ tissue culture flasks (Nunc, Thermo Fisher Scientific, Pittsburgh, USA). Culture vessels were pre-coated with clinical grade Notch ligand (Delta1ext-IgG, prepared in the Fred Hutchinson's Biologics Production Facility, DMF BB-MF 12366) at 2.5 µg/ml (a density previously been shown to be optimal for generation of NOD/SCID repopulating cells), together with 5 ng/ml of fibronectin fragment CH-296 (Takara Shuzo Co. LTD., Otsu, Japan) 2 hours at 37° or overnight at 4°, washed with PBS. Cells were cultured in serum-free medium (Stemspan SFEM, Stemcell Technologies, Vancouver, BC, Canada) with clinical grade recombinant human IL-3 (10 ng/ml), IL-6, Thrombopoietin (TPO), Flt-3 Ligand and Stem Cell Factor (SCF) at 50 ng/ml) (CellGenix Freiburg, Germany). Cells were split into new culture vessels to maintain a cell density of <1×10$^6$ total cells per milliliter of media.

Figure 10A:
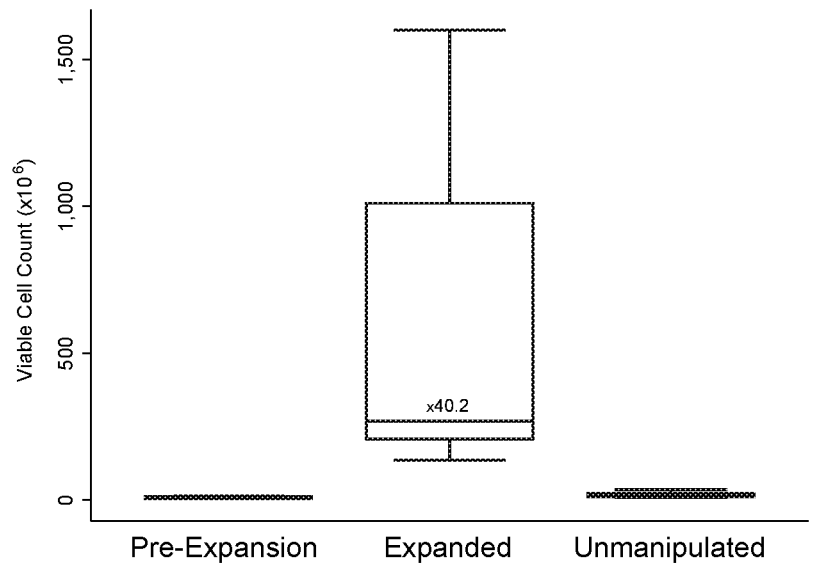
FIGS. 10A-10B. Median numbers (bar), interquartile range (box), and range (whiskers) of CD34+ cells (FIG. 10A) and total nucleated cells (FIG. 10B), respectively, contained in the cord blood graft before and after ex-vivo expansion compared to the total number in the unmanipulated cord blood unit(s). The numbers of nucleated cells were not statistically different between expanded and the combined unmanipulated nucleated cell number (p=0.787); however, the number of CD34+ cells was significantly higher in the expanded cord blood (p<0.0001). There were significant increases in nucleated cells and CD34+ cells in the expanded cord blood compared with the values before expansion (p=0.0006 and p<0.0001, respectively). Nucleated cells were expanded by a median factor of 1.9 (range 0.8 to 6.9) and CD34+ cells by a median factor of 40.2 (range 23.8 to 123.1).
Figure 10B:
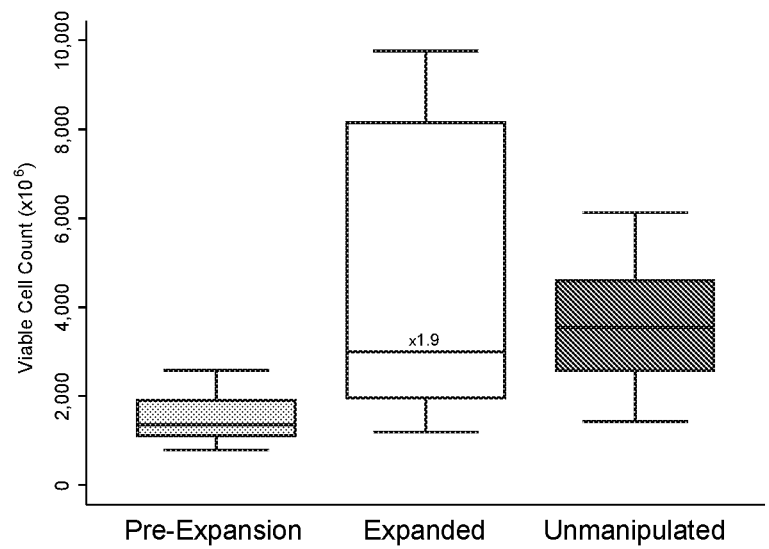

On day 14-16 of culture, the total volume of cells was harvested and final release testing performed, including final cell counts and calculation of CD34 and TNC fold expansion, immunophenotyping, bacterial and fungal sterility and endotoxin. FIGS. 10A and 10B depict fold average expansion of CD34+ cells (FIG. 10A) and an average fold expansion of total nucleated cell numbers (FIG. 10B) of at the time of harvest of the expanded cell product. The product was then cryopreserved in a controlled rate freezer.

Final collected HSPC product. Of note, there were no mature T cells infused with the expanded graft as the product consisted of the total progeny generated after culture of CD34+ HSPC isolated from a single CB unit. The T cells contained in the negative fraction were not retained and no T cells are generated or maintained in the 14 day culture period. The median pre-freeze TNC and CD34+ cell dose derived from the Exp-CBSC was 5.8×10$^7$/Kg (range 2.2 to 10.9) and 0.26×10$^6$/kg (range 3.1 to 11.6), respectively. The median pre-freeze TNC and CD34+ cell dose derived from the unmanipulated graft was 6.1×10$^7$/Kg (range 4.3 to 17.1) and 0.26×10$^6$/kg (range 0.08 to 0.98), respectively. Patients receiving the Exp-CBSC had a significant higher TNC in the unmanipulated units when compared to TNC for patients in the control group (FIG. 11).

Statistical analysis. Probability of disease free survival (DFS) was made using the method of Kaplan and Meier [MacMillan et al., Blood 2009; 113:2410-15]. Cumulative incidence of relapse, non-relapse mortality (NRM), and acute GVHD were summarized using cumulative incidence estimates, with relapse regarded as a competing risk for NRM, NRM a competing risk for relapse, and death without failure for each of the other endpoints regarded as a competing risk for each, respectively.

DFS, NRM, acute GVHD in the group of patients who received Exp-CBSC were compared with the outcomes of 50 patients who received a CBT without EPC. All patients received the same conditioning regimen and GVHD prophylaxis. Incidence of relapse, NRM and acute GVHD were compared using the Fine and Gray method.

Results. The median follow up of surviving patients was 4.2 years (range, 2.9 to 4.8 years). Patients were 5-45 (median 21) years old and weighed 23-89 (median 59) kg. Diseases included AML (n=6), ALL (n=8), MDS (n=1). Six patients (40%) had minimal residual disease at the time of transplant, defined as presence of disease assessed by ten-color multiparameter flow cytometry on bone marrow aspirates obtained as a routine baseline before HCT. All but 4 patients (27%) received 2 CB units to achieve the required cell dose. When compared to the control group no differences were seen with respect to sex, age, weight, CMV serostatus and disease status at transplantation.

Figure 12A:
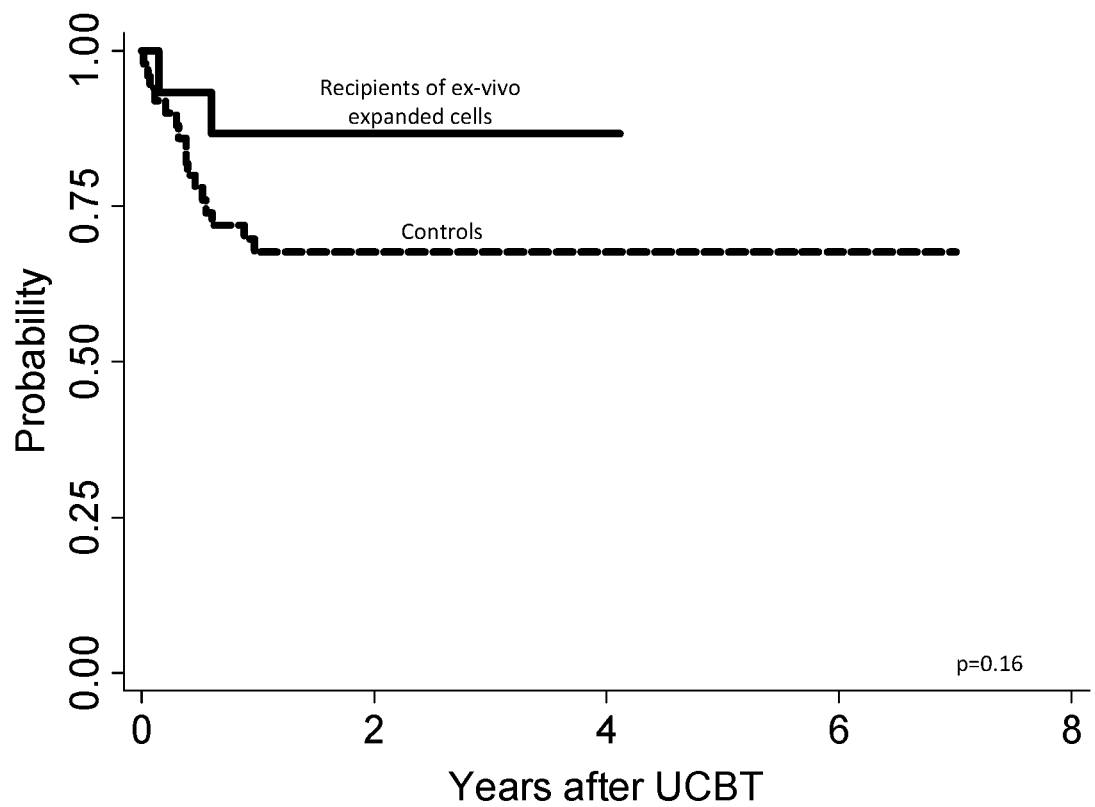
FIGS. 12A-12C. Disease-Free Survival (DFS) at 3 years (FIG. 12A): recipients ex-vivo expanded cells 86% (95% CI: 56-96) vs. controls 67% (95% CI: 52-78). Cumulative incidence non-relapse mortality by group (FIG. 12B). Significantly higher transplant-related mortality (TRM) among patients in the control group with no cases of TRM in recipients of ex-vivo expanded cells: 16% (95% CI: 7-27) vs. 0. Cumulative incidence relapse mortality by group (FIG. 12C). No significant differences between the 2 groups: recipients ex-vivo expanded cells 13% (95% CI: 2-34) vs. controls 16% (95% CI: 7-28).
Figure 12B:
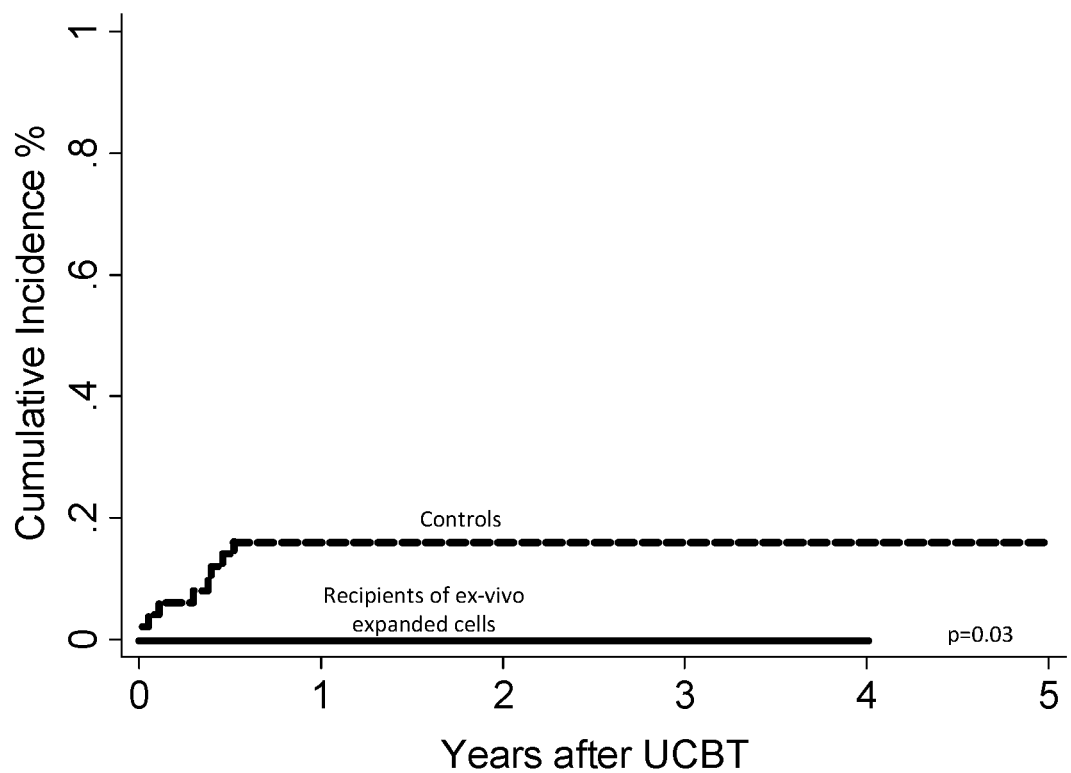
Figure 12C:
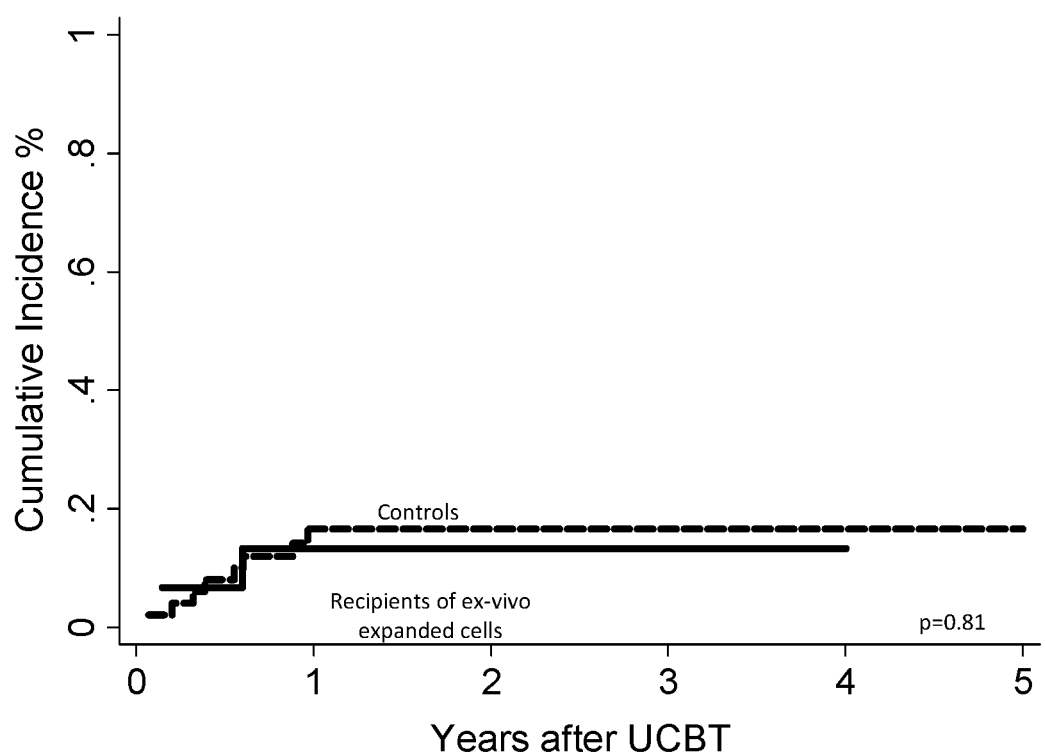

Transplant outcomes. The probability of 3-year DFS was 86% (95% CI: 57-97) among recipients of Exp-CBSC and 67% (95% CI: 52-78) in the controls (p=0.16) (FIG. 12A). FIG. 6B and FIG. 12C show the cumulative incidence of NRM and relapse among recipients of Exp-CBSC compared to controls, respectively. No NRM was observed throughout the study period, although 2 patients relapsed at days 53 and 219 posttransplant and subsequently died after further therapy. The patient who relapsed at 53 was in frank relapse at the time of transplantation.

Figure 13:
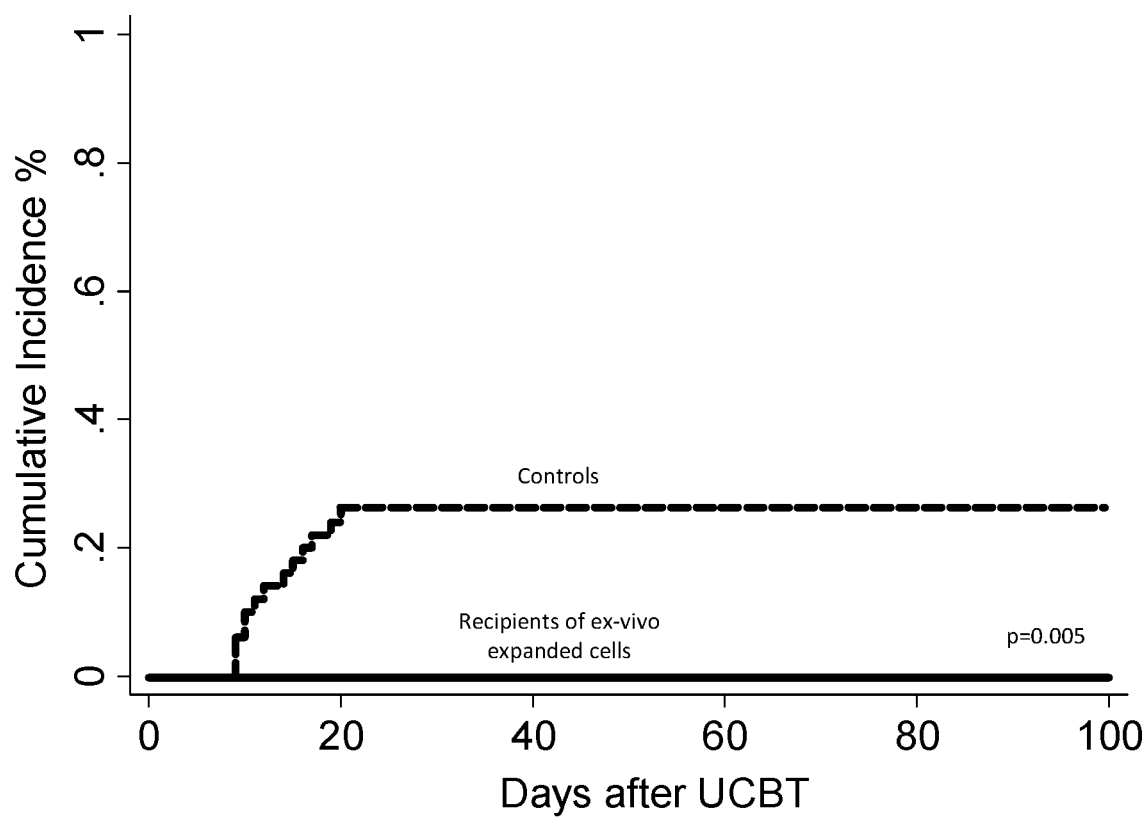
FIG. 13. Cumulative incidence for more severe grade III-IV acute GVHD by group. Significant difference between patients receiving ex-vivo expanded cells vs. patients in the control group: Recipients of ex-vivo expanded cells 0% vs. controls 26% (95% CI: 14-38).

Acute and Chronic GVHD. All patients were diagnosed with maximum grade II acute GVHD at a median time of 32 days (14-86), with no grade III-IV aGVHD observed. In contrast, the cumulative incidence of grade III-IV aGVHD was 26% in the controls (p=0.005) (FIG. 13). The skin was the most commonly affected organ in the group receiving the Exp-CBSC (n=12). Eight (53%) patients were treated for pre-engraftment syndrome at a median time of 6 days (range 4-9) and five (33%) patients had GVHD after day 100. After day 100, of the 13 patients evaluable, 3 (23%) had late aGVHD features or an overlap syndrome, while none was diagnosed with features of classical cGVHD. At 2 years, nine patients (70%) were off immunosuppression.

Transplant related deaths were not observed among the 15 patients on this study; however, 2 deaths due to relapsed disease occurred, leading to an excellent overall survival. The positive outcomes observed can be attributed to overcoming the delay of engraftment experienced by patients undergoing a CBT; however it is also possible that the infusion of the off-the-shelf Exp-CBSC led to augmenting the graft-versus graft interactions and consequently increasing the graft-versus-leukemia effect. Although the small number of patients does not allow drawing definitive conclusions, the characteristics of the patients (half of them were MRD+ at the time of transplant) and the long follow-up make these results extremely encouraging.

No infusion-related toxicities were observed and no serious adverse events were attributed to the off-the-shelf Exp-CBSC product. More surprisingly, none of the patients included in the study experienced grade III-IV aGVHD suggesting immunomodulatory properties of the off-the-shelf product. It is possible that in the presence of the off-the-shelf expanded product, the alloreactive T cells from the unmanipulated unit will expand in vivo and differentiate into specific cell subsets that are able to reduce aGvHD. If confirmed, this observation can have important clinical implications. Considering that severe forms of aGVHD are associated with an increased risk of morbidity and mortality, [Brunstein et al., Blood 2007; 110:3064-70; MacMillan et al., Blood 2009; 113:2410-15] the use of the off-the-shelf product could be extended to other types of HCT using different stem cell sources with the goal of mitigating aGVHD.

As will be understood by one of ordinary skill in the art, each embodiment disclosed herein can comprise, consist essentially of or consist of its particular stated element, step, ingredient or component. "Includes" or "including" means "comprises, consists essentially of or consists of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would result in a statistically significant and clinically meaningful reduction in the effectiveness of Exp-CBSC administration in reducing (i) transplant rejection, (ii) TPN, opioid use, and hospitalization days following a medical procedure; (iii) mucositis; or (iv) the occurrence and/or severity of grade III and grade IV acute GVHD following cord blood transplant according to a protocol described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to books, journal articles, treatises, patents, printed publications, etc. (collectively "references") throughout this specification. Each of the above-cited references are individually incorporated by reference herein for their cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of inducing immune tolerance in a transplant recipient comprising:
    administering a therapeutically effective amount of a CD34+ enriched and expanded cord blood product that does not include mature T cells to the transplant recipient, thereby inducing immune tolerance in the transplant recipient wherein the cord blood product is HLA-unmatched to the transplant recipient and the transplant is allogeneic.

2. The method of claim 1, wherein the cord blood product was expanded in a culture comprising a Notch agonist.

3. The method of claim 1, wherein the cord blood product was previously cryo-preserved.

4. The method of claim 1, wherein the cord blood product was derived from the umbilical cord blood and/or placental blood of a single human at birth.

5. The method of claim 1, wherein the cord blood product comprises a pool of two or more different expanded human cord blood stem cell populations, each different population in the pool derived from the umbilical cord blood and/or placental blood of a different human at birth and wherein blood stem cell populations are pooled without immunological matching to each other or to the transplant recipient.

6. The method of claim 1, wherein immune tolerance in the transplant recipient is evidenced by improved transplant outcomes related to immune responsiveness, the outcomes selected from (a) by reduced transplant rejection as compared to a reference population not receiving the cord blood product, or (b) reduced administration of immuno-suppressant drugs as compared to a reference population not receiving the cord blood product.

7. The method of claim 1, wherein the administering of the cord blood product to the transplant recipient occurs before receipt of the transplant.

8. The method of claim 1, wherein the administering of the cord blood product to the transplant recipient is within 36 hours of receiving the transplant.

9. The method of claim 8, wherein the administering of the cord blood product to the transplant recipient is within 12 hours of receiving the transplant.

10. The method of claim 1, wherein the transplant recipient is a pediatric transplant recipient.

11. The method of claim 1, wherein the transplant is a solid tissue transplant.

12. A method to improve transplant outcome in a recipient of a transplant, comprising administering to a recipient of a transplant a therapeutically effective amount of a Notch agonist expanded cord blood product which does not include mature T cells, wherein the expanded cord blood product is HLA-unmatched to the recipient, in which improved transplant outcome is evidenced by one or more of:
    (a) reduced total parenteral nutrition (TPN) in the recipient;
    (b) reduced amount or frequency of opioid treatments in the recipient;
    (c) reduced hospitalization time of the recipient;
    (d) reduced mucositis in the recipient; and
    (e) reduced Stage III and Stage IV acute graft versus host disease in the recipient, as compared to a reference population of transplant recipients not receiving the expanded cord blood product.

13. The method of claim 12, wherein the cord blood product was previously cryo-preserved.

14. The method of claim 12, wherein the cord blood product is derived from the umbilical cord blood and/or placental blood of a single human at birth.

15. The method of claim 12, wherein the cord blood product comprises a pool of two or more different expanded human cord blood stem cell populations, each different population in the pool derived from the umbilical cord blood and/or placental blood of a different human at birth and wherein blood stem cell populations are pooled without immunological matching to each other or to the transplant recipient.

16. The method of claim 12, wherein the administering of the cord blood product to the transplant recipient occurs before receipt of the transplant.

17. The method of claim 12, wherein the administering of the cord blood product to the transplant recipient is within 36 hours of receiving the transplant.

18. The method of claim 17, wherein the administering of the cord blood product to the transplant recipient is within 12 hours of receiving the transplant.

19. The method of claim 12, wherein the transplant is allogeneic.

20. The method of claim 12, wherein the transplant recipient is a pediatric transplant recipient.

21. The method of claim 12, wherein the transplant is a solid tissue transplant.

22. The method of claim 21, wherein the transplant comprises adipose tissue, a blood vessel, bone, bone marrow, cardiac cells, cartilage, cartilaginous cells, chondral cells, cochlea, connective tissue, a cornea, cultured cell monolayers, dental tissue, an eye, a face, fascia, fibrous tissue, a foot, a functional spine unit, hair, a hand, a heart, a heart valve, intestine, islet cells, kidney, a lens, a ligament, liver, lung, meniscus, muscle-tendon grafts, muscle tissue, neural cells, neural tissue, osteochondral cells, osteogenic cells, an ovary, pancreas, semi-tendinous tissues, skin, spleen, stomach, tendons, testis, a tooth, or a vertebral disc.

23. A method for reducing acute graft versus host disease (GvHD) in an allogeneic transplant recipient at risk of GvHD, comprising administering to the transplant recipient a therapeutically effective amount of an unmatched CD34+ enriched and expanded cord blood product that does not contain mature T cells, thereby reducing acute GvHD in the transplant recipient.

24. A method for reducing rejection of allogeneic tissue in a transplant recipient, comprising administering to the transplant recipient a therapeutically effective amount of an unmatched CD34+ enriched and expanded cord blood product that does not contain mature T cells, thereby reducing rejection of the allogeneic tissue.

25. The method of claim 24, wherein the tissue is a skin graft.

26. The method of claim 24, wherein the tissue comprises solid tissue.

* * * * *

UNITED STATES PATENT AND TRADEMARK OFFICE
CERTIFICATE OF CORRECTION

PATENT NO. : 10,813,949 B2  
APPLICATION NO. : 15/781447  
DATED : October 27, 2020  
INVENTOR(S) : C. Delaney It is certified that error appears in the above-identified patent and that said Letters Patent is hereby corrected as shown below:

In the Specification

Column 1, Line 16 Statement of Government Support should read:
"This invention was made with government support under grant number HL101844 awarded by the National Institutes of Health and grant number HHS0100200800064C awarded by the Department of Health and Human Services. The government has certain rights in the invention."

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*